US012590306B2

(12) United States Patent
Totaro et al.

(10) Patent No.: US 12,590,306 B2
(45) Date of Patent: Mar. 31, 2026

(54) PROCESSES FOR PREPARING PHOSPHORODIAMIDATE MORPHOLINO OLIGOMERS VIA FAST-FLOW SYNTHESIS

(71) Applicants: Sarepta Therapeutics, Inc., Cambridge, MA (US); Massachusetts Institute of Technology, Cambridge, MA (US)

(72) Inventors: Kyle A. Totaro, Cambridge, MA (US); Mark D. Simon, Cambridge, MA (US); Ming Zhou, Cambridge, MA (US); Hong Zong, Cambridge, MA (US); Gunnar J. Hanson, Cambridge, MA (US); Bradley L. Pentelute, Cambridge, MA (US)

(73) Assignees: Sarepta Therapeutics, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 18/749,007

(22) Filed: Jun. 20, 2024

(65) Prior Publication Data

US 2025/0043283 A1 Feb. 6, 2025

Related U.S. Application Data

(63) Continuation of application No. 16/650,305, filed as application No. PCT/US2018/052524 on Sep. 25, 2018, now abandoned.

(60) Provisional application No. 62/562,741, filed on Sep. 25, 2017.

(51) Int. Cl.
*C12N 15/113* (2010.01)

(52) U.S. Cl.
CPC ........ *C12N 15/113* (2013.01); *C12N 2310/11* (2013.01); *C12N 2310/314* (2013.01); *C12N 2310/3233* (2013.01); *C12N 2330/30* (2013.01)

(58) Field of Classification Search
CPC .......... C12N 15/113; C12N 2310/3233; C12N 2310/11; C12N 2330/30; A61K 31/712; A61K 31/7215
USPC ..................................... 514/44 A; 536/25.31
See application file for complete search history.

(56) References Cited

U.S. PATENT DOCUMENTS

| | | | |
|---|---|---|---|
| 5,034,506 | A | 7/1991 | Summerton et al. |
| 5,142,047 | A | 8/1992 | Summerton et al. |
| 5,166,315 | A | 11/1992 | Summerton et al. |
| 5,185,444 | A | 2/1993 | Summerton et al. |
| 5,217,866 | A | 6/1993 | Summerton et al. |
| 5,506,337 | A | 4/1996 | Summerton et al. |
| 5,521,063 | A | 5/1996 | Summerton et al. |
| 5,698,685 | A | 12/1997 | Summerton et al. |
| 8,067,571 | B2 | 11/2011 | Weller et al. |
| 8,076,476 | B2 | 12/2011 | Reeves et al. |
| 8,299,206 | B2 | 10/2012 | Fox et al. |
| 8,969,551 | B2 | 3/2015 | Ueda |
| 9,394,323 | B2 | 7/2016 | Iversen |
| 2016/0076033 | A1 | 3/2016 | Torii et al. |
| 2016/0208264 | A1 | 7/2016 | Wilton et al. |
| 2020/0362339 | A1 | 11/2020 | Totaro et al. |

FOREIGN PATENT DOCUMENTS

| | | | | |
|---|---|---|---|---|
| JP | 2019517605 A | 6/2019 | | |
| JP | 2019518832 A | 7/2019 | | |
| JP | 2019523754 A | 8/2019 | | |
| TW | 201540724 A | 11/2015 | | |
| WO | WO-9002749 A1 | 3/1990 | | |
| WO | WO-2008036127 A2 | 3/2008 | | |
| WO | WO-2009064471 A1 | 5/2009 | | |
| WO | WO-2012043730 A1 | 4/2012 | | |
| WO | WO-2013082551 A1 | 6/2013 | | |
| WO | WO-2014153240 A2 | 9/2014 | | |
| WO | WO2017/062835 A1 * | 4/2017 | .......... | C12N 15/113 |
| WO | WO-2017062835 A2 | 4/2017 | | |
| WO | WO-2017205496 A1 | 11/2017 | | |
| WO | WO-2019060862 A1 | 3/2019 | | |

OTHER PUBLICATIONS

Harakawa et al, Bioorganic & Medicinal Chemistry Letters, 2012, 22, 1445-1447.*

European Search Report for EP Application No. 18859106.9, European Patent Office, Netherlands, mailed on Apr. 12, 2021, 7 pages.

International Search Report and Written Opinion for International Application No. PCT/US2018/052524, International Search Authority, United States, mailed Nov. 26, 2018, 7 pages.

Harakawa, T., et al., "Development of an Efficient Method for Phosphorodiamidate Bond Formation by Using Inorganic Salts," Bioorganic & Medicinal Chemistry Letters 22(3):1445-1447, Elsevier Science Ltd, United Kingdom (Feb. 2012).

Alul, R.H., et al., "Oxalyl-CPG: A Labile Support for Synthesis of Sensitive Oligonucleotide Derivatives," Nucleic Acids Research 19(7):1527-1532, Oxford University Press, England (Apr. 1991).

Arora, V., et al., "Bioavailability and Efficacy of Antisense Morpholino Oligomers Targeted to c-myc and Cytochrome P-450 3A2 Following Oral Administration in Rats," Journal of Pharmaceutical Sciences 91(4):1009-1018, Elsevier, United States (Apr. 2002).

Atherton, E., et al., "Letter: Polyamide Supports for Polypeptide Synthesis," Journal of the American Chemical Society 97(22):6584-6585, American Chemical Society, United States (Oct. 1975).

(Continued)

*Primary Examiner* — Ganapathy Krishnan

(74) *Attorney, Agent, or Firm* — STERNE, KESSLER, GOLDSTEIN & FOX P.L.L.C.

(57) ABSTRACT

Provided herein are processes for preparing an oligomer (e.g., a morpholino oligomer). The synthetic processes described herein may be advantageous to scaling up oligomersynthesis while maintaining overall yield and purity of a synthesized oligomer.

13 Claims, 13 Drawing Sheets

(56) References Cited

OTHER PUBLICATIONS

Atherton, E., et al., "Peptide Synthesis. Part 2. Procedures for Solid-phase Synthesis Using Nα-fluorenylmethoxycarbonylamino-acids on Polyamide Supports. Synthesis of Substance P and of Acyl Carrier Protein 65-74 Decapeptide," Journal of the Chemical Society, Perkin Transactions 1 0:538-546, Royal Society of Chemistry, United Kingdom (1981).
Atherton, E., et al., "The Polyamide Method of Solid Phase Peptide and Oligonucleotide Synthesis," Bioorganic Chemistry 8(3):351-370, Elsevier, Netherlands (Sep. 1979).
Bayer, E., and Jung, G., "A New Support for Polypeptide Synthesis in Columns," Tetrahedron Letters, 51:4503-4505, Pergamon Press, United Kingdom (Nov. 1970).
Berg, R.H., et al., "Long-chain polystrene-grafted polyethylene film matrix: A new support for solid phase peptide synthesis," Journal of the American Chemical Society 111(20):8024-8026, American Chemical Society, United States (Sep. 1989).
Bonora, G.M., et al., "A Liquid-Phase Process Suitable for Large-Scale Synthesis of Phosphorothioate Oligonucleotides," Organic Process Research & Development 4(3):225-231, American Chemical Society (2000).
Chan, J.H.P., et al., "Antisense Oligonucleotides: From Design to Therapeutic Application," Clinical and Experimental Pharmacology 33(5-6):533-540, Wiley Online Library, United States (May 2006).
Cirak, S., et al., "Exon Skipping and Dystrophin Restoration in Patients With Duchenne Muscular Dystrophy After Systemic Phosphorodiamidate Morpholino Oligomer Treatment: An Open-label, Phase 2, Dose-escalation Study," Lancet 378(9791):595-605, Elsevier, England (Aug. 2011).
Daniels, S.B., et al., "Membranes as Solid Supporters for Peptide Synthesis," Tetrahedron Letters 30:4345-4348, Elsevier, Netherlands (Jan. 1989).
Eliel, E.L., and Wilen, S.H., "Chirality in Molecules Devoid of Chiral Centers," in *Stereochemistry of Carbon Compounds*, pp. 1119-1190, John Wiley & Sons, New York, United States (1994).
Ge, Q., et al., "Inhibition of Multiple Subtypes of Influenza A Virus in Cell Cultures with Morpholino Oligomers," Antimicrobial Agents and Chemotherapy 50(11):3724-3733, American Society for Microbiology, United States (Nov. 2006).
Geysen, H.M., et al., "Use of Peptide Synthesis to Probe Viral Antigens for Epitopes to a Resolution of a Single Amino Acid," Proceedings of the National Academy of Sciences of the United States of America 81(13):3998-4002, National Academy of Sciences, United States (Jul. 1984).
Goemans, N.M., et al., "Systemic Administration of PRO051 in Duchenne's Muscular Dystrophy," The New England Journal of Medicine 364(16):1513-1522, Massachusetts Medical Society, United States (Apr. 2011).
Gravert, D.J., et al., "Organic Synthesis on Soluble Polymer Supports: Liquid-phase Methodologies," Chemical Reviews 97(2):489-510, American Chemical Society, United States (Apr. 1997).
Holden, L., et al., "Inhibition of Dengue Virus Translation and RNA Synthesis by a Morpholino Oligomer Targeted to the Top of the Terminal 3' Stem-loop Structure," Virology 344(2):439-452, Academic Press, United States (Jan. 2006).
Houghten, R.A, "General Method for the Rapid Solid-phase Synthesis of Large Numbers of Peptides: Specificity of Antigen-antibody Interaction at the Level of Individual Amino Acids," Proceedings of the National Academy of Sciences of the United States of America 82(15):5131-5135, National Academy of Sciences, United States (Aug. 1985).
Hudziak, R.M., et al., "Resistance of Morpholino Phosphorodiamidate Oligomers to Enzymatic Degradation," Antisense & Nucleic Acid Drug Development 6(4):267-272, Mary Ann Liebert, Inc., United States (1996).
Iversen, P.L., et al., "Discovery and Early Development of AVI-7537 and AVI-72888 for the Treatment of Ebola Virus and Marburg Virus Infections," Viruses 4(11):2806-2830, MDPI, Switzerland (Nov. 2012).
Kent, S.B.H., and Merrifield, R.B., "Preparation and Properties of Tert-butyloxycarbonylaminoacy1-4-(Oxymethyl) Phenylacetamidomethyl-(Kel F-g-styrene) Resin, an Insoluble, Noncrosslinked Support for Solid Phase Peptide Synthesis," Israel Journal of Chemistry 17(4):243-247, Wiley, United States (1978).
Kinali, M., et al., "Local Restoration of Dystrophin Expression With the Morpholino Oligomer AVI-4658 in Duchenne Muscular Dystrophy: a Single-blind, Placebo-controlled, Dose-escalation, Proof-of-concept Study," The Lancet Neurology 8(10):918-928, Lancet Pub. Group, England (Oct. 2009).
March, J., "Stereochemistry," in *Advanced Organic Chemistry*, 3rd Edition, Chapter 4, pp. 82-110, John Wiley & Sons, New York, United States (1985).
Parr, W., and Grohmann, K., "Solid-phase Peptide Synthesis on an Inorganic Matrix Having Organic Groups on the Surface," Applied Chemistry (International ed. in English) 11(4):314-315, Wiley-VCH, Germany (Apr. 1972).
Scott, R.P.W., et al., "Use of Resin Coated Glass Beads in the Form of a Packed Bed for the Solid Phase Synthesis of Peptides," Journal of Chromatographic Science 9:1-17, Oxford University Press, United Kingdom (Sep. 1971).
Stein, C.A., et al., "Eteplirsen Approved for Duchenne Muscular Dystrophy: The FDA Faces a Difficult Choice," Molecular Therapy 24(11):1884-1885, Cell Press, United States (Nov. 2016).
Summerton, J., and Weller, D., "Morpholino Antisense Oligomers: Design, Preparation, and Properties," Antisense & Nucleic Acid Drug Development 7(3):187-195, Mary Ann Liebert, Inc., United States (Jun. 1997).
Van Deutekom, J.C., et al., "Local Dystrophin Restoration with Antisense Oligonucleotide PRO051," The New England Journal of Medicine 357(26):2677-2686, Massachusetts Medical Society, United States (Dec. 2007).
Van Rietschoten, P., "Simultaneous Synthesis of Two Peptide Analogs on Different Insoluble Supports," in *Peptides* 1974, Wolman, Y., ed., pp. 113-116, Wiley and Sons, New York, United States (1975).
Wright, P., et al., "Large Scale Synthesis of Oligonucleotides via Phosphoramidite Nucleosides and a High-loaded Polystyrene Support," Tetrahedron Letters 34:3373, Elsevier, Netherlands (May 1993).
European Search Report for EP Application No. 18859106.9, dated Apr. 12, 2021, 7 pages.
Harakawa et al., "Development of an efficient method for phosphorodiamidate bond formation by using inorganic salts", *Bioorganic and Medicinal Chemistry Letters* 22(3):1445-1447 (2012).
International Search Report and Written Opinion for International Application No. PCT/US2018/052524, mailed Nov. 26, 2018, 7 pages.

* cited by examiner

Rapid, Mild Detritylation at 90°C
Collidine TFA at 90°C
1
2
1 min
30 min
120 min
6 8 10 12 14 16
Time (min)

Lutidine TFA at 90°C
1
1 min
30 min
120 min
6 8 10 12 14 16
Time (min)

Pyridine TFA at 90°C
1
1 min
30 min
120 min
6 8 10 12 14 16
Time (min)

4-Cyanopyridine TFA RT
1
2
1 min
30 min
120 min
6 8 10 12 14 16
Time (min)

PROCESSES FOR PREPARING PHOSPHORODIAMIDATE MORPHOLINO OLIGOMERS VIA FAST-FLOW SYNTHESIS

RELATED APPLICATIONS

This application claims the benefit of priority to U.S. Provisional Patent Application No. 62/562,741, filed Sep. 25, 2017, the content of which is incorporated herein by reference in its entirety.

BACKGROUND

Antisense technology provides a means for modulating the expression of one or more specific gene products, including alternative splice products, and is uniquely useful in a number of therapeutic, diagnostic, and research applications. The principle behind antisense technology is that an antisense compound, e.g., an oligonucleotide, which hybridizes to a target nucleic acid, modulates gene expression activities such as transcription, splicing or translation through any one of a number of antisense mechanisms. The sequence specificity of antisense compounds makes them attractive as tools for target validation and gene functionalization, as well as therapeutics to selectively modulate the expression of genes involved in disease.

Duchenne muscular dystrophy (DMD) is caused by a defect in the expression of the protein dystrophin. The gene encoding the protein contains 79 exons spread out over more than 2 million nucleotides of DNA. Any exonic mutation that changes the reading frame of the exon, or introduces a stop codon, or is characterized by removal of an entire out of frame exon or exons, or duplications of one or more exons, has the potential to disrupt production of functional dystrophin, resulting in DMD.

Recent clinical trials testing the safety and efficacy of splice switching oligonucleotides (SSOs) for the treatment of DMD are based on SSO technology to induce alternative splicing of pre-mRNAs by steric blockade of the spliceosome (Cirak et al., 2011; Goemans et al., 2011; Kinali et al., 2009; van Deutekom et al., 2007). However, despite these successes, the pharmacological options available for treating DMD are limited.

Eteplirsen is a phosphorodiamidate morpholino oligomer (PMO) designed to skip exon 51 of the human dystrophin gene in patients with DMD who are amendable to exon 51 skipping to restore the read frame and produce a functional shorter form of the dystrophin protein. Eteplirsen has received approval from the United States Food and Drug Administration (FDA) for treatment of DMD.

Although significant progress has been made in the field of antisense technology, there remains a need in the art for methods of preparing phosphorodiamidate morpholino oligomers with improved antisense or antigene performance.

SUMMARY

Provided herein are processes for preparing phosphorodiamidate morpholino oligomers (PMOs). The synthetic processes described herein allow for an efficient PMO synthesis using a Lewis acid catalyst while maintaining overall yield and purity of a synthesized PMO. Further provided herein is a flow-through PMO synthesis procedure.

Accordingly, in one aspect, provided herein is a process for preparing an oligomeric compound of Formula (I):

(I)

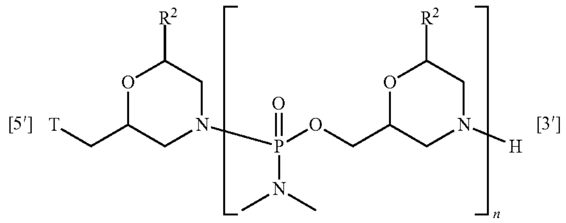

using a Lewis acid catalyst.

In another aspect, provided herein is a continuous process for preparing an oligomeric compound of Formula (A11)

(A11)

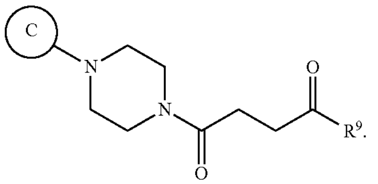

In an embodiment, the continuous process for preparing an oligomeric compound of Formula (A11) is performed in a flow-through reactor.

BRIEF DESCRIPTION OF THE FIGURES

FIG. 3 shows detritylation using.

FIG. 4 shows a complete schematic of a flow PMO synthesizer.

DETAILED DESCRIPTION

Figure 1:
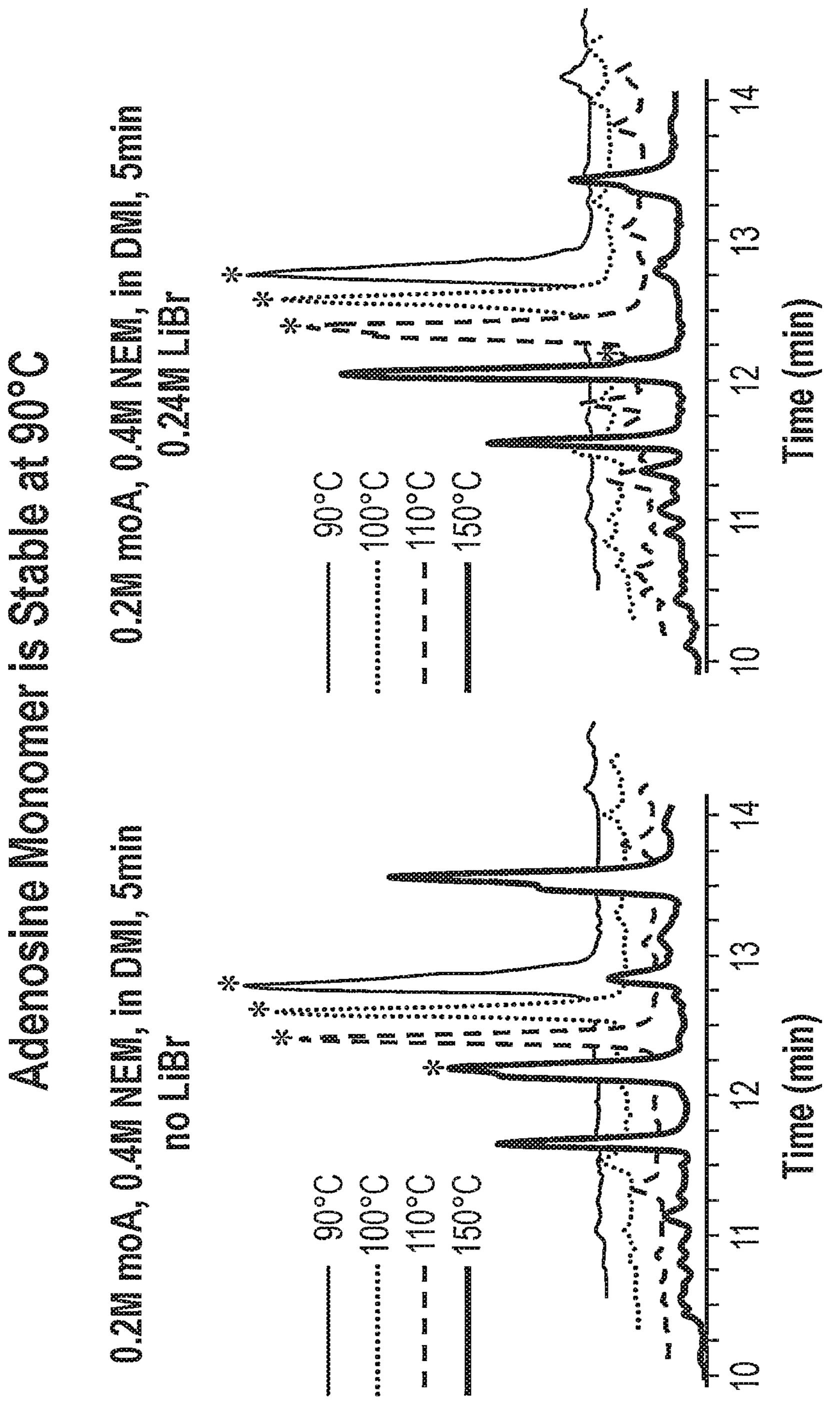
FIG. 1 shows the stability of Adenosine monomer, with or without LiBr, at 90° C., 100° C., 110° C., and 150° C.

Provided herein are processes for preparing a morpholino oligomer useful for applications toward antisense therapy. Antisense therapy is an attractive route for treating serious genetic diseases and viral infections. Antisense therapeutics are synthetic nucleobase polymers that bind to mRNA via complementary Watson-Crick base-pairing and cause alternative splicing or inhibition of translation, yielding altered proteins or reduced levels of proteins (S. Cirak, V. Arechavala-Gomeza, M. Guglieri, L. Feng, S. Torelli, K. Anthony, S. Abbs, M. E. Garralda, J. Bourke, D. J. Wells, et al., *Lancet* 2011, 378, 595-605) (J. H. Chan, S. Lim, W. F. Wong, *Clin. Exp. Pharmacol. Physiol.* 2006, 33, 533-540). In this way, critical viral proteins can be deactivated, exons with lethal frame shift mutations can be excised to yield a functional truncated protein, or oncogenic gene expression can be suppressed. Phosphorodiamidate morpholino oligomers (PMOs) are a class of antisense therapeutics in which the 5-membered ribosyl ring of RNA has been replaced with a 6-membered morpholino ring, and phosphate linkages have been replaced with uncharged phosphorodiamidates (J. Summerton, D. Weller, *Antisense Nucleic Acid Drug Dev.* 1997, 7, 187-195). These modifications make PMOs resistant to nucleases (R. M. Hudziak, E. Barofsky, D. F. Barofsky, D. L. Weller, S.-B. Huang, D. D. Weller, *Antisense Nucleic Acid Drug Dev.* 1996, 6, 267-272) and possibly more cell permeable than naked RNA (V. Arora, D. C. Knapp, M. T. Reddy, D. D. Weller, P. L. Iversen, *J. Pharm. Sci.* 2002, 91, 1009-1018). Several PMOs, including second-generation structural analogs known as PMO-X™ and peptide-PMO conjugates known as PPMOs, are currently under investigation. A first-in-class Duchenne muscular dystrophy drug, Exondys 51™ (eteplirsen), was recently approved (C. A. Stein, *Mol. Ther.* 2016, 24, 1884-1885) by the FDA, and trials are underway for the treatment of Dengue (K. L. Holden, D. A. Stein, T. C. Pierson, A. A. Ahmed, K. Clyde, P. L. Iversen, E. Harris, *Virology* 2006, 344, 439-452), Marburg (P. L. Iversen, T. K. Warren, J. B. Wells, N. L. Garza, D. V Mourich, L. S. Welch, R. G. Panchal, S. Bavari, *Viruses* 2012, 4, 2806-30), Ebola (P. L. Iversen, T. K. Warren, J. B. Wells, N. L. Garza, D. V Mourich, L. S. Welch, R. G. Panchal, S. Bavari, *Viruses* 2012, 4, 2806-30), and influenza viral infections (Q. Ge, M. Pastey, D. Kobasa, P. Puthavathana, C. Lupfer, R. K. Bestwick, P. L. Iversen, J. Chen, D. A. Stein, Antimicrob. Agents Chemother. 2006, 50, 3724-33). Despite the breadth of potential disease targets, lengthy preparation of PMOs limits their exploration and application. To alleviate this problem, and enable efficient identification and production of these compositions, provided herein is an efficient PMO synthesis using a Lewis acid, as well as a flow-through PMO synthesis procedure.

Definitions

Listed below are definitions of various terms used to describe this disclosure. These definitions apply to the terms as they are used throughout this specification and claims, unless otherwise limited in specific instances, either individually or as part of a larger group.

"Base-protected" or "base protection" refers to protection of the base-pairing groups, e.g., purine or pyrimidine bases, on the morpholino subunits with protecting groups suitable to prevent reaction or interference of the base-pairing groups during stepWise oligomer synthesis. (An example of a base-protected morpholino subunit is the activated C subunit Compound (C) having a CBZ protecting group on the cytosine amino group depicted below.) An "activated phosphoramidate group" is typically a chlorophosphoramidate group, having substitution at nitrogen which is desired in the eventual phosphorodiamidate linkage in the oligomer. An example is (dimethylamino)chlorophosphoramidate, i.e., —O—P(═O)(NMe2)Cl.

The term "support-bound" refers to a chemical entity that is covalently linked to a support-medium.

The term "support-medium" refers to any material including, for example, any particle, bead, or surface, upon which an oligomer can be attached or synthesized upon, or can be modified for attachment or synthesis of an oligomer. Representative substrates include, but are not limited to, inorganic supports and organic supports such as glass and modified or functionalized glass, plastics (including acrylics, polystyrene and copolymers of styrene and other materials, polypropylene, polyethylene, polybutylene, polyurethanes, TEFLON, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Particularly useful support-medium and solid surfaces for some embodiments are located within a flow-through reactor. In some embodiments of the processes described herein, the support-medium comprises polystyrene with 1% crosslinked divinylbenzene.

In some embodiments, representative support-mediums comprise at least one reactive site for attachment or synthesis of an oligomer. For example, in some embodiments, a support-medium of the disclosure comprises one or more terminal amino or hydroxyl groups capable of forming a chemical bond with an incoming subunit or other activated group for attaching or synthesizing an oligomer.

Some representative support-mediums that are amenable to the processes described herein include, but are not limited to, the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, *Angew. Chem. Internal. Ed.* 1972, 11, 314, sold under the trademark "PORASIL E" by Waters Associates, Framingham, Mass., USA); a mono ester of 1,4-dihydroxymethylbenzene and silica (see Bayer and Jung, *Tetrahedron Lett.,* 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix, or POROS, a copolymer of polystyrene/divinylbenzene (available from Perceptive Biosystems); soluble support-medium such as polyethylene glycol PEG's (see Bonora et al., Organic Process Research & Development, 2000, 4, 225-231); PEPS support, which is a polyethylene (PE) film with pendant long-chain polystyrene (PS) grafts (see Berg, et al., *J. Am. Chem. Soc.,* 1989, 111, 8024 and International Patent Application WO 1990/02749); copolymers of dimethylacrylamide cross-linked with N,N'-bisacryloylethylenediamine, including a known amount of N-tertbutoxycarbonyl-beta-alanyl-N'-acryloylhexamethylenediamine (see Atherton, et al., *J. Am. Chem. Soc.,* 1975, 97, 6584, Bioorg. Chem. 1979, 8, 351, and J. C. S. Perkin I 538 (1981)); glass particles coated with a hydrophobic cross-linked styrene polymer (see Scott, et al., *J. Chrom. Sci.,* 1971, 9, 577); fluorinated ethylene polymer onto which has been grafted polystyrene (see Kent and Merrifield, *Israel J. Chem.* 1978, 17, 243 and van Rietschoten in *Peptides* 1974, *Y. Wolman, Ed.*, Wiley and Sons, New York, 1975, pp. 113-116); hydroxypropylacrylate-coated polypropylene membranes (Daniels, et al., *Tetrahedron Lett.* 1989, 4345); acrylic acid-grafted polyethylene-rods (Geysen, et al., *Proc. Natl. Acad. Sci. USA,* 1984, 81, 3998); a "tea bag" containing traditionally-used polymer beads (Houghten, *Proc. Natl. Acad. Sci. USA,* 1985, 82, 5131); and combinations thereof.

The term "flow-through reactor" refers to a chamber comprising a surface (e.g., solid surface) across which one or more fluid reagents (e.g., liquid or gas) can be flowed. In an embodiment, the chamber can be, but is not limited to, a junction mixer, a mixing vessel, a coil reactor, a tube reactor, a spinning disk reactor, a spinning tube reactor, a multi-cell flow reactor, an oscillatory flow reactor, or a microreactor. In a further embodiment, the chamber contains a solid-supported chemical reactant. In a particular embodiment, the solid-supported chemical reactant is confined within the chamber by a filter.

The term "deblocking agent" refers to a composition (e.g., a solution) comprising a chemical acid or combination of chemical acids for removing protecting groups. Exemplary chemical acids used in deblocking agents include halogenated acids, e.g., chloroacetic acid, dichloroacetic acid, trichloroacetic acid, fluoro acetic acid, difluoroacetic acid, and trifluoroacetic acid. In some embodiments, a deblocking agent removes one or more trityl groups from, for example, an oligomer, a support-bound oligomer, a support-bound subunit, or other protected nitrogen or oxygen moiety.

The terms "halogen" and "halo" refer to an atom selected from the group consisting of fluorine, chlorine, bromine, and iodine.

The term "capping agent" refers to a composition (e.g., a solution) comprising an acid anhydride (e.g., benzoic anhydride, acetic anhydride, phenoxyacetic anhydride, and the like) useful for blocking a reactive cite of, for example, a support-medium forming a chemical bond with an incoming subunit or other activated group.

The term "cleavage agent" refers to a composition (e.g., a liquid solution or gaseous mixture) comprising a chemical base (e.g., ammonia or 1,8-diazabicycloundec-7-ene) or a combination of chemical bases useful for cleaving, for example, a support-bound oligomer from a support-medium.

The term "deprotecting agent" refers to a composition (e.g., a liquid solution or gaseous mixture) comprising a chemical base (e.g., ammonia, 1,8-diazabicycloundec-7-ene or potassium carbonate) or a combination of chemical bases useful for removing protecting groups. For example, a deprotecting agent, in some embodiments, can remove the base protection from, for example, a morpholino subunit, morpholino subunits of a morpholino oligomer, or support-bound versions thereof.

The term "solvent" refers to a component of a solution or mixture in which a solute is dissolved. Solvents may be inorganic or organic (e.g., acetic acid, acetone, acetonitrile, acetyl acetone, 2-aminoethanol, aniline, anisole, benzene, benzonitrile, benzyl alcohol, 1-butanol, 2-butanol, i-butanol, 2-butanone, t-butyl alcohol, carbon disulfide, carbon tetrachloride, chlorobenzene, chloroform, cyclohexane, cyclohexanol, cyclohexanone, di-n-butylphthalate, 1,1-dichloroethane, 1,2-dichloroethane, diethylamine, diethylene glycol, diglyme, dimethoxyethane (glyme), N,N-dimethylaniline, dimethylformamide, dimethylphthalate, dimethylsulfoxide, dioxane, ethanol, ether, ethyl acetate, ethyl acetoacetate, ethyl benzoate, ethylene glycol, glycerin, heptane, 1-heptanol, hexane, 1-hexanol, methanol, methyl acetate, methyl t-butyl ether, methylene chloride, 1-octanol, pentane, 1-pentanol, 2-pentanol, 3-pentanol, 2-pentanone, 3-pentanone, 1-propanol, 2-propanol, pyridine, tetrahydrofuran, toluene, water, p-xylene).

The phrases "morpholino oligomer" and "phosphorodiamidate morpholino oligomer" or "PMO" refers to an oligomer having morpholino subunits linked together by phosphorodiamidate linkages, joining the morpholino nitrogen of one subunit to the 5'-exocyclic carbon of an adjacent subunit. Each morpholino subunit comprises a nucleobase-pairing moiety effective to bind, by nucleobase-specific hydrogen bonding, to a nucleobase in a target.

The term "EG3 tail" refers to triethylene glycol moieties conjugated to the oligomer, e.g., at its 3'- or 5'-end. For example, in some embodiments, "EG3 tail" conjugated to the 3' end of an oligomer can be of the structure:

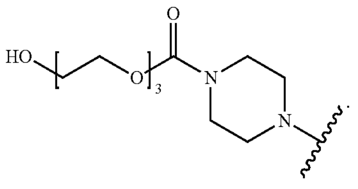

The terms "about" or "approximately" are generally understood by persons knowledgeable in the relevant subject area, but in certain circumstances can mean within ±10%, or within ±5%, of a given value or range.

Processes for Preparing Morpholino Oligomers in a Batch-Wise or Fast-Flow Procedure Provided herein is an efficient PMO synthesis using a Lewis acid. Also provided herein is a flow-through PMO synthesis procedure (also referred to herein as a "continuous synthesis" or "fast-flow synthesis").

Synthesis is generally conducted, as described herein, on a support-medium. In an embodiment, provided herein is a first synthon (e.g. a monomer, such as a morpholino subunit) that is first attached to a support-medium, and the oligomer is then synthesized by sequentially coupling subunits to the support-bound synthon in the presence of a Lewis acid catalyst. This iterative elongation eventually results in a final oligomeric compound. This process can be done via a fast-flow synthesis, which is described herein. The advantages of fast-flow are faster reactions, quick optimization, cleaner products, easy scale-up, safer reactions, and the integration of typically separate processes.

Suitable support-media can be soluble or insoluble, or may possess variable solubility in different solvents to allow the growing support-bound polymer to be either in or out of solution as desired. Traditional support-media are for the most part insoluble and are routinely placed in reaction vessels while reagents and solvents react with and/or wash the growing chain until the oligomer has reached the target length, after which it is cleaved from the support, and, if necessary, further worked up to produce the final polymeric compound. More recent approaches have introduced soluble supports including soluble polymer supports to allow precipitating and dissolving the iteratively synthesized product at desired points in the synthesis (Gravert et al., Chem. Rev., 1997, 97, 489-510).

Also provided herein are processes for preparing morpholino oligomers.

Accordingly, in one aspect, provided herein is a process for preparing an oligomeric compound of Formula (I):

(I)

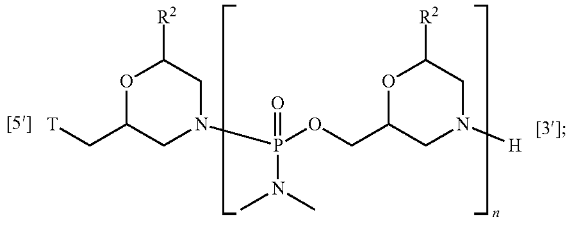

wherein n is an integer from 9 to 39;

T is OH

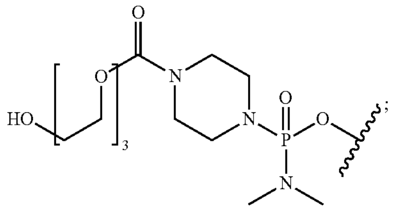

and each $R^2$ is, independently for each occurrence, selected from the group consisting of:

(C)

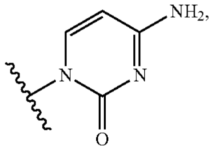

(G)

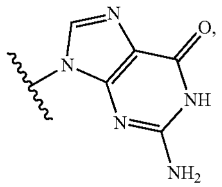

(T)

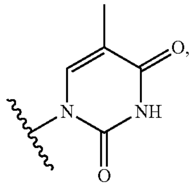

(A)

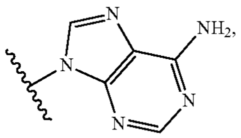

(5mC)

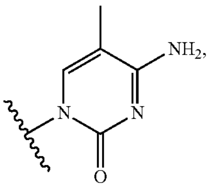

(U)

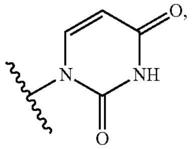

and

-continued (I)

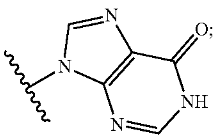

wherein the process comprises the sequential steps of:

(a) contacting a compound of Formula (A1):

(A1)

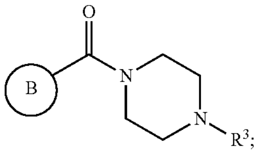

wherein

B is

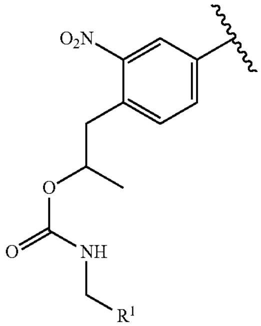

or

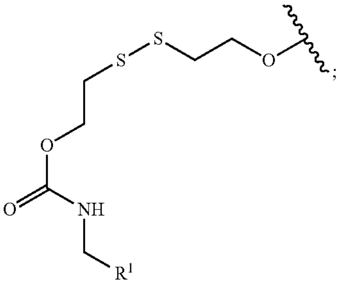

$R^1$ is a support-medium; and $R^3$ is selected from the group consisting of trityl, monomethoxytrityl, dimethoxytrityl and trimethoxytrityl;

with a deblocking agent to form the compound of Formula (II):

(II)

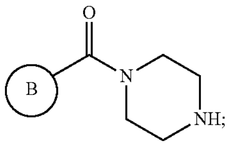

wherein B is
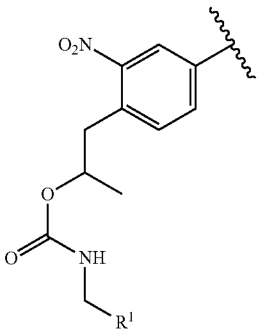
or
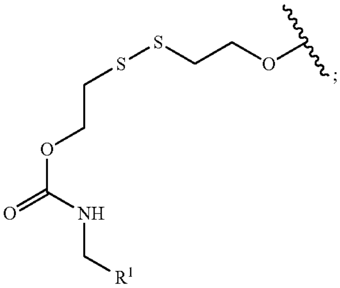
and
$R^1$ is a support-medium;
(b) contacting the compound of Formula (II) with a compound of Formula (A2):
(A2)
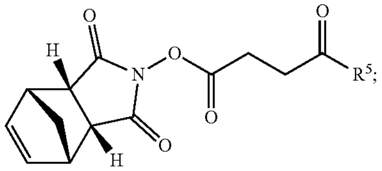
wherein $R^5$ is
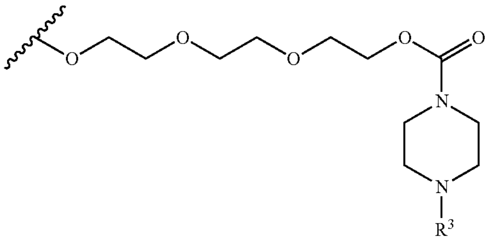
or
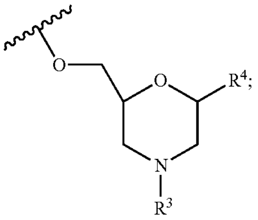
$R^3$ is selected from the group consisting of trityl, monomethoxytrityl, dimethoxytrityl and trimethoxytrityl; and
$R^4$ is selected from the group consisting of:
(PC)
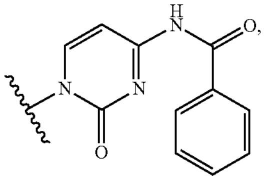
(DPG)
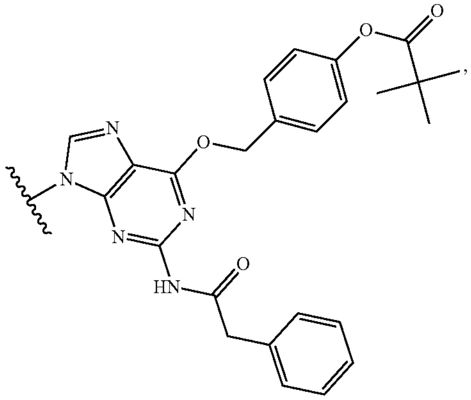
(T)
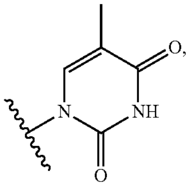
(PA)
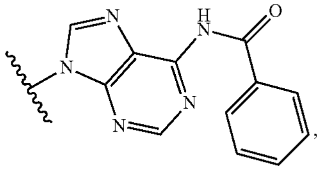
(P5mC)
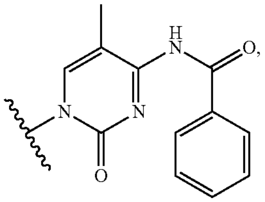
(U)
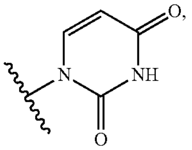
(I)
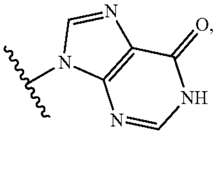
and -continued
(PG)
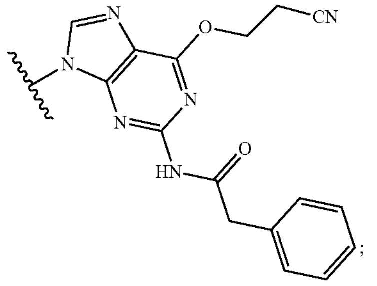
to form a compound of Formula (A3):
(A3)
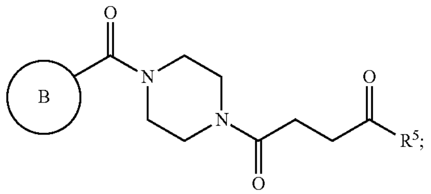
wherein
B is
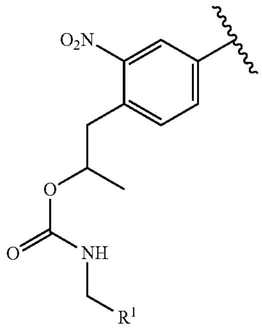
or
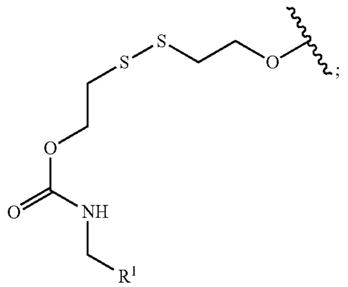
$R^1$ is a support-medium;
$R^5$ is
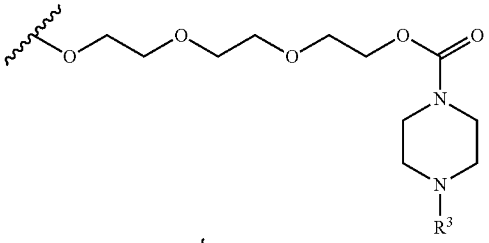
or
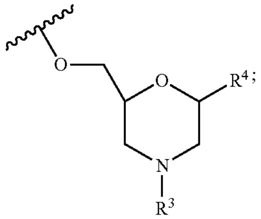
$R^3$ is selected from the group consisting of trityl, monomethoxytrityl, dimethoxytrityl and trimethoxytrityl; and
$R^4$ is selected from the group consisting of:
(PC)
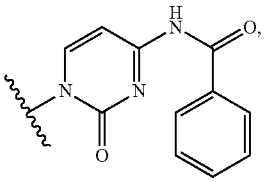
(DPG)
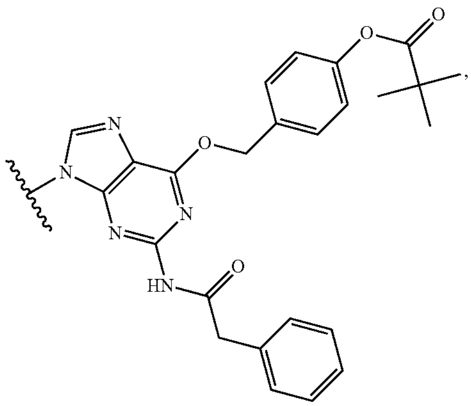
(T)
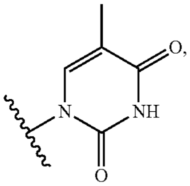
(PA)
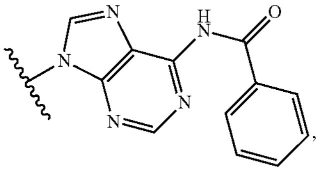

-continued
(P5mC)
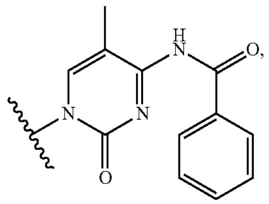
(U)
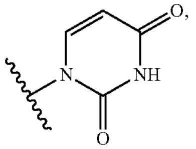
(I)
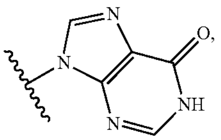
and
(PG)
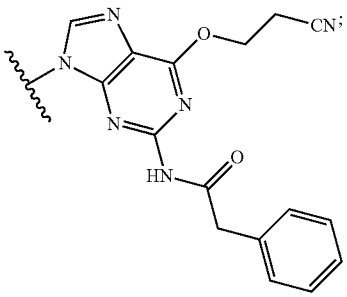
(c) contacting the compound of Formula (A3) with a deblocking agent to form a compound of Formula (IV):
(IV)
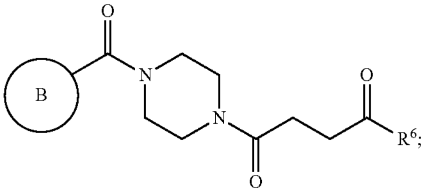
wherein B is
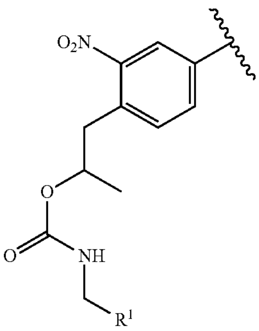
or
-continued
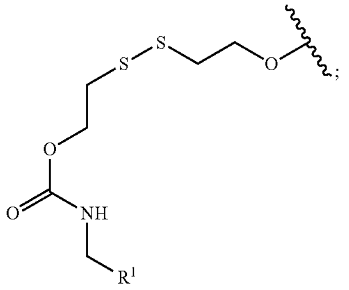
$R^1$ is a support-medium;
$R^6$ is
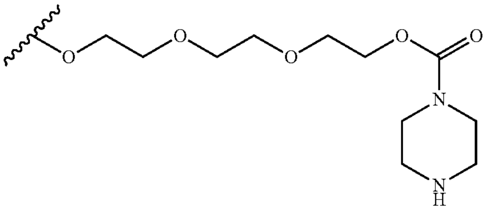
or
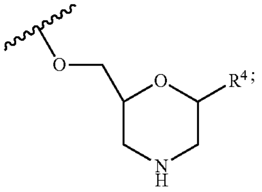
and
$R^4$ is selected from the group consisting of:
(PC)
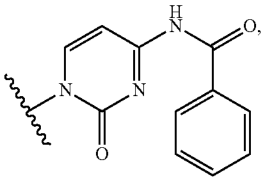
(DPG)
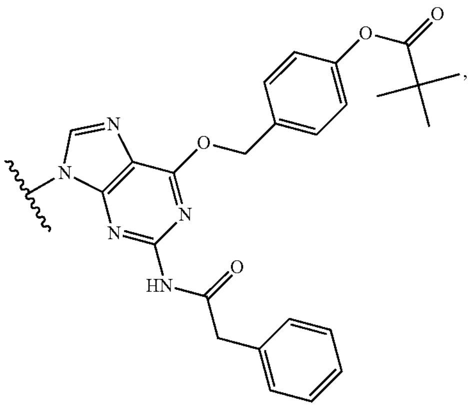

-continued
(T)
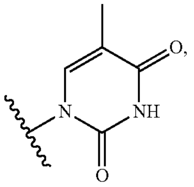
(PA)
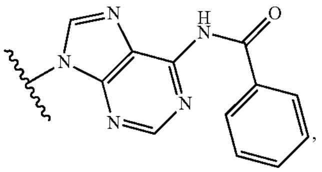
(P5mC)
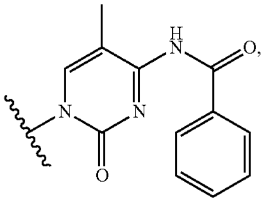
(U)
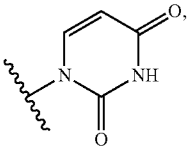
(I)
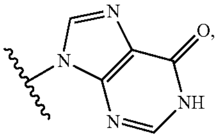
and
(PG)
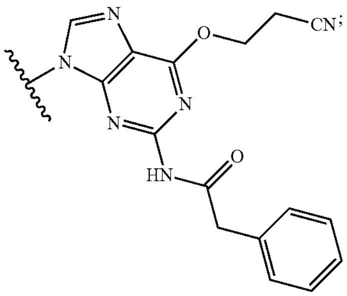
(d) contacting the compound of Formula (IV) with a compound of Formula (A4):
(A4)
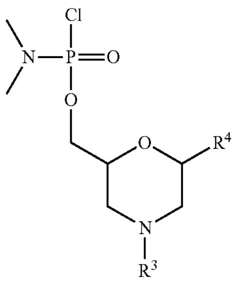
in the presence of a Lewis acid catalyst;
wherein
$R^3$ is selected from the group consisting of trityl, monomethoxytrityl, dimethoxytrityl and trimethoxytrityl; and
$R^4$ is selected from the group consisting of:
(PC)
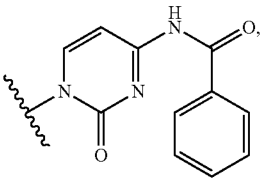
(DPG)
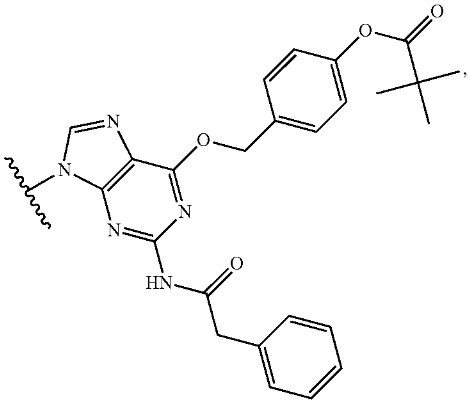
(T)
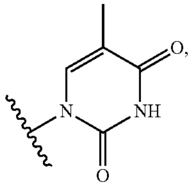
(PA)
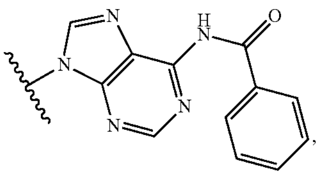
(P5mC)
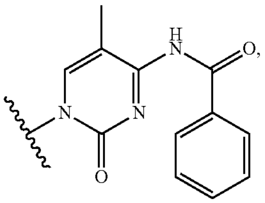
(U)
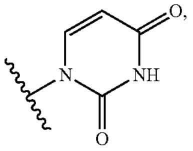

-continued
(I)
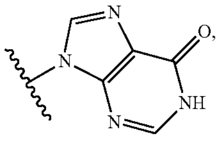
and
(PG)
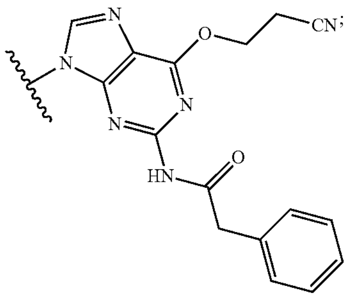
to form a compound of Formula (A5):
(A5)
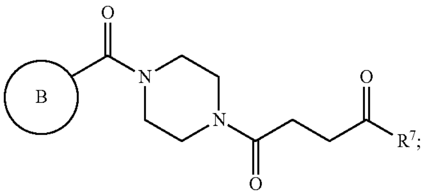
wherein $R^7$ is of Formula (A5a) or Formula (A5b):
(A5a)
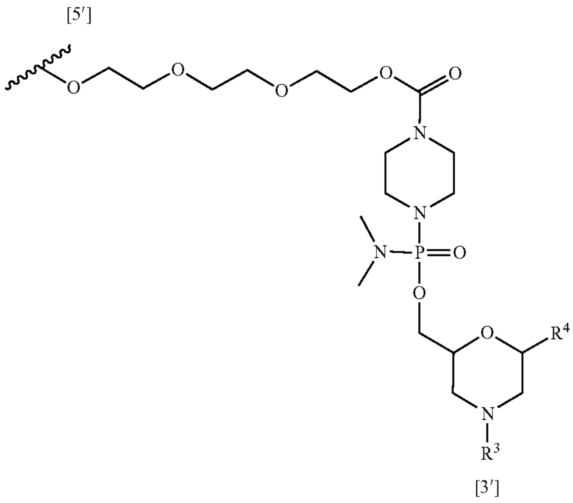
or
-continued
(A5b)
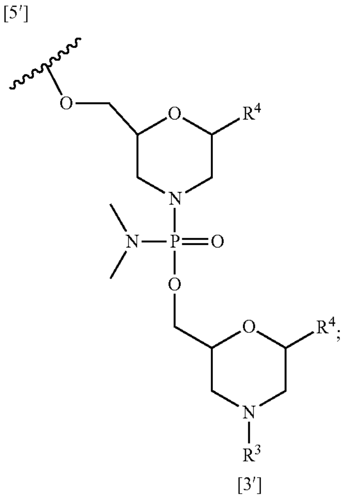
B is
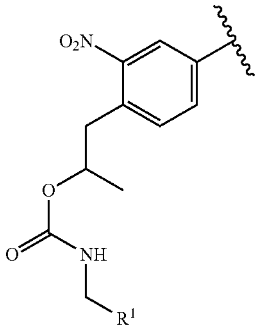
or
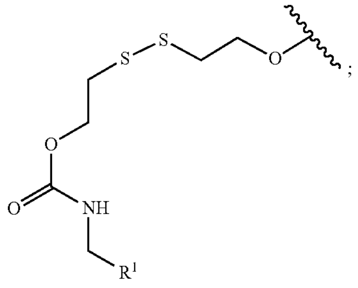
$R^1$ is a support-medium;
$R^3$ is selected from the group consisting of trityl, monomethoxytrityl, dimethoxytrityl and trimethoxytrityl; and
$R^4$ is selected from:
(PC)
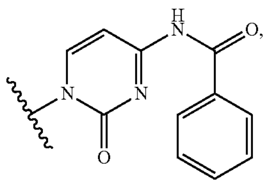

-continued (DPG)

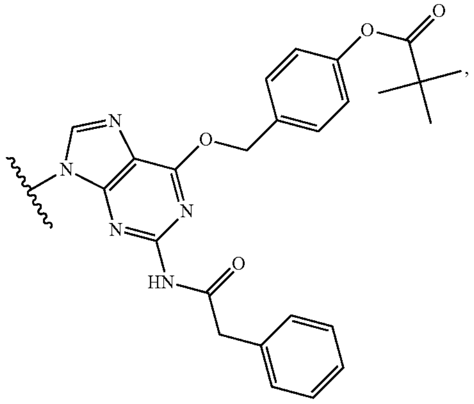

(T)

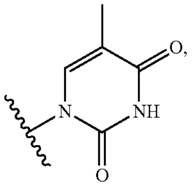

(PA)

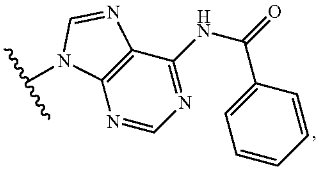

(P5mC)

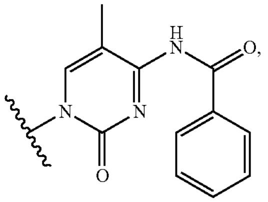

(U)

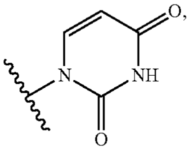

(I)

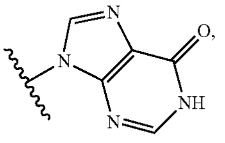

and (PG)

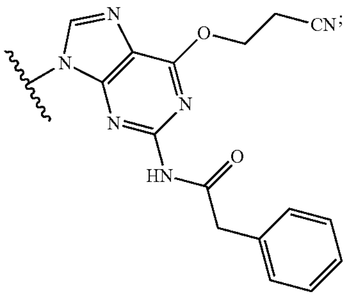

(e) performing Y iterations of the sequential steps of:

(e1) contacting the product formed by the immediately prior step with a deblocking agent; and (e2) contacting the compound formed by the immediately prior step with a compound of Formula (A8):

(A8)

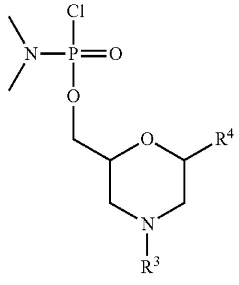

in the presence of a Lewis acid catalyst;

wherein

Y is n−1 if $R^7$ is of the Formula (A5a) or Y is n−2 if $R^7$ is of the Formula (A5b);

$R^3$ is selected from the group consisting of trityl, monomethoxytrityl, dimethoxytrityl and trimethoxytrityl; and $R^4$ is, independently for each compound of Formula (A8), selected from the group consisting of:

(PC)

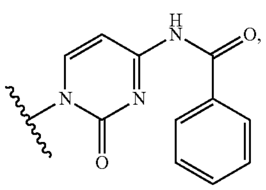

(DPG)

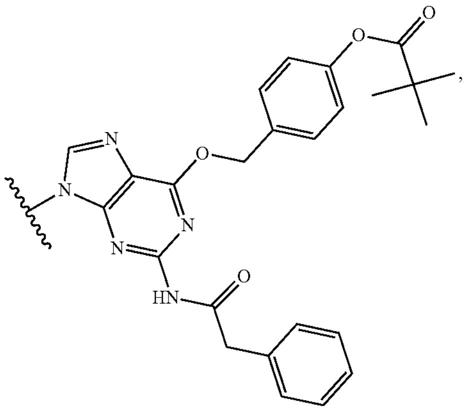

(T)

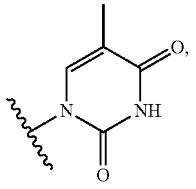

-continued
(PA)
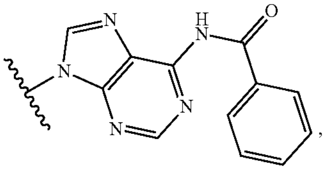
(P5mC)
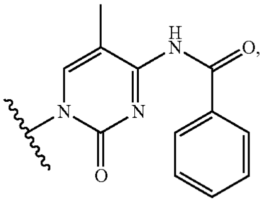
(U)
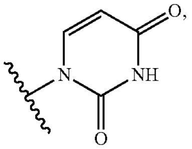
(I)
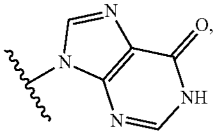 and
(PG)
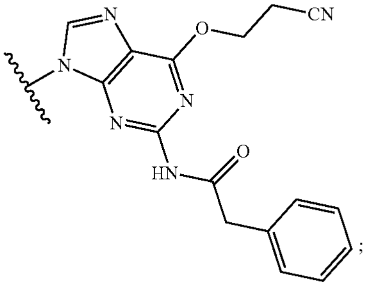
to form a compound of Formula (A9):
(A9)
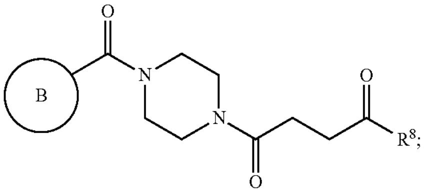
wherein $R^8$ is
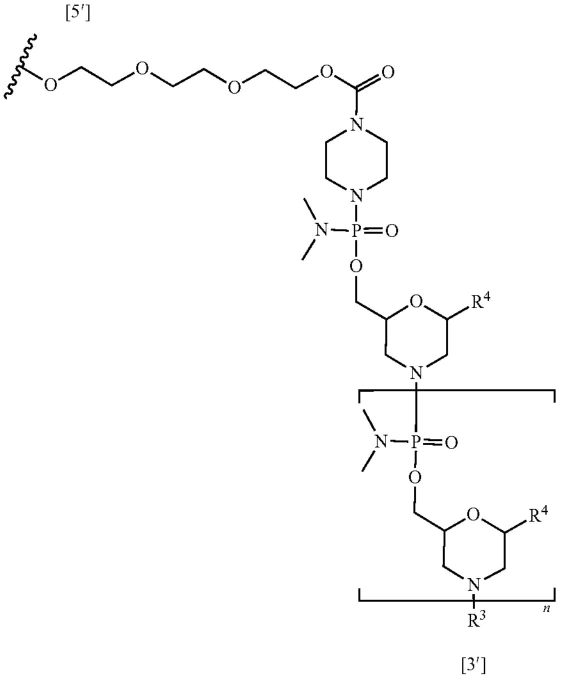
or
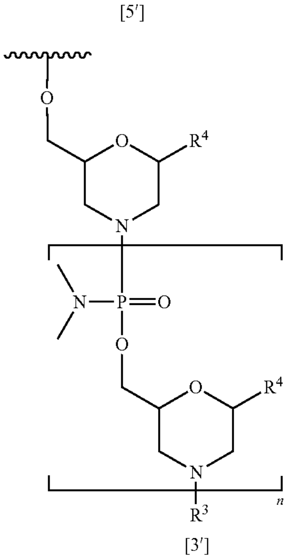
;
B is
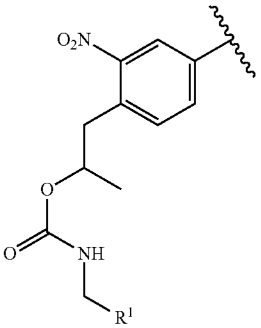
or -continued

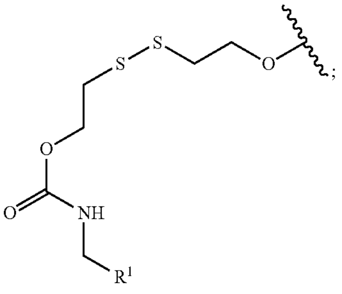

n is an integer from 9 to 39;

$R^1$ is a support-medium;

$R^3$ is selected from the group consisting of trityl, monomethoxytrityl, dimethoxytrityl and trimethoxytrityl; and $R^4$ is, independently for each occurrence, selected from the group consisting of:

(PC)

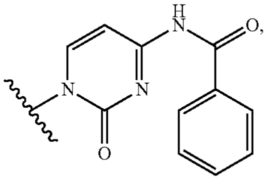

(DPG)

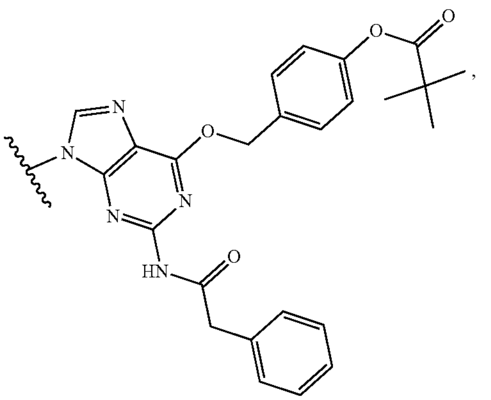

(T)

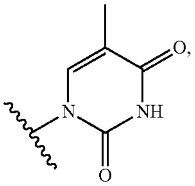

(PA)

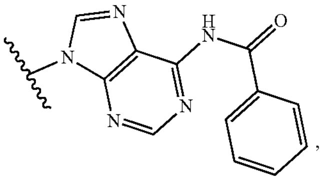

-continued (P5mC)

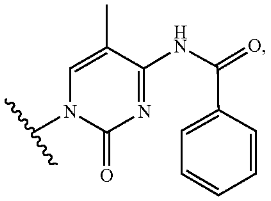

(U)

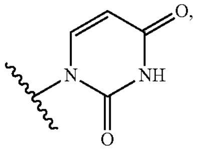

(I)

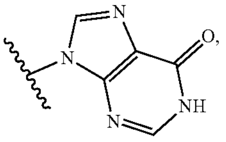

and (PG)

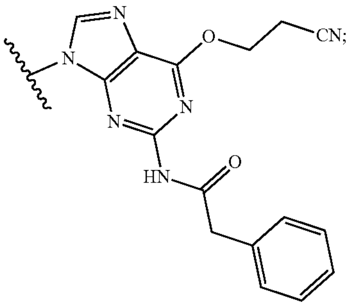

and (f) contacting the compound of Formula (A9) with a deblocking agent to form a compound of Formula (A10):

(A10)

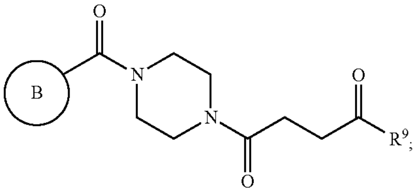

wherein $R^9$ is
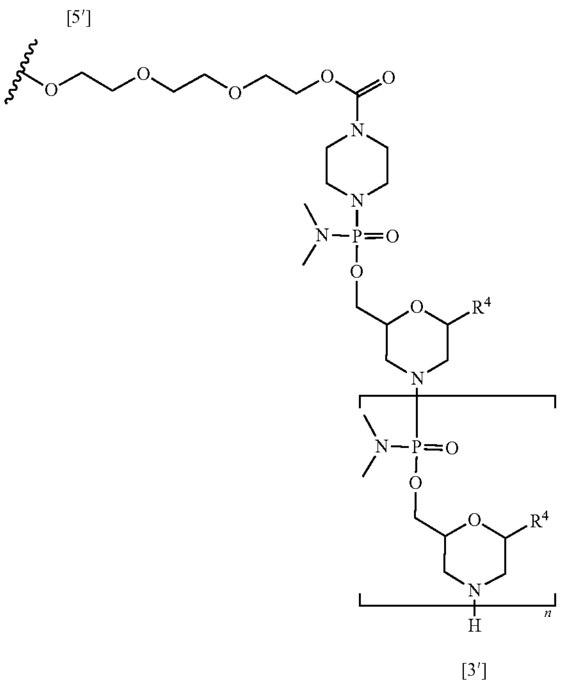
or
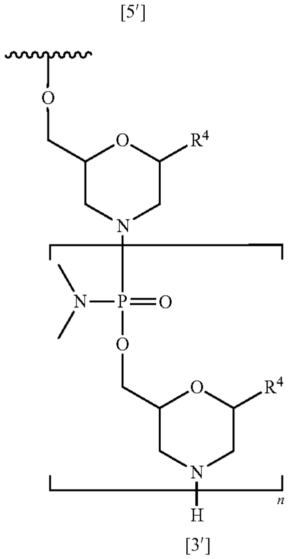
;
B is
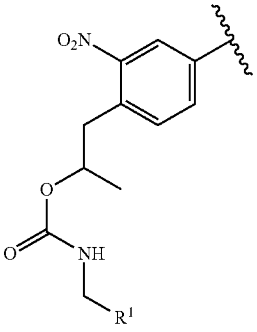
or
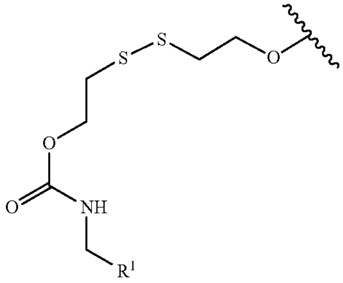
;
n is an integer from 9 to 39;
$R^1$ is a support-medium; and
$R^4$ is, independently for each occurrence, selected from the group consisting of:
(PC)
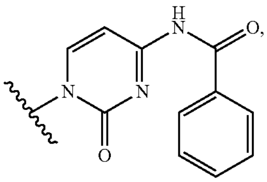
(DPG)
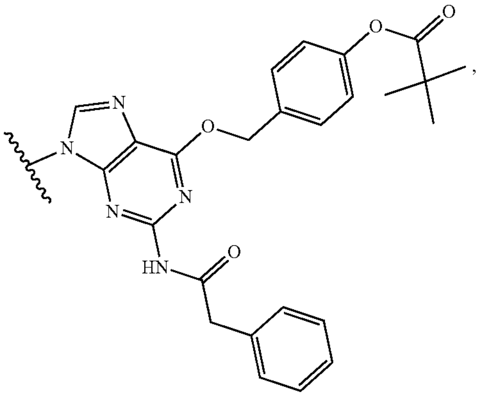
(T)
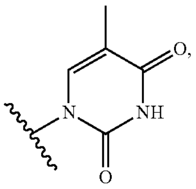

-continued
(PA)
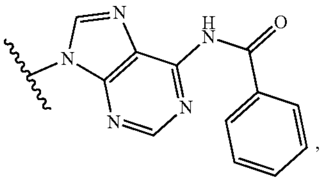
(P5mC)
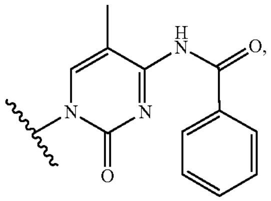
(U)
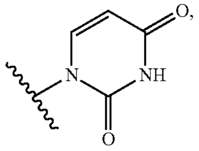
(I)
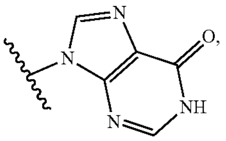
and
(PG)
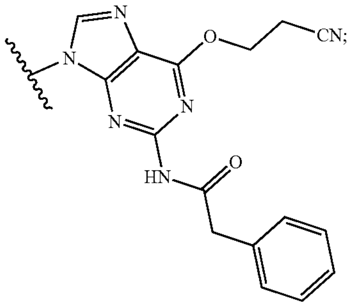
(g) contacting the compound of Formula (A10) with a cleaving agent to form a compound of Formula (A11):
(A11)
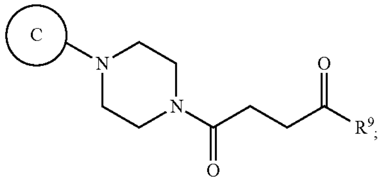
wherein
$R^9$ is
[5′]
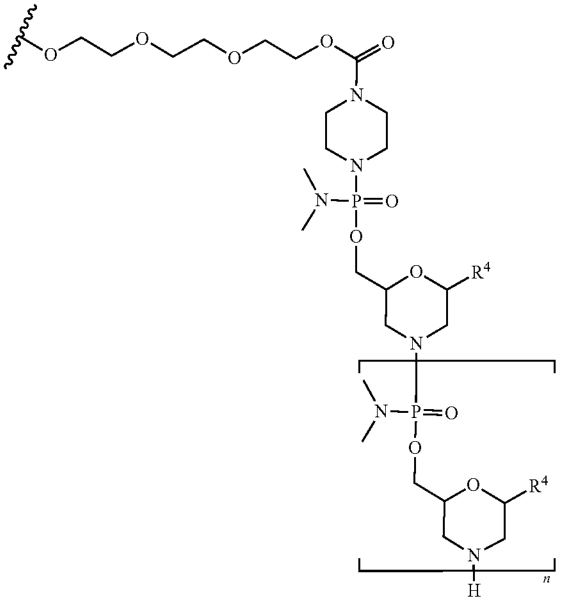
[3′]
or
[5′]
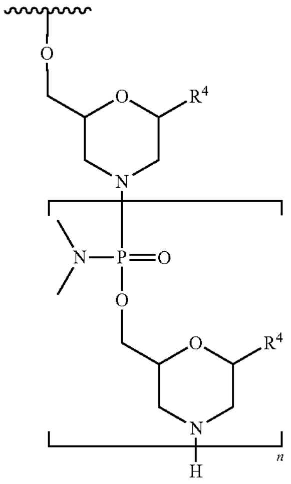
[3′]
;
C is
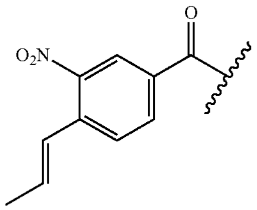 [SMILES: *C(=O)c1ccc(/C=C/C)c([N+](=O)[O-])c1]
or H;
n is an integer from 9 to 39; and $R^4$ is, independently for each occurrence, selected from the group consisting of:

(PC)

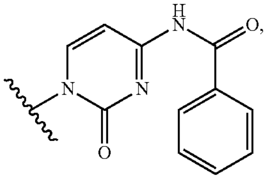

(DPG)

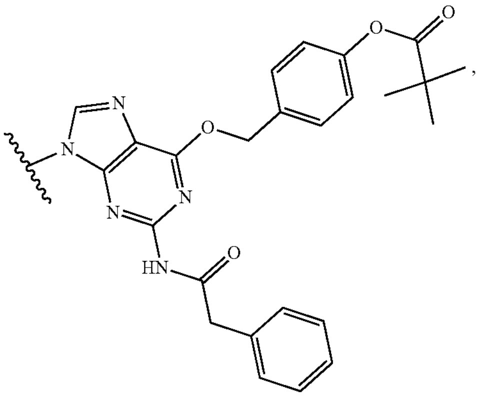

(T)

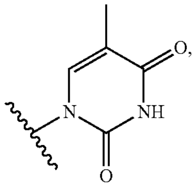

(PA)

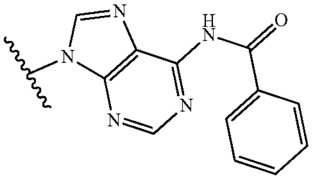

, (P5mC)

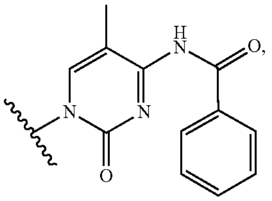

(U)

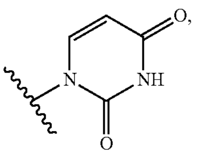

-continued (I)

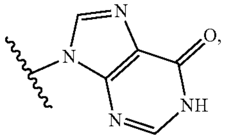

and (PG)

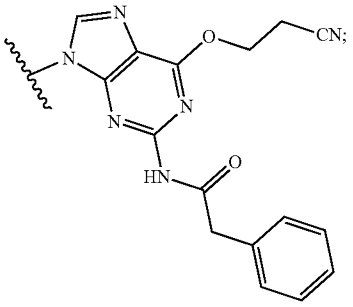

and (h) contacting the compound of Formula (A11) with a deprotecting agent to form the oligomeric compound of Formula (I).

In an embodiment, one of steps (d) or (e2) further comprises contacting the compound formed by the immediately prior step with a capping agent.

In another embodiment, at least one of steps (a), (c), (e1), or (f) further comprises contacting the deblocked compound with a neutralization agent.

In yet another embodiment, steps (a), (c), (e1), and (f) further comprise contacting the deblocked compound of each step with a neutralization agent.

In another embodiment, the deblocking step is run between room temperature and 110° C.

In yet another embodiment, the deblocking step is run between 50° C. and 100° C.

In a particular embodiment, the deblocking step is run between 70° C. and 90° C.

In an embodiment, the capping agent is in a solution comprising N-ethylmorpholine and methylpyrrolidinone.

In another embodiment, the capping agent is an acid anhydride.

In a particular embodiment, the capping agent is benzoic anhydride.

In an embodiment, the compounds of Formula (A4) and Formula (A8) are each, independently, in a solution comprising N-ethylmorpholine and dimethylimidazolidinone.

In another embodiment, the cleavage agent comprises dithiothreitol and 1,8-diazabicyclo[5.4.0]undec-7-ene.

In yet another embodiment, the cleavage agent is in a solution comprising N-methyl-2-pyrrolidone.

In another embodiment, the deprotecting agent comprises $NH_3$.

In a further embodiment, the deprotecting agent is in an aqueous solution.

In an embodiment, the support-medium comprises polystyrene with 1% crosslinked divinylbenzene.

In an embodiment in steps (a)-(g), B is

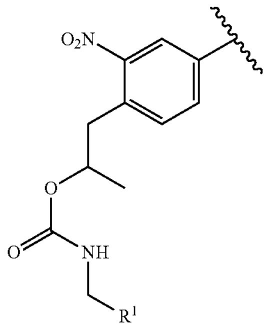

and step (h), C is

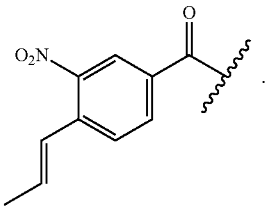 [SMILES: *C(=O)c1ccc(/C=C/C)c([N+](=O)[O-])c1]

In another embodiment, the process is carried out in a batchwise synthesis or in a continuous synthesis.

In yet another embodiment, any of steps (a), (b), (c), (d), (e1), (e2), (f), (g), or (h) are carried out in a batchwise synthesis or in a continuous synthesis.

In a particular embodiment, steps (a), (b), (g), and (h) are carried out in a batchwise synthesis and steps (c), (d), (e1), (e2), and (f) are carried out in a continuous synthesis.

In an embodiment, the deblocking agent used in each step is a solution comprising a halogenated acid.

In another embodiment, the deblocking agent is selected from the group consisting of chloroacetic acid, dichloroacetic acid, trichloroacetic acid, fluoroacetic acid, difluoroacetic acid, and trifluoroacetic acid.

In a particular embodiment, the deblocking agent is trifluoroacetic acid.

In an embodiment, the Lewis acid is soluble in the coupling solvent.

In another embodiment, the Lewis acid is selected from a group consisting of LiCl, LiBr, LiI, and LiOTf.

In a particular embodiment, the Lewis acid is LiBr.

In an embodiment, the neutralization agent is in a solution comprising a halogenated solvent and isopropyl alcohol.

In another embodiment, the halogenated solvent is dichloromethane or dichloroethane.

In yet another embodiment, the neutralization agent is a monoalkyl, dialkyl, or trialkyl amine.

In another embodiment, the neutralization agent is N,N-diisopropylethylamine.

In another embodiment, the neutralization agent is N-ethylmorpholine.

In an embodiment, the deblocking agent used in each step is a solution comprising 4-cyanopyridine, dichloromethane, trifluoroacetic acid, trifluoroethanol, and water.

In an embodiment, the deblocking agent used in each step is a solution comprising 4-cyanopyridine, dichloroethane, trifluoroacetic acid, trifluoroethanol, and water.

In an embodiment, the deblocking agent used in each step is a solution comprising 3,5-dimethylpyridine, dichloromethane, trifluoroacetic acid, trifluoroethanol, and water.

In an embodiment, the deblocking agent used in each step is a solution comprising 3,5-dimethylpyridine, dichloroethane, trifluoroacetic acid, trifluoroethanol, and water.

A Continuous Processes for Preparing Morpholino Oligomers

Provided herein is a continuous (flow-through) process for preparing morpholino oligomers.

Accordingly, in an aspect, provided herein is a continuous process for preparing an oligomeric compound of Formula (A11):

(A11)

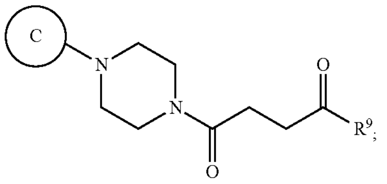

wherein $R^9$ is
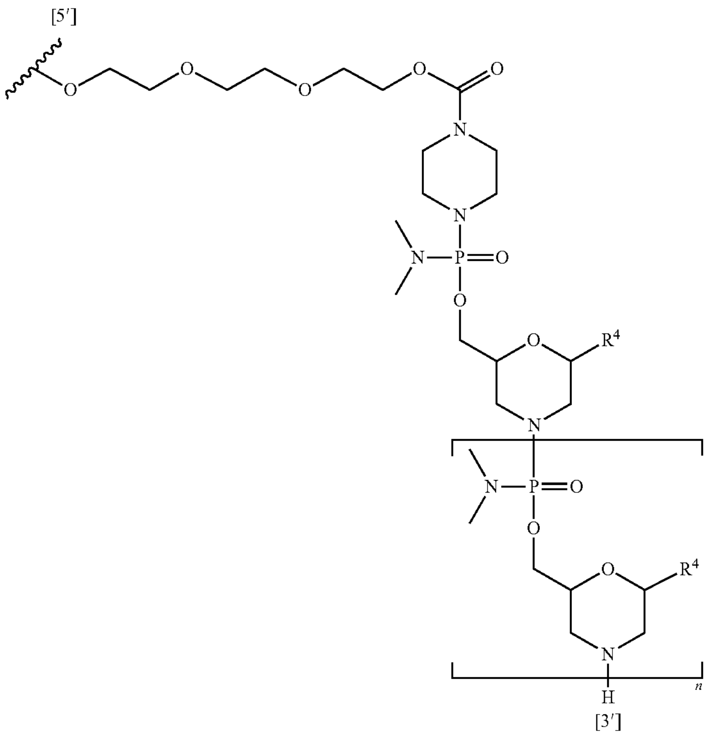
or
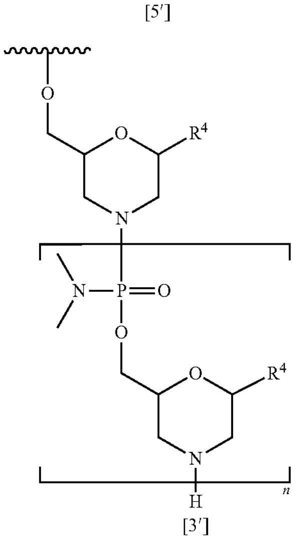
C is
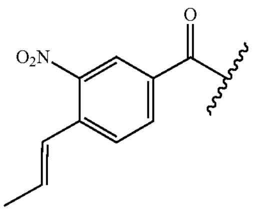 [SMILES: *C(=O)c1ccc(/C=C/C)c([N+](=O)[O-])c1]
or H;
n is an integer from 9 to 39; and
$R^4$ is, independently for each occurrence, selected from the group consisting of:
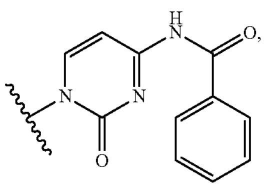
(PC)

-continued
(DPG)
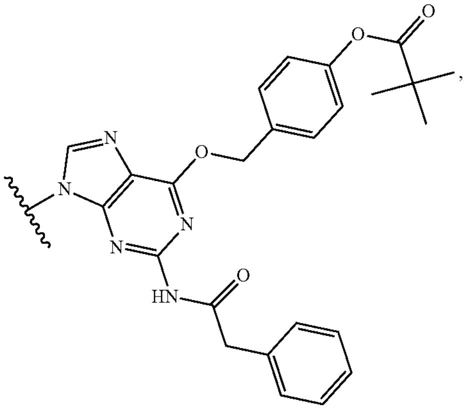
(T)
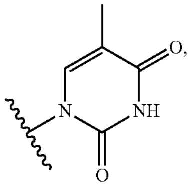
(PA)
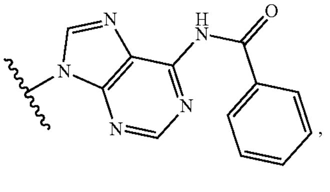
(P5mC)
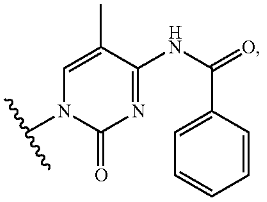
(U)
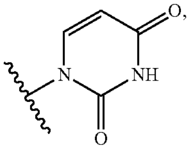
(I)
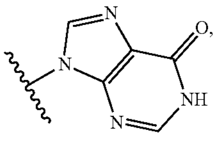
and
(PG)
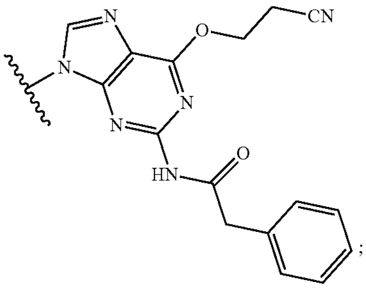
wherein the process comprises the sequential steps of:
(a) contacting a deblocking agent with a compound of Formula (A3):
(A3)
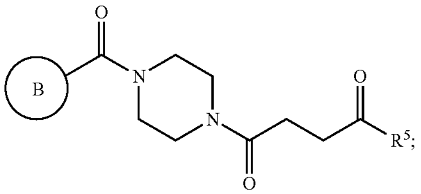
wherein B is
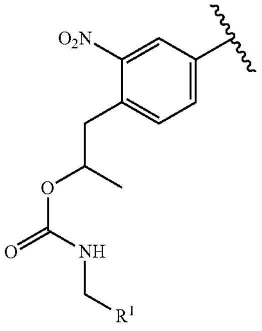
or
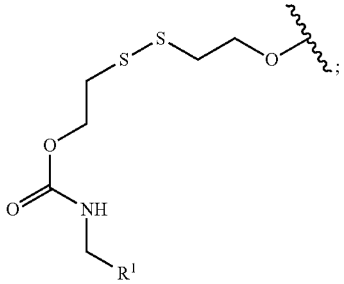
$R^1$ is a support-medium;
$R^3$ is selected from the group consisting of trityl, monomethoxytrityl, dimethoxytrityl and trimethoxytrityl;
$R^5$ is
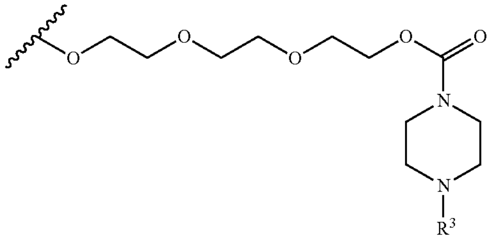
or
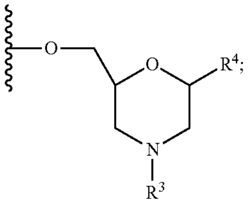

$R^3$ is selected from the group consisting of trityl, monomethoxytrityl, dimethoxytrityl and trimethoxytrityl; and
$R^4$ is selected from the group consisting of:
(PC)
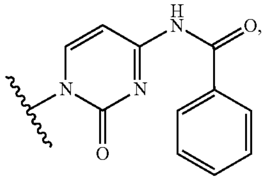
(DPG)
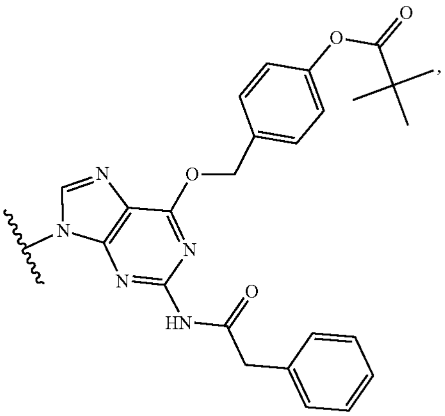
(T)
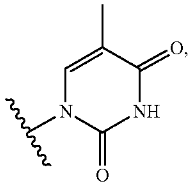
(PA)
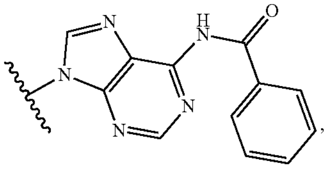
(P5mC)
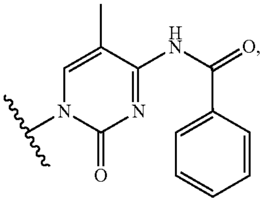
(U)
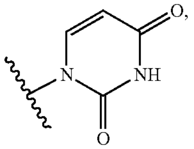
(I)
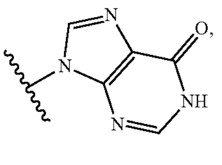
and
-continued
(PG)
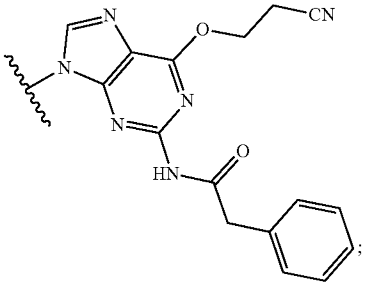
in a reactor vessel to form a compound of Formula (IV):
(IV)
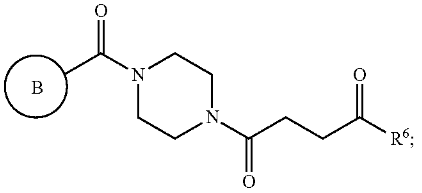
wherein B is
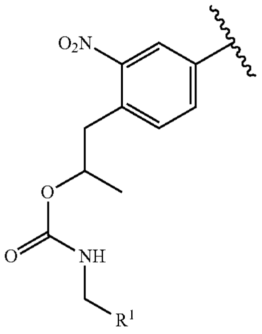
or
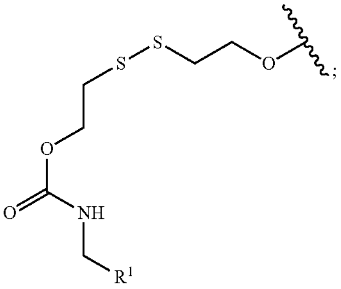
$R^1$ is a support-medium;
$R^6$ is
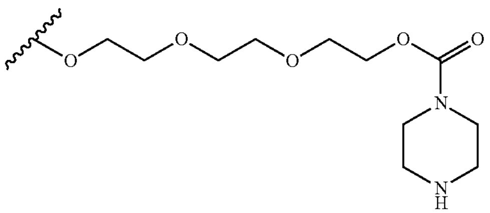
or -continued

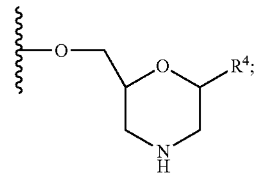

and $R^4$ is selected from the group consisting of (PC)

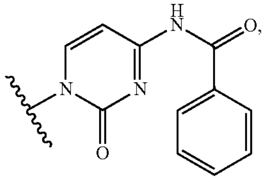

(DPG)

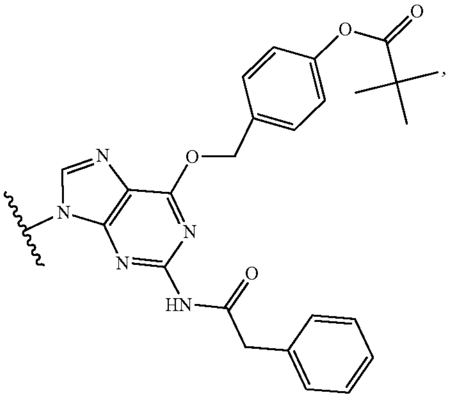

(T)

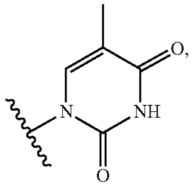

(PA)

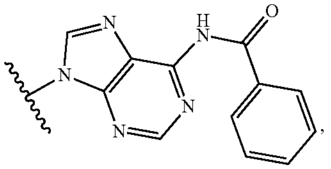

(P5mC)

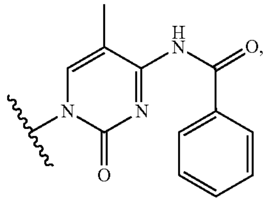

-continued (U)

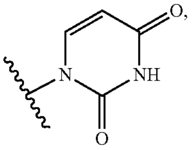

(I)

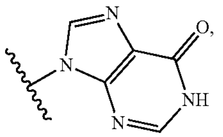

and (PG)

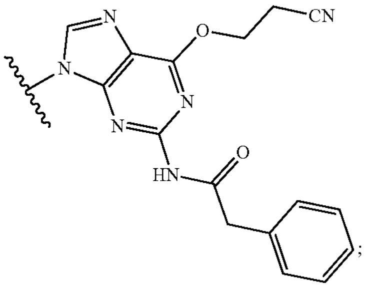

(b) washing the compound of Formula (IV) with a washing solvent and a neutralizing agent, wherein the washing comprises passing a washing solvent and a neutralizing agent through the reactor vessel;

(c) washing the compound of Formula (IV) with a washing solvent, wherein the washing comprises passing a washing solvent through the reactor vessel;

(d) washing the compound of Formula (IV) with a coupling solvent, wherein the washing comprises passing a coupling solvent through the reactor vessel;

(e) introducing to the reactor vessel a lewis acid and a compound of Formula (A4):

(A4)

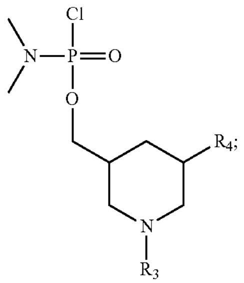

wherein $R^3$ is selected from the group consisting of trityl, monomethoxytrityl, dimethoxytrityl and trimethoxytrityl; and $R^4$ is selected from the group consisting of:
(PC)
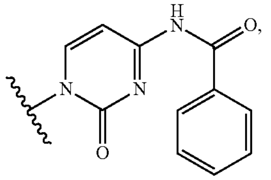
(DPG)
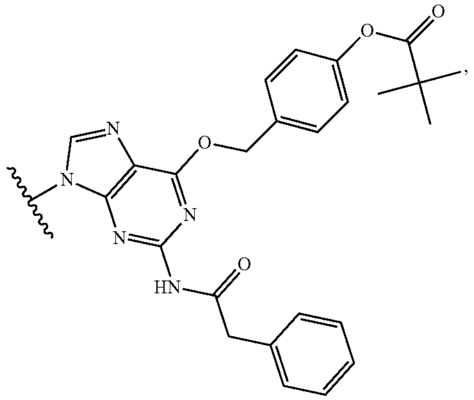
(PC)
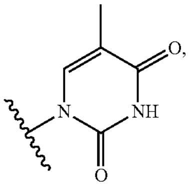
(PA)
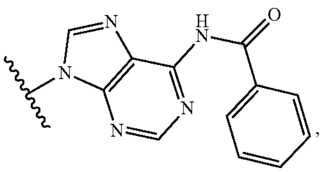
(P5mC)
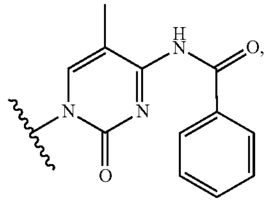
(U)
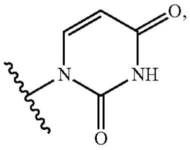
-continued
(I)
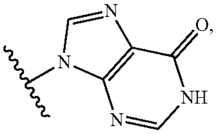
and
(PG)
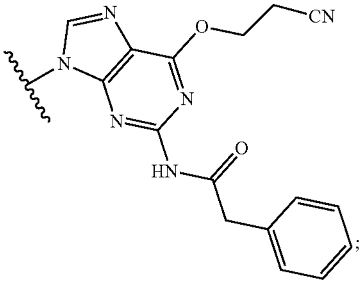
such that the compound of formula (A4) contacts the compound of Formula (IV) to form a compound of Formula (A5):
(A5)
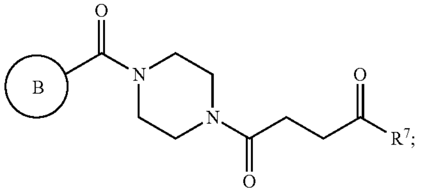
wherein $R^7$ is of the Formula (A5a) or Formula (A5b):
(A5a)
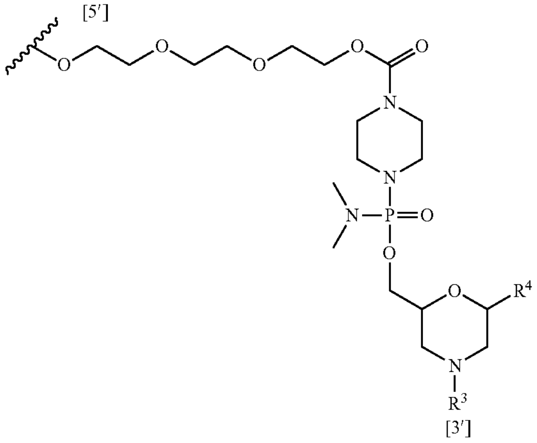
or -continued
(A5b)
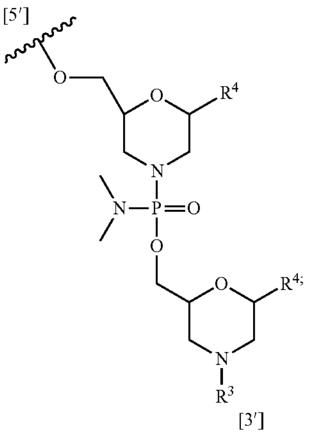
B is
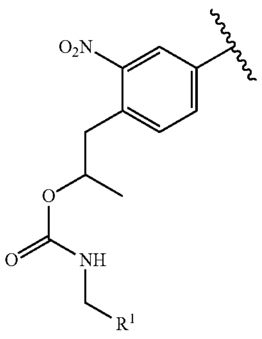
or
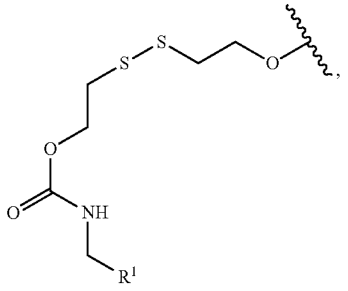
$R^1$ is a support-medium;
$R^3$ is selected from the group consisting of trityl, monomethoxytrityl, dimethoxytrityl and trimethoxytrityl; and
$R^4$ is selected from:
(PC)
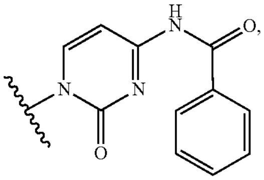
-continued
(DPG)
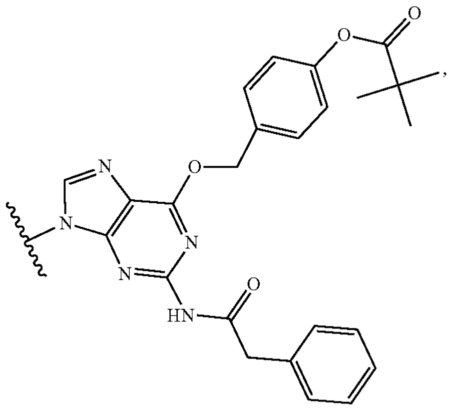
(T)
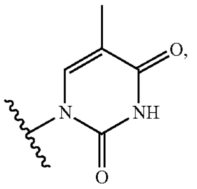
(PA)
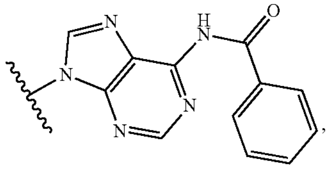
(P5mC)
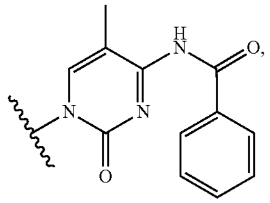
(U)
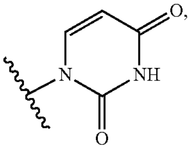
(I)
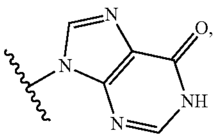
and
(PG)
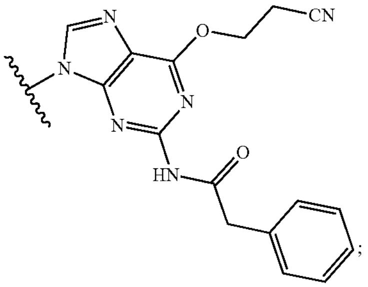

(f) washing the compound of Formula (A5) with a coupling solvent, wherein the washing comprises passing a coupling solvent through the reactor vessel;

(g) performing Y iterations of the sequential steps of:

(g1) washing the product formed by the immediately prior step with a washing solvent, wherein the washing comprises passing a washing solvent through the reactor vessel;

(g2) introducing a deblocking agent into the reactor vessel such that it contacts the product formed by the immediately prior step;

(g3) washing the product formed by the immediately prior step with a washing solvent and a neutralizing agent, wherein the washing comprises passing a washing solvent and a neutralizing agent through the reactor vessel;

(g4) washing the product formed by the immediately prior step with a washing solvent, wherein the washing comprises passing a washing solvent through the reactor vessel;

(g5) washing the product formed by the immediately prior step with a coupling solvent, wherein the washing comprises passing a coupling solvent through the reactor vessel;

(g6) introducing to the reactor vessel containing the product formed by the immediately prior step a Lewis acid and a compound of Formula (A8):

(A8)

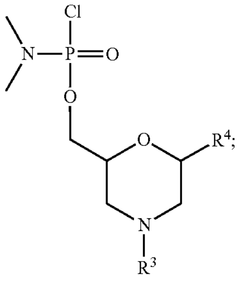

wherein

Y is n−1 if $R^7$ is of the Formula (A5a) or Y is n−2 if $R^7$ is of the Formula (A5b);

$R^3$ is selected from the group consisting of trityl, monomethoxytrityl, dimethoxytrityl and trimethoxytrityl; and $R^4$ is, independently for each compound of Formula (A8), selected from the group consisting of:

(PC)

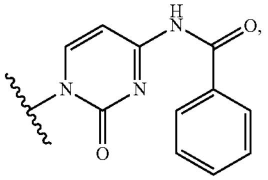

-continued (DPG)

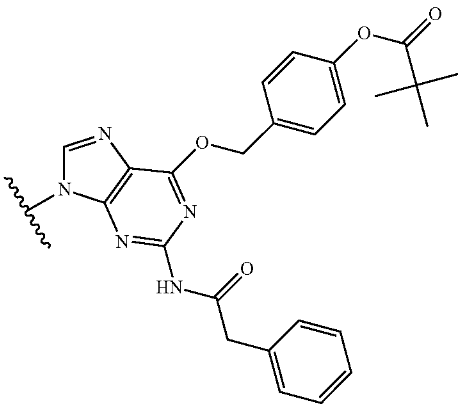

, (T)

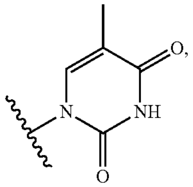

(PA)

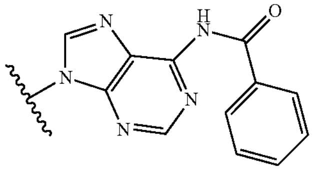

, (P5mC)

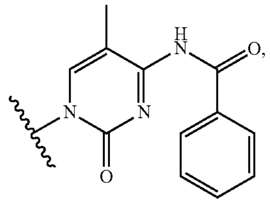

(U)

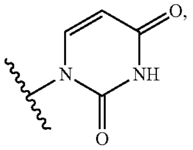

(I)

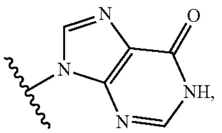

and (PG)

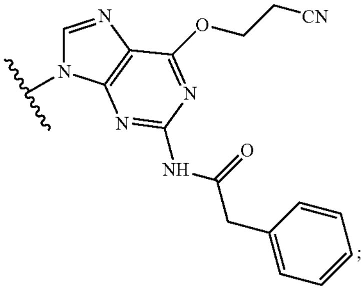

;

such that the compound of Formula (A8) contacts the compound formed by the immediately prior step to form a compound of Formula (A9):

(A9)

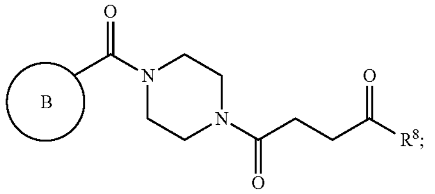

wherein $R^8$ is

[5']

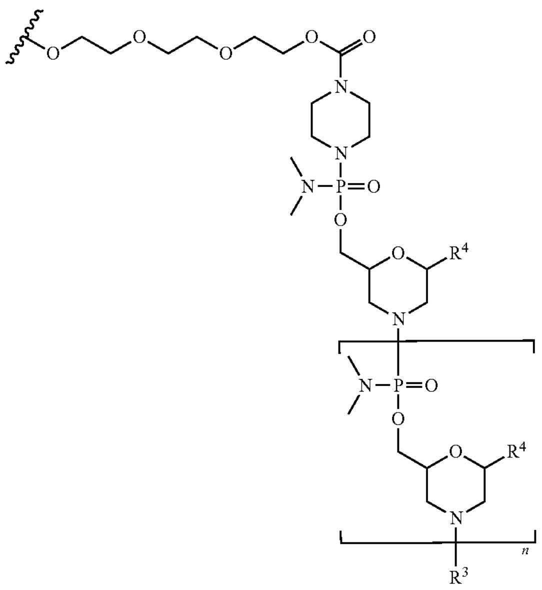

or

[3']

[5']

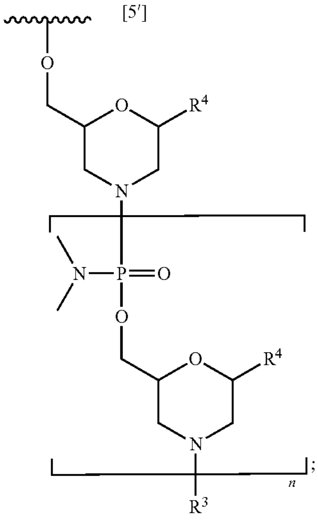

;

[3']

B is

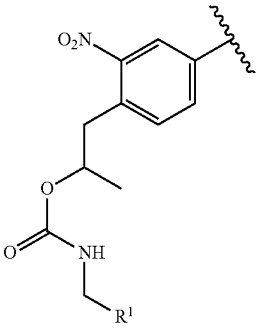

or

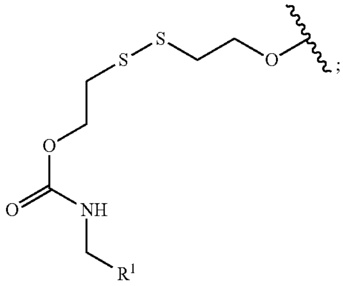

;

n is an integer from 9 to 39;

$R^1$ is a support-medium;

$R^3$ is selected from the group consisting of trityl, monomethoxytrityl, dimethoxytrityl and trimethoxytrityl; and $R^4$ is, independently for each occurrence, selected from the group consisting of:

(PC)

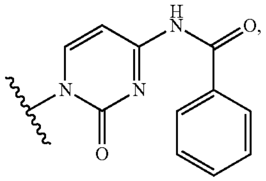

(DPG)

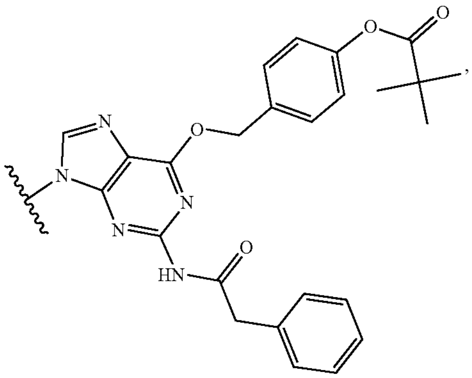

(T)

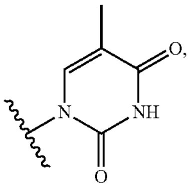

-continued (PA)

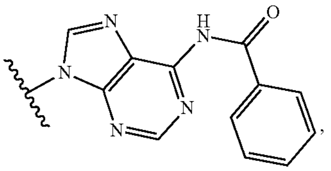

(P5mC)

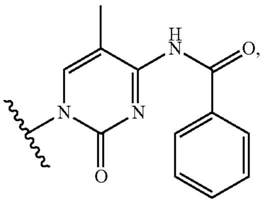

(U)

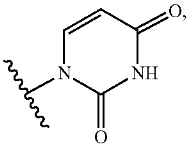

(I)

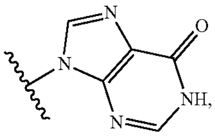

and (PG)

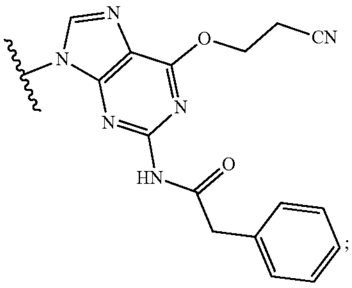

(h) washing the compound of Formula (A9) with a coupling solvent to remove the compound of Formula (A8), wherein the washing comprises passing a coupling solvent through the reactor vessel;

(i) washing the compound of Formula (A9) with a washing solvent to remove the coupling solvent, wherein the washing comprises passing a washing solvent through the reactor vessel;

(j) contacting a deblocking agent with a compound of Formula (A9) in a reactor vessel to form a compound of Formula (A10):

(A10)

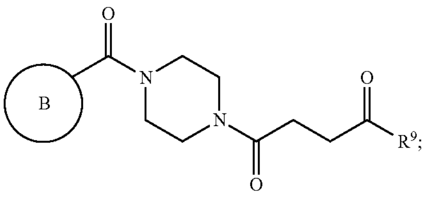

wherein $R^9$ is

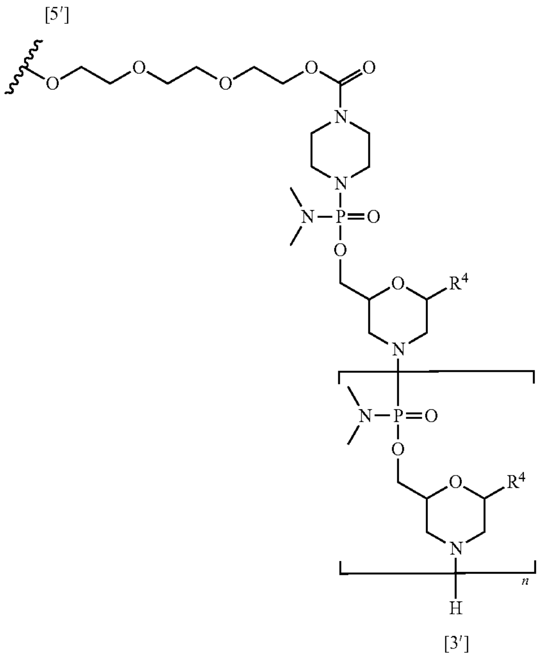

or

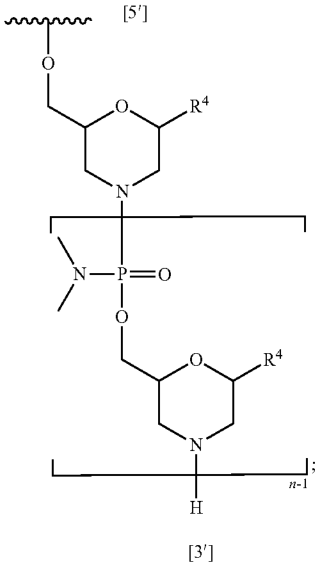

B is

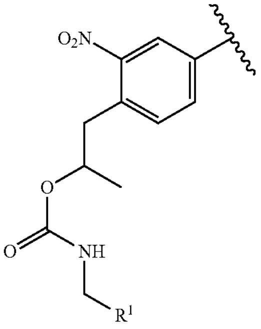

or

-continued

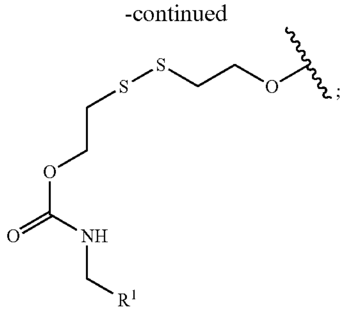

n is an integer from 10 to 40;

$R^1$ is a support-medium; and $R^4$ is, independently for each occurrence, selected from the group consisting of:

(PC)

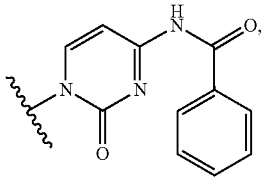

(DPG)

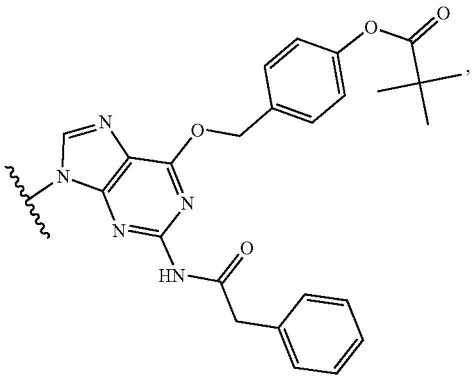

(T)

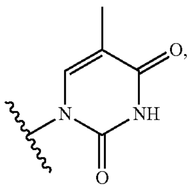

(PA)

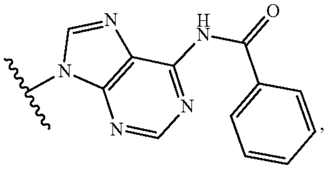

-continued (P5mC)

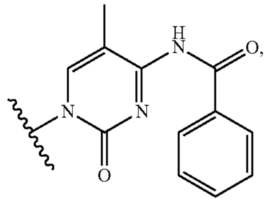

(U)

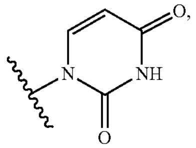

(I)

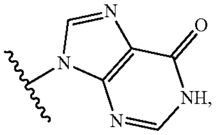

and (PG)

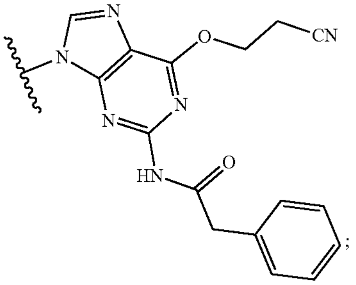

and (k) contacting a cleaving agent with a compound of Formula (10) in a reactor vessel to form a compound of Formula (A11).

In an embodiment, provided herein is a continuous process for preparing an oligomeric compound of Formula (A11):

(A11)

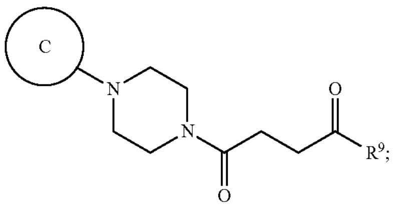

wherein $R^9$ is
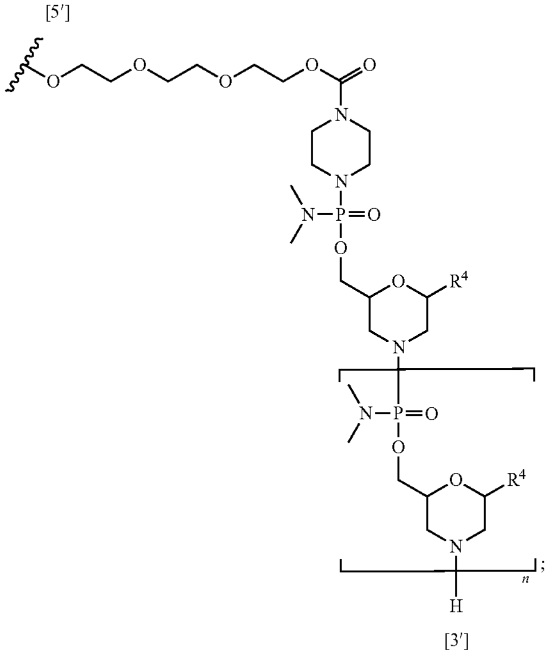
C is
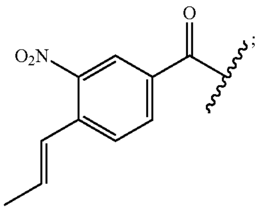
n is an integer from 9 to 39; and
$R^4$ is, independently for each occurrence, selected from the group consisting of:
(PC)
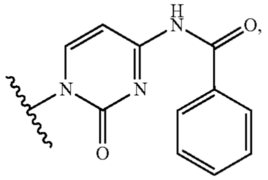
(DPG)
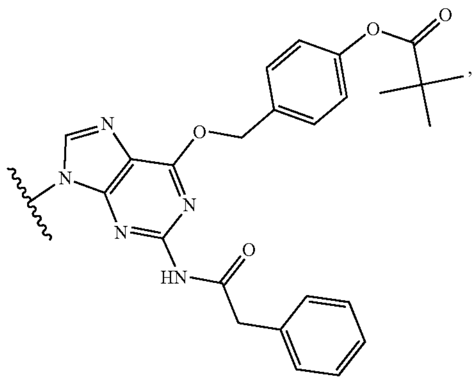
-continued
(T)
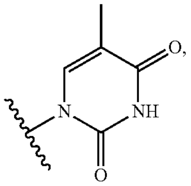
(PA)
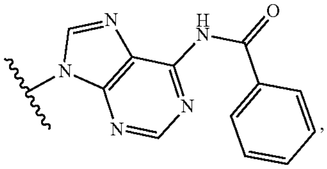
(P5mC)
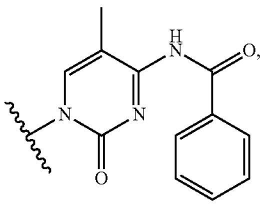
(U)
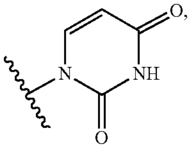
(I)
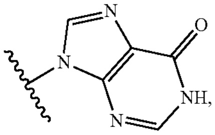
and
(PG)
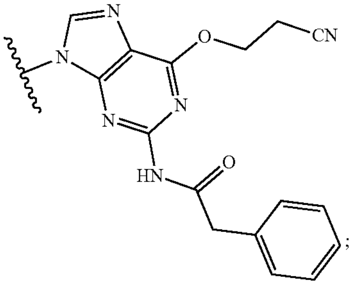
wherein the process comprises the sequential steps of:
(a) contacting a deblocking agent with a compound of Formula (A3):
(A3)
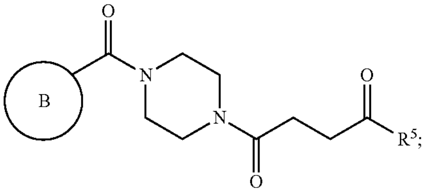

wherein B is

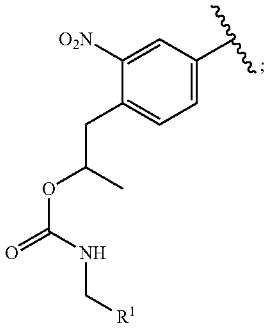

$R^1$ is a support-medium;

$R^5$ is

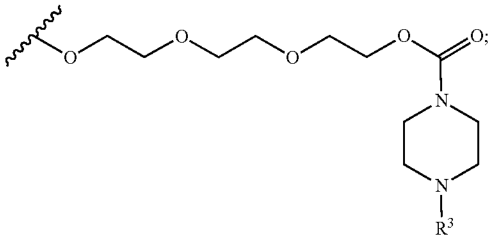

and $R^3$ is selected from the group consisting of trityl, monomethoxytrityl, dimethoxytrityl and trimethoxytrityl;

in a reactor vessel to form a compound of Formula (IV):

(IV)

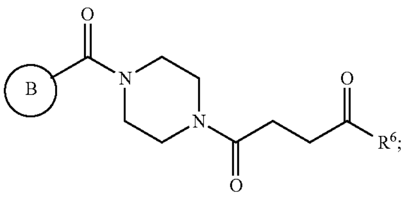

wherein B is

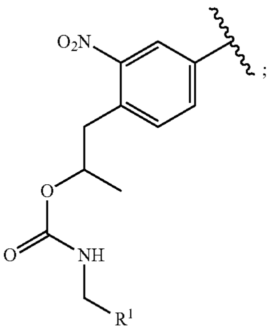

$R^1$ is a support-medium;

$R^6$ is

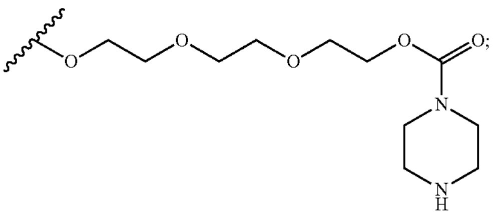 [SMILES: *OCCOCCOCCOC(=O)N1CCNCC1]

(b) washing the compound of Formula (IV) with a washing solvent and a neutralizing agent, wherein the washing comprises passing a washing solvent and a neutralizing agent through the reactor vessel;

(c) washing the compound of Formula (IV) with a washing solvent, wherein the washing comprises passing a washing solvent through the reactor vessel;

(d) washing the compound of Formula (IV) with a coupling solvent, wherein the washing comprises passing a coupling solvent through the reactor vessel;

(e) introducing to the reactor vessel a Lewis acid and a compound of Formula (A4):

(A4)

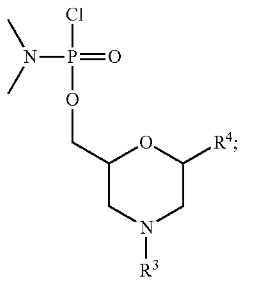

wherein $R^3$ is selected from the group consisting of trityl, monomethoxytrityl, dimethoxytrityl and trimethoxytrityl; and $R^4$ is selected from the group consisting of:

(PC)

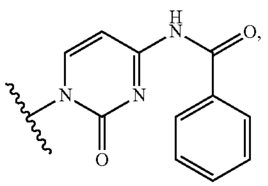

-continued
(DPG)
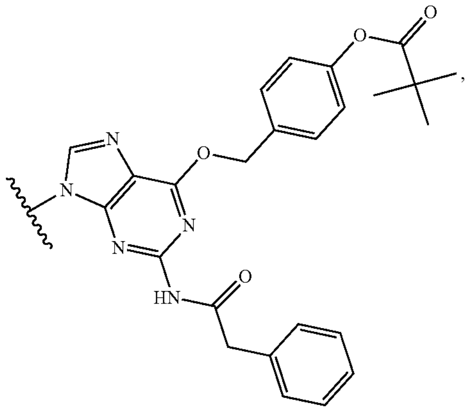
(T)
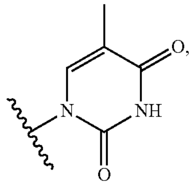
(PA)
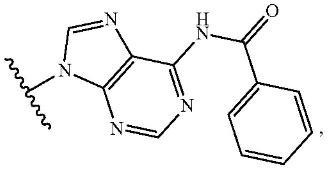
(P5mC)
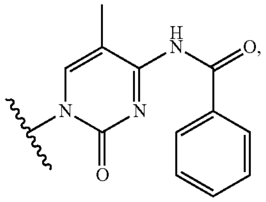
(U)
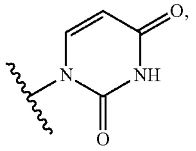
(I)
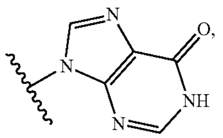
and
(PG)
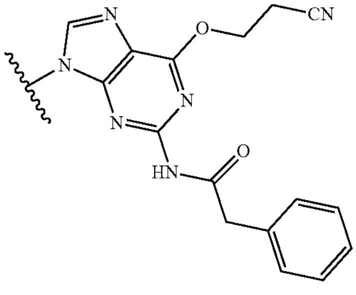
such that the compound of formula (A4) contacts the compound of Formula (IV) to form a compound of Formula (A5):
(A5)
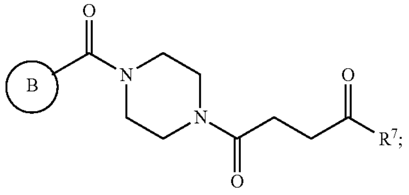
wherein $R^7$ is of the Formula (A5a) or Formula (A5b):
(A5a)
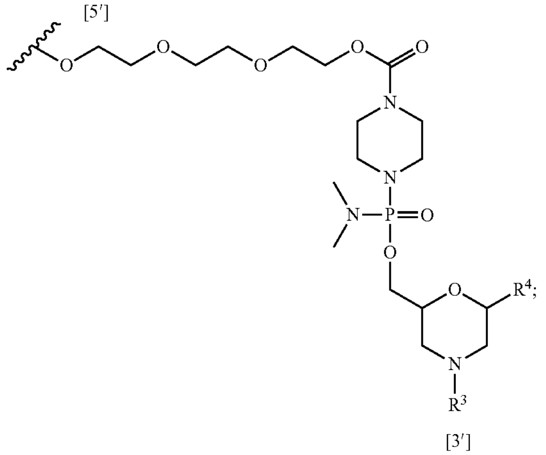
B is
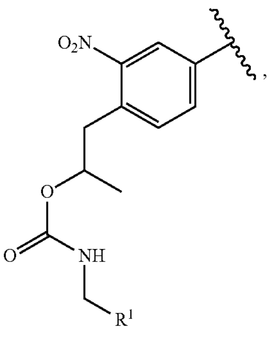
$R^1$ is a support-medium;
$R^3$ is selected from the group consisting of trityl, monomethoxytrityl, dimethoxytrityl and trimethoxytrityl; and $R^4$ is selected from:

(PC)

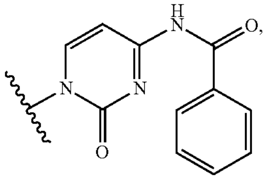

(DPG)

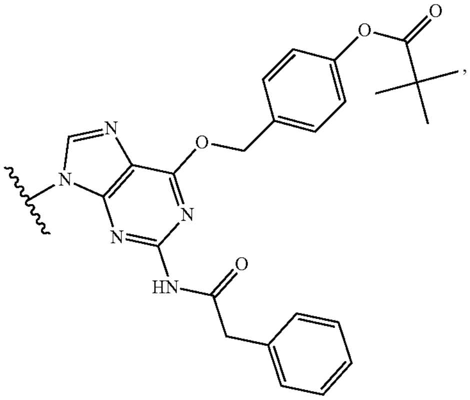

(T)

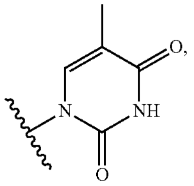

(PA)

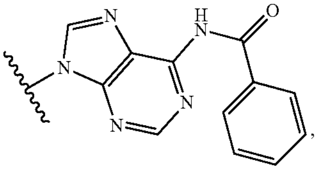

(P5mC)

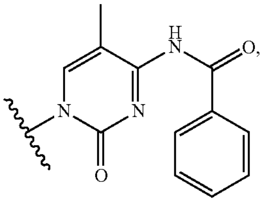

(U)

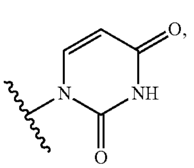

(I)

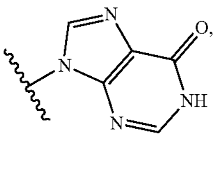

and

-continued (PG)

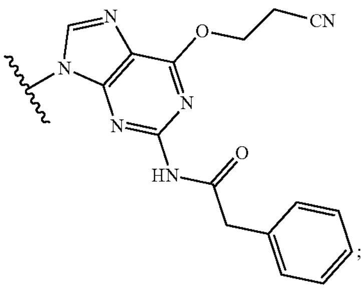

;

(f) washing the compound of Formula (A5) with a coupling solvent, wherein the washing comprises passing a coupling solvent through the reactor vessel;

(g) performing Y iterations of the sequential steps of:

(g1) washing the product formed by the immediately prior step with a washing solvent, wherein the washing comprises passing a washing solvent through the reactor vessel;

(g2) introducing a deblocking agent into the reactor vessel such that it contacts the product formed by the immediately prior step;

(g3) washing the product formed by the immediately prior step with a washing solvent and a neutralizing agent, wherein the washing comprises passing a washing solvent and a neutralizing agent through the reactor vessel;

(g4) washing the product formed by the immediately prior step with a washing solvent, wherein the washing comprises passing a washing solvent through the reactor vessel;

(g5) washing the product formed by the immediately prior step with a coupling solvent, wherein the washing comprises passing a coupling solvent through the reactor vessel;

(g6) introducing to the reactor vessel containing the product formed by the immediately prior step a Lewis acid and a compound of Formula (A8):

(A8)

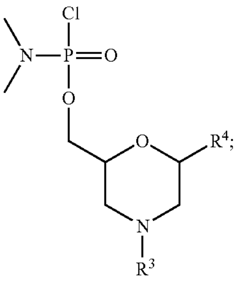

wherein

Y is n−1;

$R^3$ is selected from the group consisting of trityl, monomethoxytrityl, dimethoxytrityl and trimethoxytrityl; and $R^4$ is, independently for each compound of Formula (A8), selected from the group consisting of:

(PC)
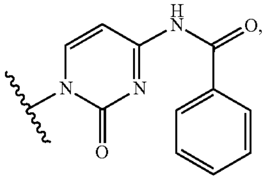
(DPG)
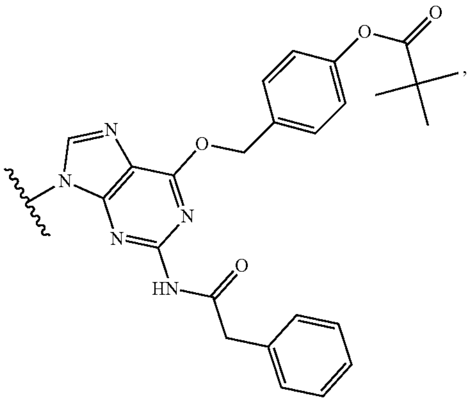
(T)
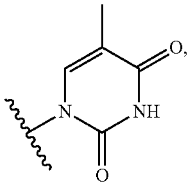
(PA)
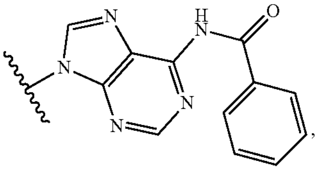
(P5mC)
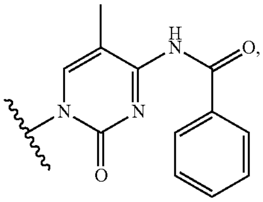
(U)
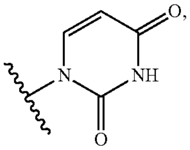
(I)
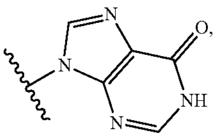 and
-continued
(PG)
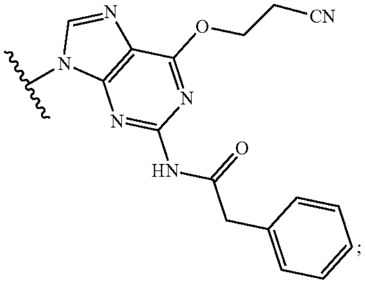
such that the compound of Formula (A8) contacts the compound formed by the immediately prior step to form a compound of Formula (A9):
(A9)
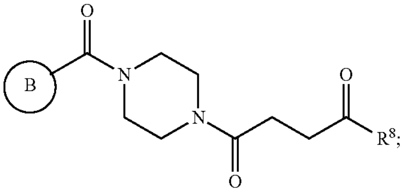
wherein $R^8$ is
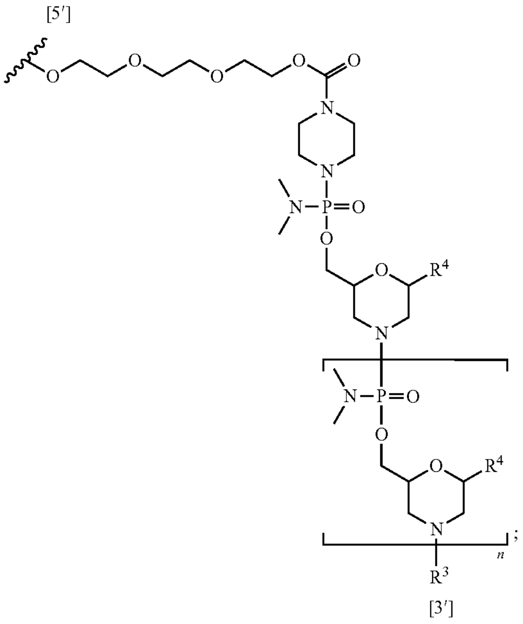

B is

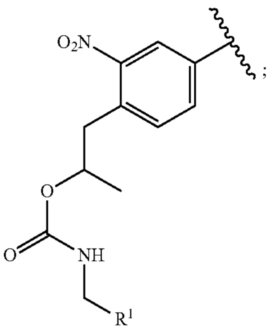

n is an integer from 9 to 39;

$R^1$ is a support-medium;

$R^3$ is selected from the group consisting of trityl, monomethoxytrityl, dimethoxytrityl and trimethoxytrityl; and $R^4$ is, independently for each occurrence, selected from the group consisting of:

(PC)

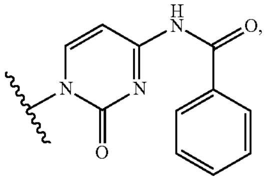

(DPG)

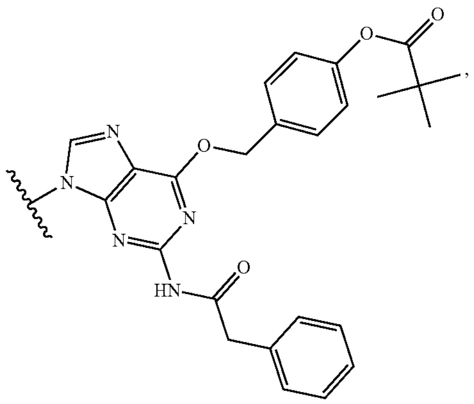

(T)

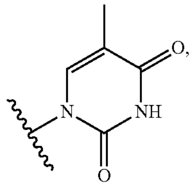

(PA)

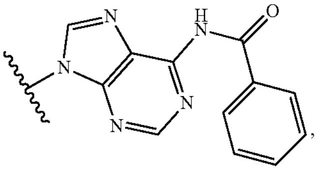

-continued (P5mC)

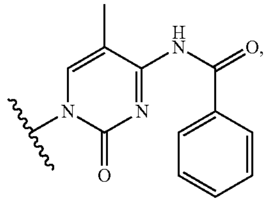

(U)

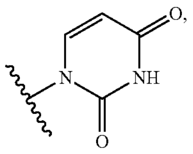

(I)

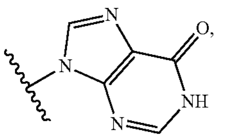

and (PG)

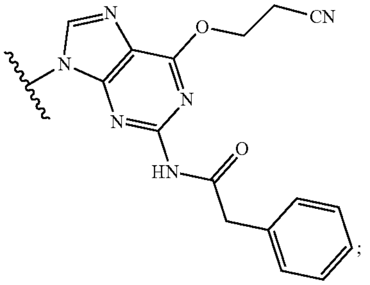

(h) washing the compound of Formula (A9) with a coupling solvent to remove the compound of Formula (A8), wherein the washing comprises passing a coupling solvent through the reactor vessel;

(i) washing the compound of Formula (A9) with a washing solvent to remove the coupling solvent, wherein the washing comprises passing a washing solvent through the reactor vessel;

(j) contacting a deblocking agent with a compound of Formula (A9) in a reactor vessel to form a compound of Formula (A10):

(A10)

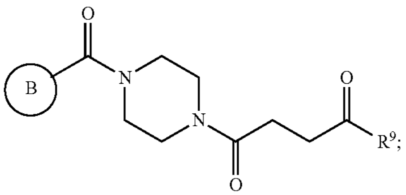

wherein $R^9$ is
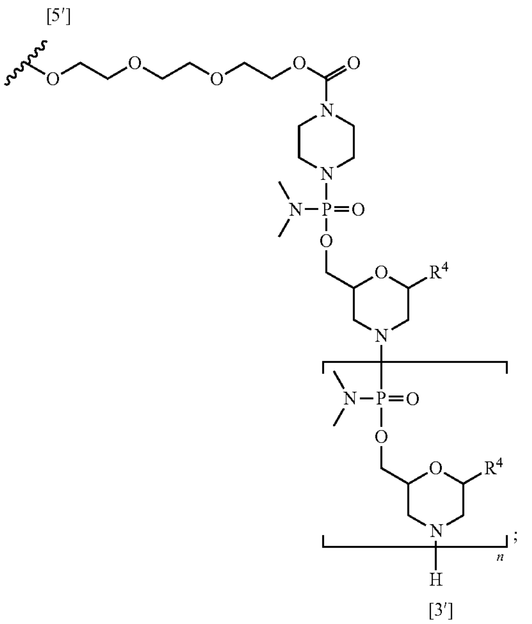
B is
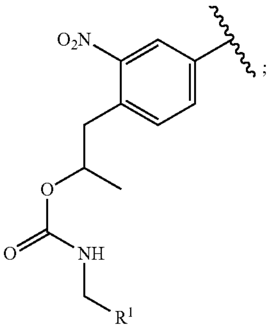
n is an integer from 9 to 39;
$R^1$ is a support-medium; and
$R^4$ is, independently for each occurrence, selected from the group consisting of:
(PC)
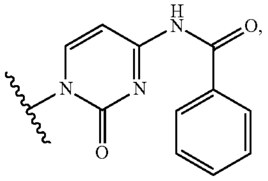
-continued
(DPG)
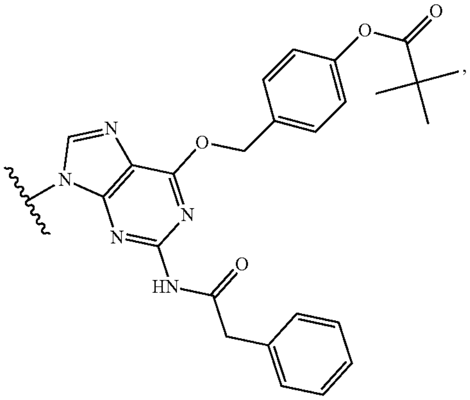
(T)
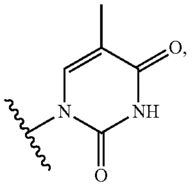
(PA)
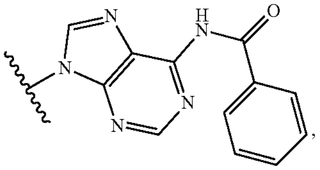
(P5mC)
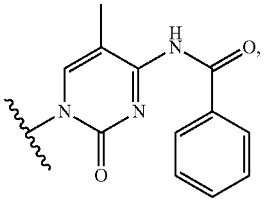
(U)
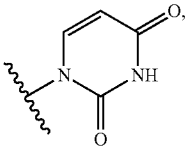
(I)
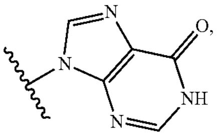
and
(PG)
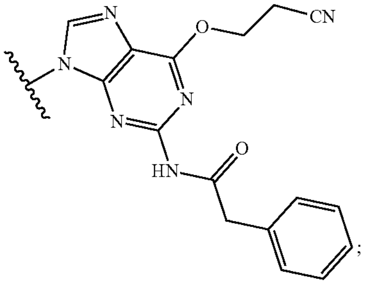

and (k) contacting a cleaving agent with a compound of Formula (10) in a reactor vessel to form a compound of Formula (A11).

In an embodiment, at least one of steps (a), (g2), and (j) further comprises contacting the deblocked compound of the respective step with a neutralization agent.

In another embodiment, steps (a), (g2), and (j) further comprise contacting the deblocked compound of each respective step with a neutralization agent.

In an embodiment, the washing solvent is a halogenated solvent.

In another embodiment, the washing solvent is dichlormethane or dichloroethane.

In an embodiment, the coupling solvent is 1,3-dimethyl-2-imidazolidinone or N-methyl-2-pyrrolidone.

In an embodiment, the cleaving agent comprises $NH_3$.

In another embodiment, the cleaving agent is in an aqueous solution.

In yet another embodiment, the support-medium comprises polystyrene with 1% crosslinked divinylbenzene.

In an embodiment, any one of steps (a), (b), (c), (d), (e), (f), (g1), (g2), (g3), (g4), (g5), (g6), (h), (i), (j), and (k) is run between 70° C. and 90° C.

In another embodiment, each of steps (a), (b), (c), (d), (e), (f), (g1), (g2), (g3), (g4), (g5), (g6), (h), (i), (j), and (k) is run between 70° C. and 90° C.

In a particular embodiment, each of steps (e) and (g6) is run between 70° C. and 90° C.

In an embodiment, each of steps (a), (g2), and (j) is run between 70° C. and 90° C.; and the deblocking agent used in each step is a solution comprising 3,5-dimethylpyridine, dichloroethane, trifluoroacetic acid, and trifluoroethanol.

In an embodiment, each of steps (a), (g2), and (j) is run between 70° C. and 90° C.; and the deblocking agent used in each step is a solution comprising 3,5-dimethylpyridine, dichloromethane, trifluoroacetic acid, and trifluoroethanol.

In another embodiment, each of steps (a), (g2), and (j) is run between room temperature and 70° C.; and the deblocking agent used in each step is a solution comprising 4-cyanopyridine, dichloroethane, trifluoroacetic acid, and trifluoroethanol.

In yet another embodiment, each of steps (a), (g2), and (j) is run between room temperature and 70° C.; and the deblocking agent used in each step is a solution comprising 4-cyanopyridine, dichloromethane, trifluoroacetic acid, and trifluoroethanol.

In an embodiment, steps (a)-(j), B is

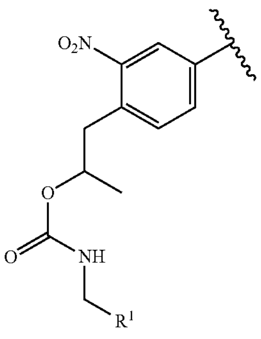

and step (k), C is

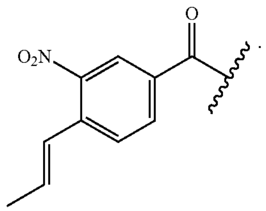 [SMILES: *C(=O)c1ccc(/C=C/C)c([N+](=O)[O-])c1]

In an embodiment, any of steps (a), (b), (c), (d), (e), (f), (g1), (g2), (g3), (g4), (g5), (g6), (h), (i), (j), and (k) are optionally carried out in a batchwise process.

In an embodiment, the deblocking agent used in each step is a solution comprising a halogenated acid.

In another embodiment, the deblocking agent is selected from the group consisting of chloroacetic acid, dichloroacetic acid, trichloroacetic acid, fluoroacetic acid, difluoroacetic acid, and trifluoroacetic acid.

In a particular embodiment, the deblocking agent is trifluoroacetic acid.

In an embodiment, the Lewis acid is soluble in the coupling solvent.

In another embodiment, the Lewis acid is selected from a group consisting of LiCl, LiBr, LiI, and LiOTf.

In a particular embodiment, the Lewis acid is LiBr.

In an embodiment, the neutralization agent is in a solution comprising a halogenated solvent and isopropyl alcohol.

In another embodiment, the halogenated solvent is dichloromethane or dichloroethane.

In yet another embodiment, the neutralization agent is a monoalkyl, dialkyl, or trialkyl amine.

In another embodiment, the neutralization agent is N,N-diisopropylethylamine.

In another embodiment, the neutralization agent is N-ethylmorpholine.

In an embodiment, the deblocking agent used in each step is a solution comprising 4-cyanopyridine, dichloromethane, trifluoroacetic acid, trifluoroethanol, and water.

In an embodiment, the deblocking agent used in each step is a solution comprising 4-cyanopyridine, dichloroethane, trifluoroacetic acid, trifluoroethanol, and water.

In an embodiment, the deblocking agent used in each step is a solution comprising 3,5-dimethylpyridine, dichloromethane, trifluoroacetic acid, trifluoroethanol, and water.

In an embodiment, the deblocking agent used in each step is a solution comprising 3,5-dimethylpyridine, dichloroethane, trifluoroacetic acid, trifluoroethanol, and water.

In an embodiment of the oligomeric compound of Formula (A11), n is 30, and $R^4$ is at each position from 1 to 30 and 5' to 3':

| Position No. 5' to 3' | $R^4$ |
|---|---|
| 1 | PC |
| 2 | T |
| 3 | PC |
| 4 | PC |
| 5 | PA |
| 6 | PA |
| 7 | PC |
| 8 | PA |
| 9 | T |
| 10 | PC |
| 11 | PA |
| 12 | PA |
| 13 | DPG |
| 14 | DPG |

-continued

| Position No. 5' to 3' | $R^4$ |
|---|---|
| 15 | PA |
| 16 | PA |
| 17 | DPG |
| 18 | PA |
| 19 | T |
| 20 | DPG |
| 21 | DPG |
| 22 | PC |
| 23 | PA |
| 24 | T |
| 25 | T |
| 26 | T |
| 27 | PC |
| 28 | T |
| 29 | PA |
| 30 | DPG |

In an embodiment of the oligomeric compound of Formula (A11), n is 10, and $R^4$ is at each position from 1 to 10 and 5' to 3':

| Position No. 5' to 3' | $R^4$ |
|---|---|
| 1 | PC |
| 2 | T |
| 3 | PC |
| 4 | PC |
| 5 | PA |
| 6 | PA |
| 7 | PC |
| 8 | PA |
| 9 | T |
| 10 | PC |

A Continuous Processes for Preparing Morpholino Oligomers in a Flow-Through Reactor Provided herein is a continuous (flow-through) process for preparing morpholino oligomers in a flow-through reactor.

Accordingly, in an aspect, provided herein is a continuous process for preparing an oligomeric compound of Formula (A11):

(A11)

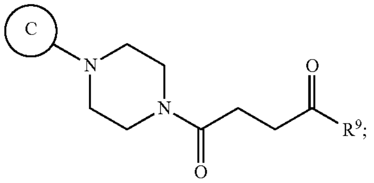

wherein $R^9$ is

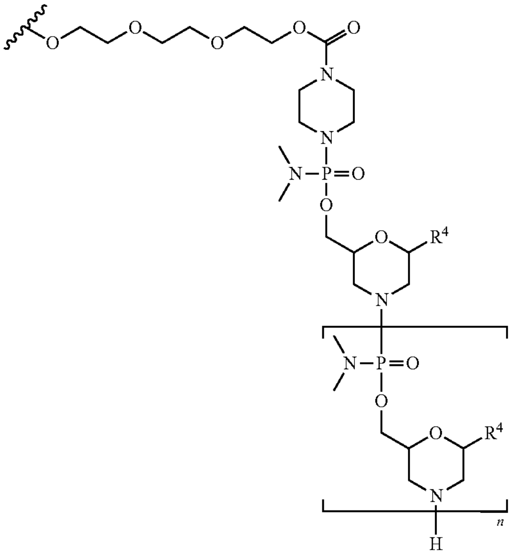

[3']

or

[5']

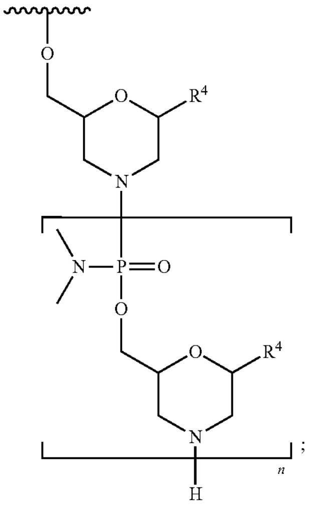

[3']

C is

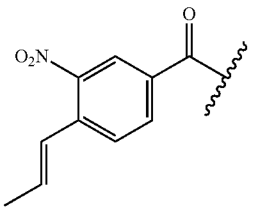 [SMILES: *C(=O)c1ccc(/C=C/C)c([N+](=O)[O-])c1]

or H;

n is an integer from 9 to 39; and $R^4$ is, independently for each occurrence, selected from the group consisting of:

(PC)
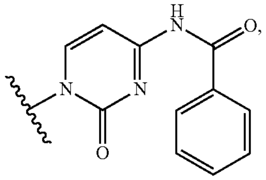
(DPG)
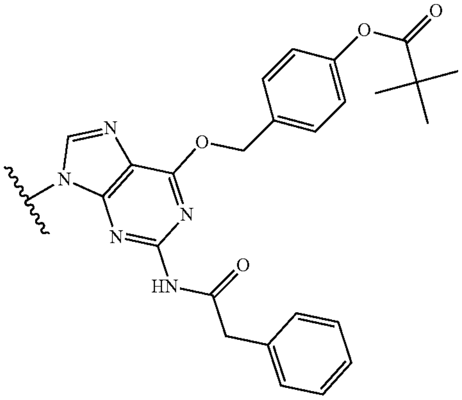
,
(T)
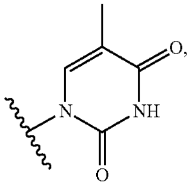
(PA)
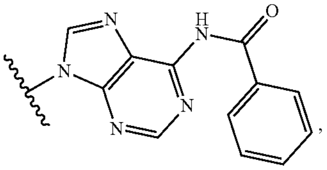
(P5mC)
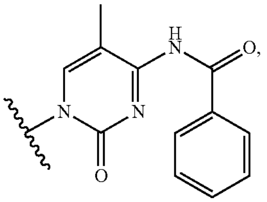
(U)
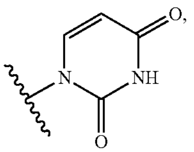
(I)
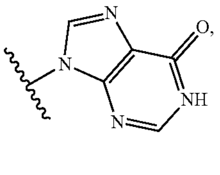
and
-continued
(PG)
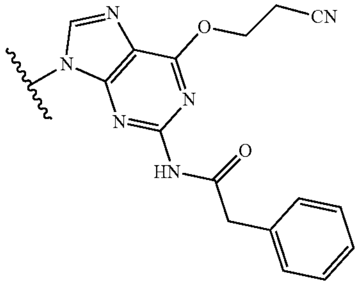
;
wherein the process comprises the sequential steps of:
(a) contacting a deblocking agent with a compound of Formula (A3):
(A3)
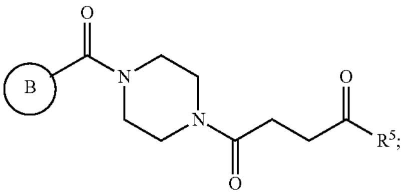
wherein B is
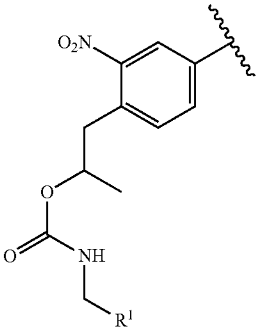
or
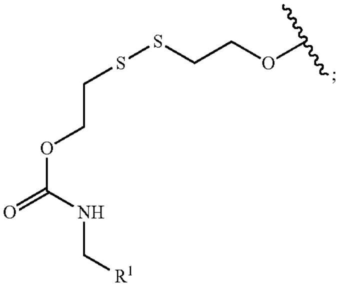
;
$R^1$ is a support-medium;
$R^3$ is selected from the group consisting of trityl, monomethoxytrityl, dimethoxytrityl and trimethoxytrityl;

$R^5$ is
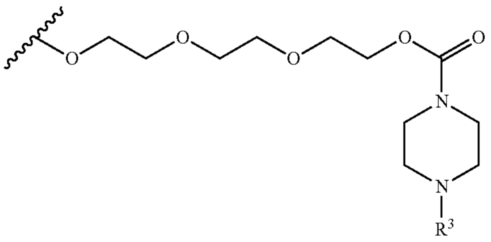
or
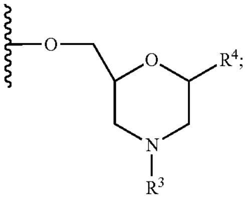
$R^3$ is selected from the group consisting of trityl, monomethoxytrityl, dimethoxytrityl and trimethoxytrityl; and
$R^4$ is selected from the group consisting of:
(PC)
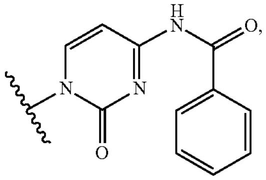
(DPG)
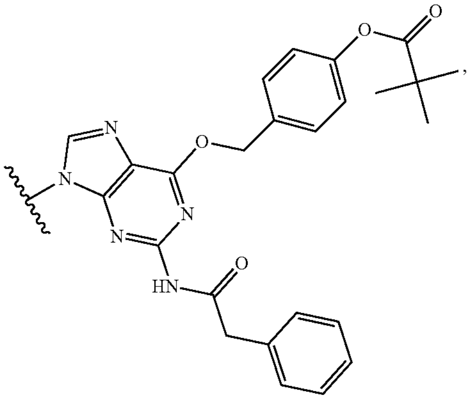
(T)
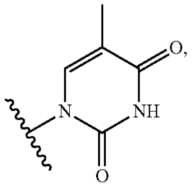
(PA)
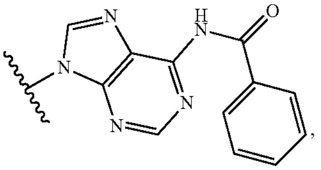
-continued
(P5mC)
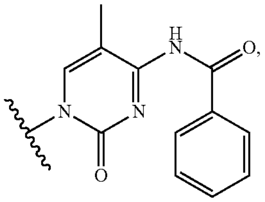
(U)
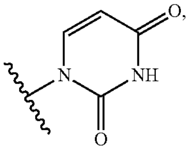
(I)
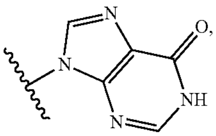
and
(PG)
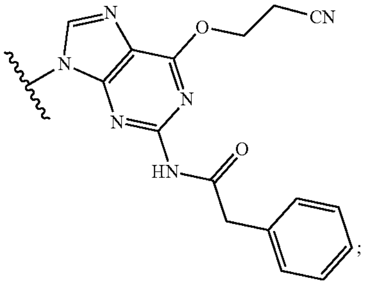
in a reactor vessel to form a compound of Formula (IV):
(IV)
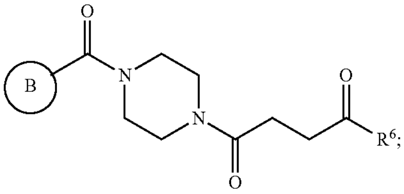
wherein B is
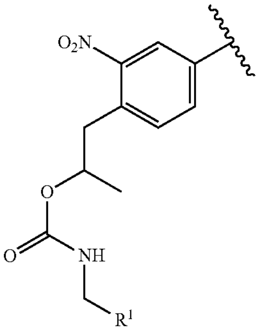
or -continued

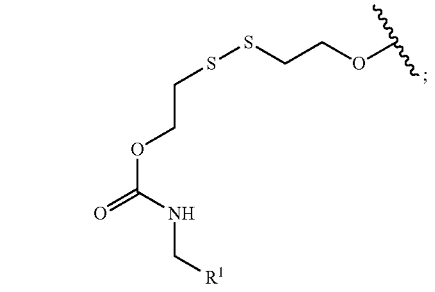

$R^1$ is a support-medium;

$R^6$ is

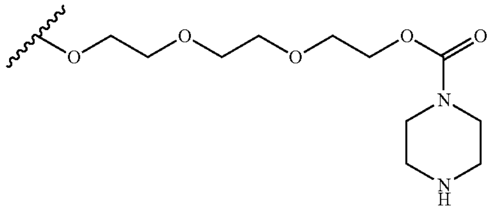

or

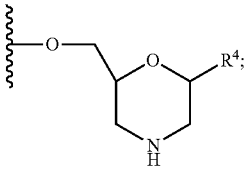

and $R^4$ is selected from the group consisting of (PC)

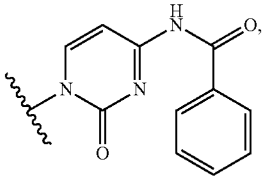

(DPG)

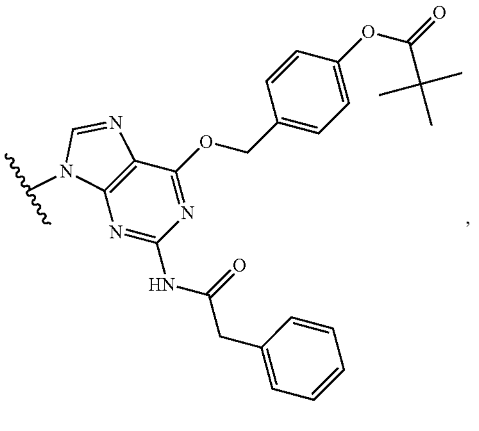

,

-continued (T)

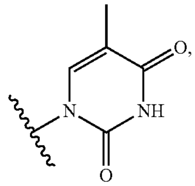

(PA)

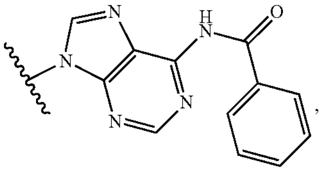

(P5mC)

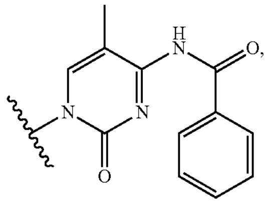

(U)

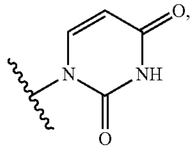

(I)

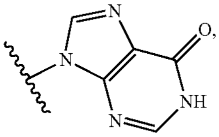

and (PG)

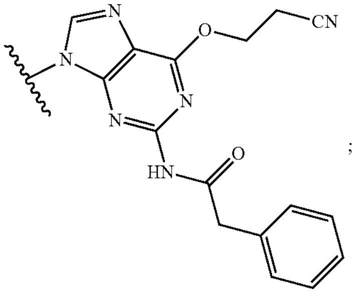

;

(b) washing the compound of Formula (IV) with a washing solvent and a neutralizing agent, wherein the washing comprises passing a washing solvent and a neutralizing agent through the reactor vessel;

(c) washing the compound of Formula (IV) with a washing solvent, wherein the washing comprises passing a washing solvent through the reactor vessel;

(d) washing the compound of Formula (IV) with a coupling solvent, wherein the washing comprises passing a coupling solvent through the reactor vessel;

(e) introducing to the reactor vessel a Lewis acid and a compound of Formula (A4):

(A4)
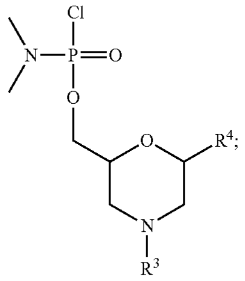
wherein
$R^3$ is selected from the group consisting of trityl, monomethoxytrityl, dimethoxytrityl and trimethoxytrityl; and
$R^4$ is selected from the group consisting of:
(PC)
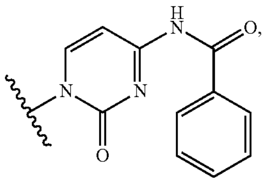
(DPG)
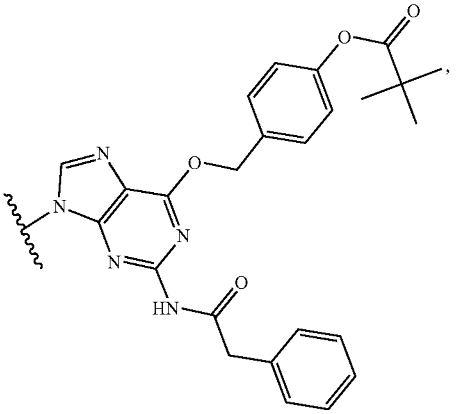
(T)
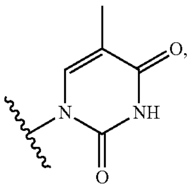
(PA)
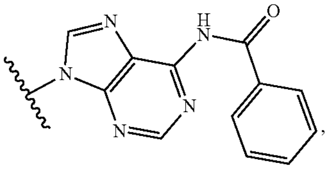
-continued
(P5mC)
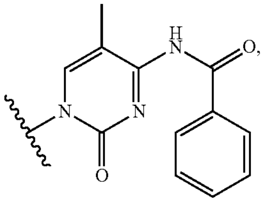
(U)
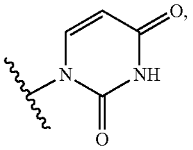
(I)
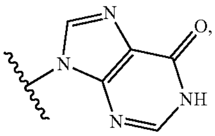
and
(PG)
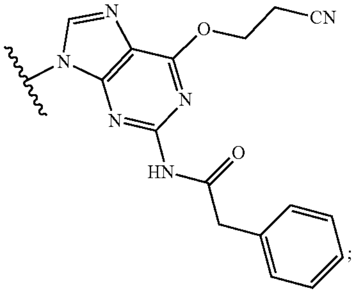
such that the compound of formula (A4) contacts the compound of Formula (IV) to form a compound of Formula (A5):
(A5)
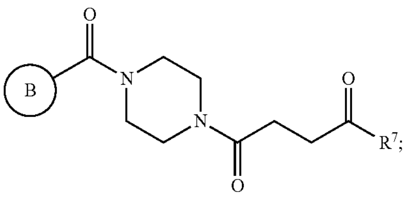

wherein $R^7$ is of the Formula (A5a) or Formula (A5b):
(A5a)
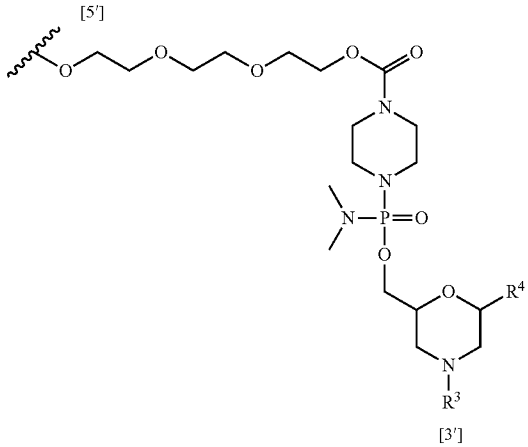
or
(A5b)
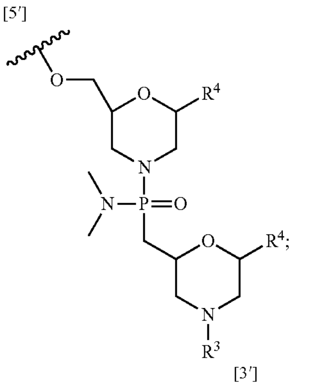
B is
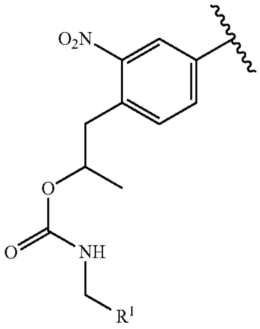
or
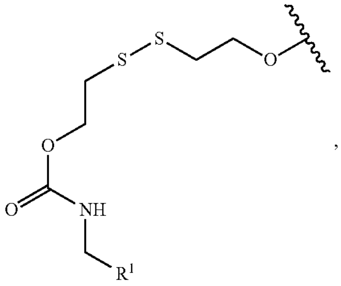
,
$R^1$ is a support-medium;
$R^3$ is selected from the group consisting of trityl, monomethoxytrityl, dimethoxytrityl and trimethoxytrityl; and
$R^4$ is selected from:
(PC)
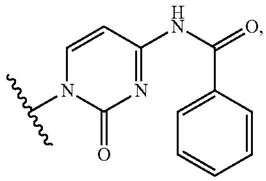
(DPG)
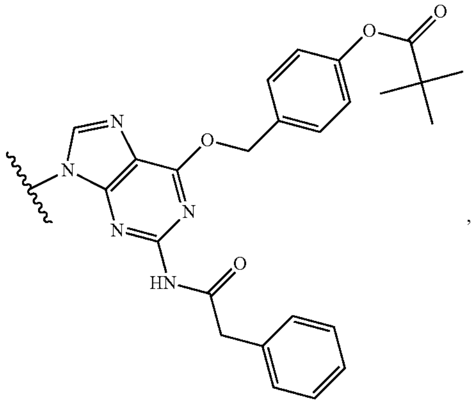
,
(T)
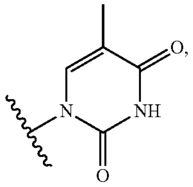
(PA)
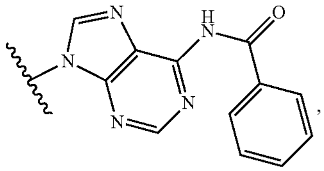
(P5mC)
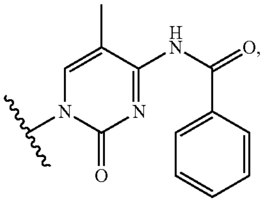
(U)
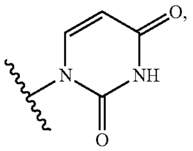
(I)
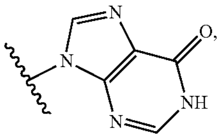
and -continued (PG)

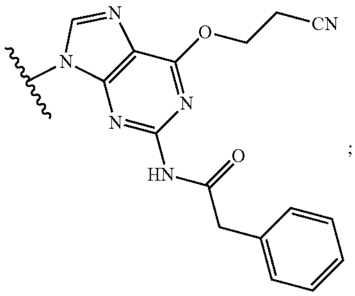

;

(f) washing the compound of Formula (A5) with a coupling solvent, wherein the washing comprises passing a coupling solvent through the reactor vessel;

(g) performing Y iterations of the sequential steps of: (g1) washing the product formed by the immediately prior step with a washing solvent, wherein the washing comprises passing a washing solvent through the reactor vessel;

(g2) introducing a deblocking agent into the reactor vessel such that it contacts the product formed by the immediately prior step;

(g3) washing the product formed by the immediately prior step with a washing solvent and a neutralizing agent, wherein the washing comprises passing a washing solvent and a neutralizing agent through the reactor vessel;

(g4) washing the product formed by the immediately prior step with a washing solvent, wherein the washing comprises passing a washing solvent through the reactor vessel;

(g5) washing the product formed by the immediately prior step with a coupling solvent, wherein the washing comprises passing a coupling solvent through the reactor vessel;

(g6) introducing to the reactor vessel containing the product formed by the immediately prior step a Lewis acid and a compound of Formula (A8):

(A8)

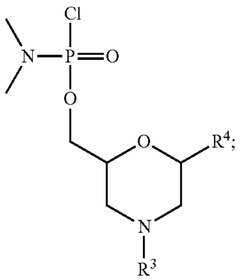

wherein

Y is n−1 if $R^7$ is of the Formula (A5a) or Y is n−2 if $R^7$ is of the Formula (A5b);

$R^3$ is selected from the group consisting of trityl, monomethoxytrityl, dimethoxytrityl and trimethoxytrityl; and $R^4$ is, independently for each compound of Formula (A8), selected from the group consisting of:

(PC)

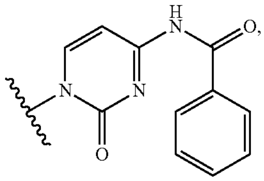

(DPG)

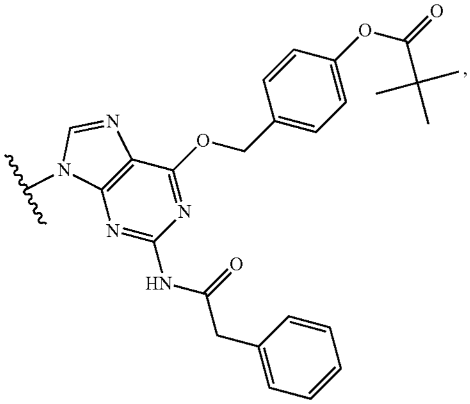

(T)

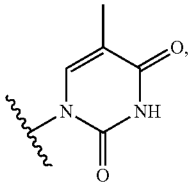

(PA)

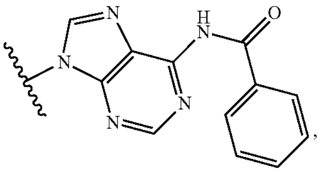

(P5mC)

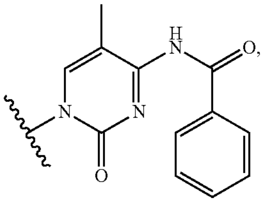

(U)

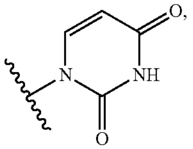

(I)

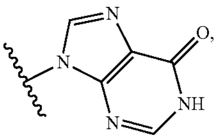

and

-continued (PG)

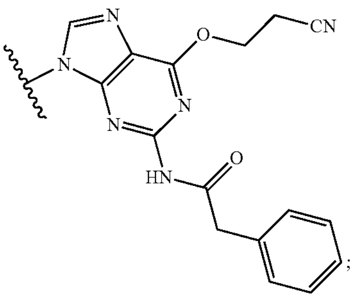

such that the compound of Formula (A8) contacts the compound formed by the immediately prior step to form a compound of Formula (A9):

(A9)

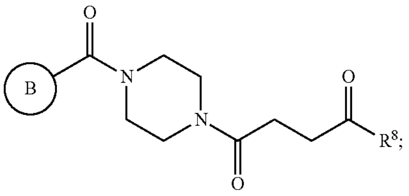

wherein $R^8$ is

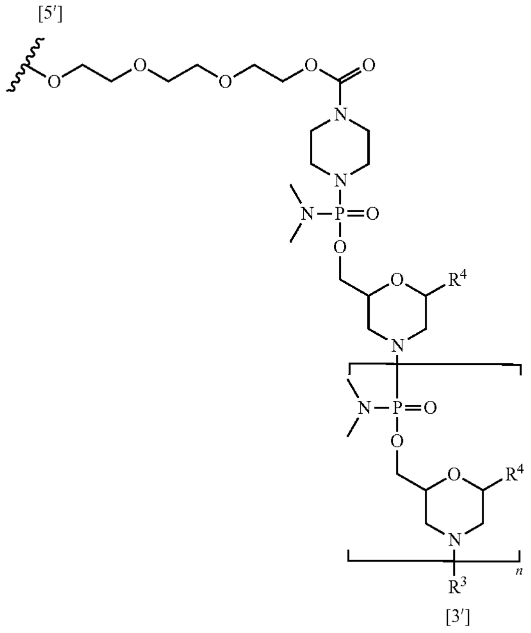

or

-continued

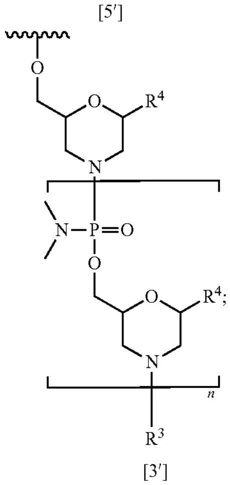

B is

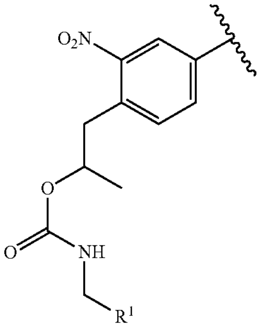

or

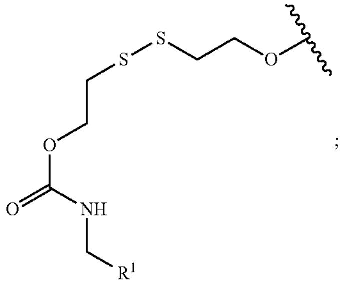

;

n is an integer from 9 to 39;

$R^1$ is a support-medium;

$R^3$ is selected from the group consisting of trityl, monomethoxytrityl, dimethoxytrityl and trimethoxytrityl; and $R^4$ is, independently for each occurrence, selected from the group consisting of:

(PC)

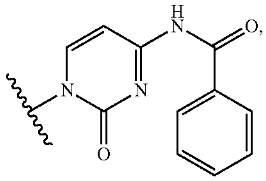

-continued (DPG)

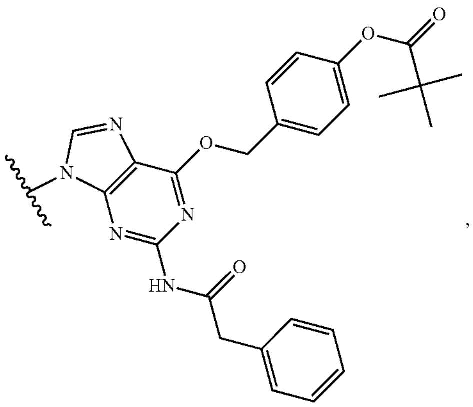

, (T)

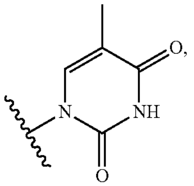

(PA)

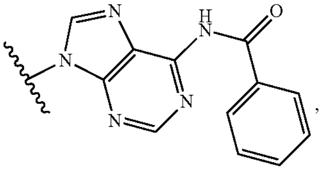

, (P5mC)

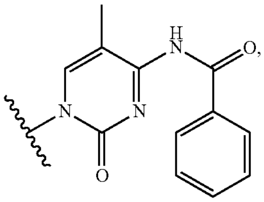

(U)

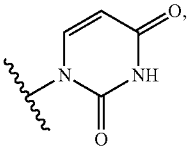

(I)

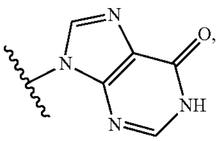

and (PG)

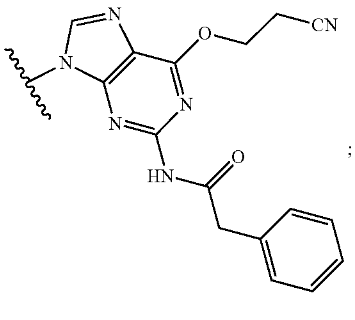

;

(h) washing the compound of Formula (A9) with a coupling solvent to remove the compound of Formula (A8), wherein the washing comprises passing a coupling solvent through the reactor vessel;

(i) washing the compound of Formula (A9) with a washing solvent to remove the coupling solvent, wherein the washing comprises passing a washing solvent through the reactor vessel;

(j) contacting a deblocking agent with a compound of Formula (A10) in a reactor vessel to form a compound of Formula (A10):

(A10)

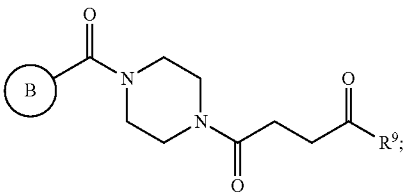

wherein $R^9$ is

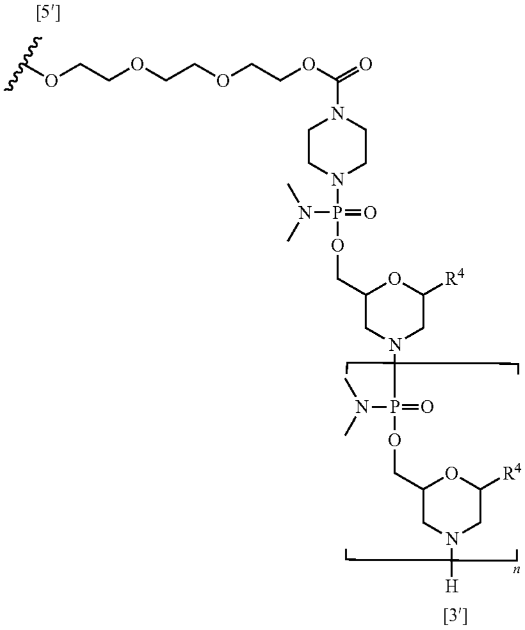

or

-continued
[5']
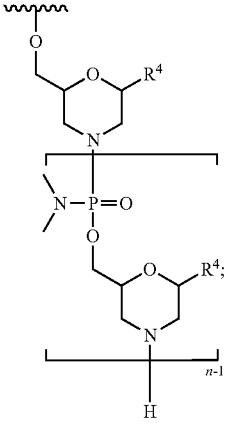
[3']
B is
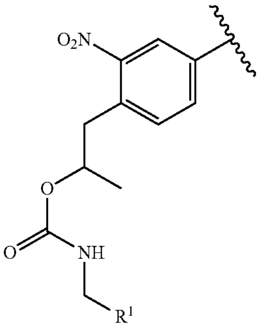
or
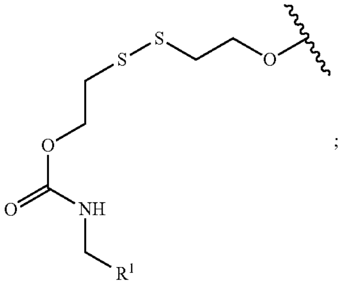
;
n is an integer from 10 to 40;
$R^1$ is a support-medium; and
$R^4$ is, independently for each occurrence, selected from the group consisting of:
(PC)
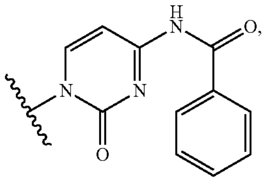
-continued
(DPG)
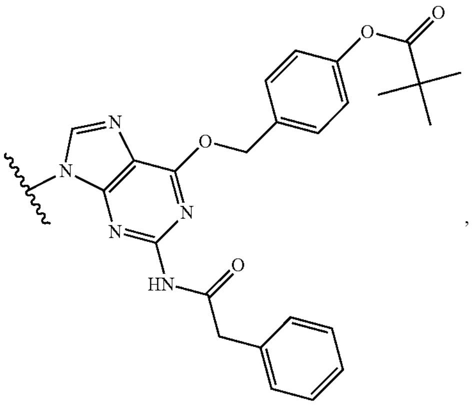
,
(T)
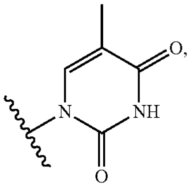
(PA)
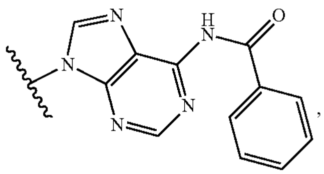
(P5mC)
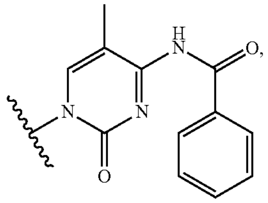
(U)
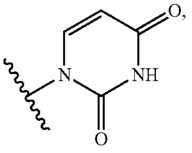
(I)
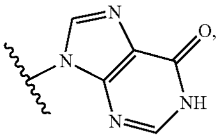
and
(PG)
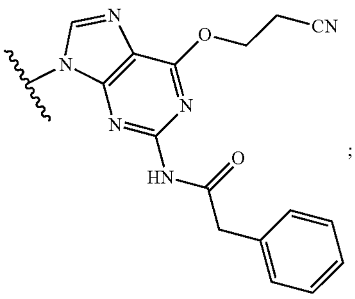
;

and (k) contacting a cleaving agent with a compound of Formula (10) in a reactor vessel to form a compound of Formula (A11);

wherein the process is performed in a flow-through reactor, the flow-through reactor comprising at least:

(a) a feeding zone, wherein the feeding zone comprises one or more feed lines each equipped with a pump, and wherein the inlet zones of the feed lines are independently connected to vessels comprising a neutralizing agent, coupling solvent, a deblocking agent, washing solvent, and a compound of Formula (A8):

(A8)

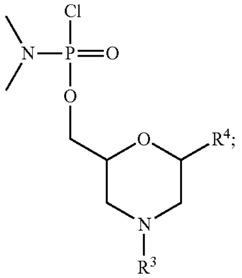

wherein $R^3$ is selected from the group consisting of trityl, monomethoxytrityl, dimethoxytrityl and trimethoxytrityl; and $R^4$ is, independently for each compound of Formula (A8), selected from the group consisting of:

(PC)

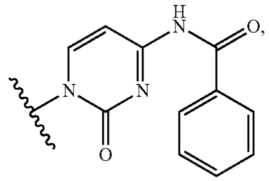

(DPG)

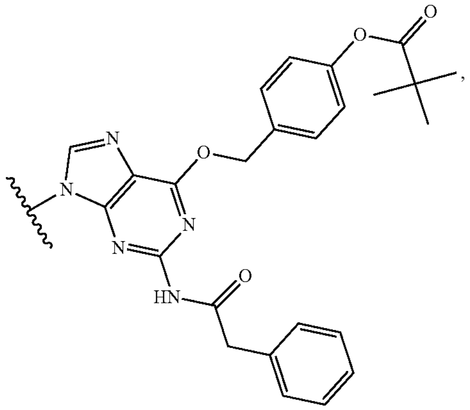

(T)

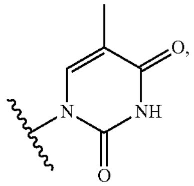

-continued (PA)

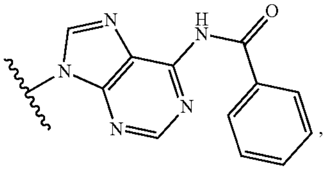

(P5mC)

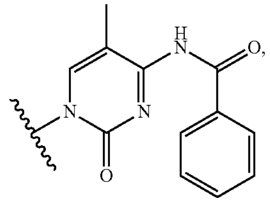

(U)

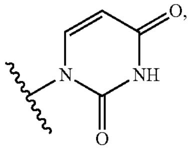

(I)

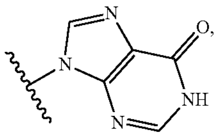

and (PG)

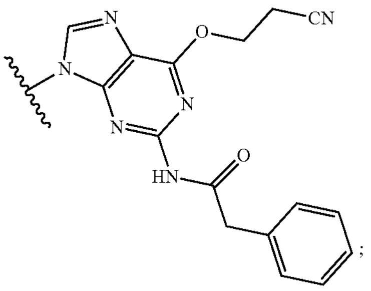

wherein the compound of Formula (A8) is dissolved in a coupling solvent;

(b) a reaction zone that is connected to the outlet zone of the one or more feed lines and which contains a PMO synthesis resin;

(c) an outlet zone, whereby waste stream or product can be independently collected;

(d) a pressure control device; and (e) a means of independently controlling the temperature of the feeding zone and the reaction zone.

In an embodiment, the neutralizing reagent is a monoalkyl, dialkyl, or trialkyl amine in a solution comprising a halogenated solvent and isopropyl alcohol.

In another embodiment, the monoalkyl, dialkyl, or trialkyl amine is N,N-diisopropylethylamine or N-ethylmorpholine.

In yet another embodiment, the halogenated solvent is dichlormethane or dichloroethane.

In an embodiment, the coupling solvent is lithium bromide dissolved in 3-dimethyl-2-imidazolidinone or N-methyl-2-pyrrolidone.

In another embodiment, the deblocking agent is a solution comprising 4-cyanopyridine, dichloromethane, trifluoroacetic acid, and trifluoroethanol.

In yet another embodiment, the deblocking agent is a solution comprising 4-cyanopyridine, dichloroethane, trifluoroacetic acid, and trifluoroethanol.

In a further embodiment, the deblocking agent is a solution comprising 3,5-dimethylpyridine, dichloromethane, trifluoroacetic acid, and trifluoroethanol.

In an embodiment, the deblocking agent is a solution comprising 3,5-dimethylpyridine, dichloroethane, trifluoroacetic acid, and trifluoroethanol.

In an embodiment, the washing solvent is dichloroethane or dichloromethane.

In another embodiment, the compound of Formula (A8) is in a solution of 3-dimethyl-2-imidazolidinone or N-methyl-2-pyrrolidone.

In yet another embodiment, the pump is an HPLC or syringe pump.

In a further embodiment, the feeding zone and the reaction zone are connected by a luer lock connector.

In an embodiment, the reaction zone comprises a reactor vessel and a temperature control bath.

In an embodiment, the reactor vessel is equipped with a frit such that the PMO synthesis resin is not removed during the process.

In yet another embodiment, the reactor vessel is equipped with a 2 μm frit.

In a further embodiment, the pressure control device is a back pressure regulator.

In a particular embodiment, the flow-through reactor is used for the preparation of Eteplirsen.

Oligomers

Important properties of morpholino-based subunits include: 1) the ability to be linked in an oligomeric form by stable, uncharged or positively charged backbone linkages; 2) the ability to support a nucleotide base (e.g. adenine, cytosine, guanine, thymidine, uracil, 5-methyl-cytosine and hypoxanthine) such that the polymer formed can hybridize with a complementary-base target nucleic acid, including target RNA; 3) the ability of the oligomer to be actively or passively transported into mammalian cells; and 4) the ability of the oligomer and oligomer:RNA heteroduplex to resist RNAse and RNase H degradation, respectively.

In some embodiments, the antisense oligomers contain base modifications or substitutions. For example, certain nucleo-bases may be selected to increase the binding affinity of the antisense oligomers described herein. 5-methylcytosine substitutions have been shown to increase nucleic acid duplex stability by 0.6-1.2° C., and may be incorporated into the antisense oligomers described herein. In one embodiment, at least one pyrimidine base of the oligomer comprises a 5-substituted pyrimidine base, wherein the pyrimidine base is selected from the group consisting of cytosine, thymine and uracil. In one embodiment, the 5-substituted pyrimidine base is 5-methylcytosine. In another embodiment, at least one purine base of the oligomer comprises hypoxanthine.

Morpholino-based oligomers (including antisense oligomers) are detailed, for example, in U.S. Pat. Nos. 5,698,685, 5,217,866, 5,142,047, 5,034,506, 5,166,315, 5,185,444, 5,521,063, 5,506,337, 8,299,206, and 8,076,476, International Patent Application Publication Nos. WO/2009/064471 and WO/2012/043730, and Summerton et al. (1997, Antisense and Nucleic Acid Drug Development, 7, 187-195), each of which are hereby incorporated by reference in their entirety.

Oligomeric compounds of the disclosure may have asymmetric centers, chiral axes, and chiral planes (as described, for example, in: E. L. Eliel and S. H. Wilen, Stereo-chemistry of Carbon Compounds, John Wiley & Sons, New York, 1994, pages 1119-1190, and March, J., Advanced Organic Chemistry, 3d. Ed., Chap. 4, John Wiley & Sons, New York (1985)), and may occur as racemates, racemic mixtures, and as individual diastereomers, with all possible isomers and mixtures thereof, including optical isomers. Oligomeric compounds of the disclosure herein specifically mentioned, without any indication of its stereo-chemistry, are intended to represent all possible isomers and mixtures thereof.

Specifically, without wishing to be bound by any particular theory, oligomeric compounds of the disclosure are prepared, as discussed herein, from activated morpholino subunits including such non-limiting examples such as a compound of Formula (VIII):

(VIII)

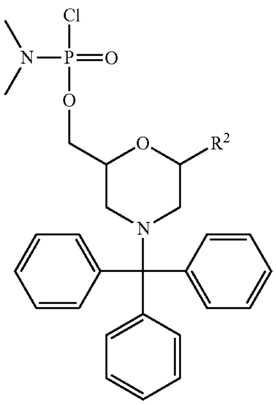
;

wherein $R^2$ is, independently for each compound of Formula (VIII), selected from the group consisting of:

(PC)

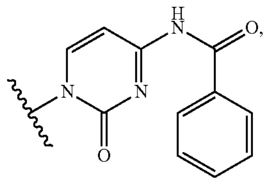

(DPG)

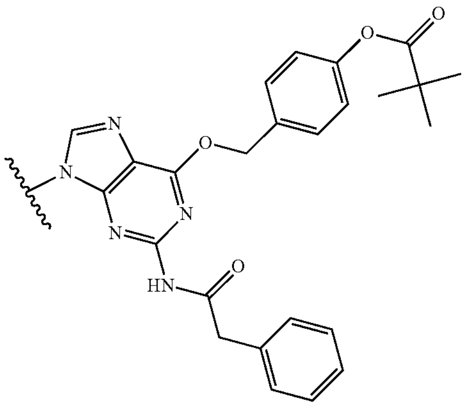
, (T)

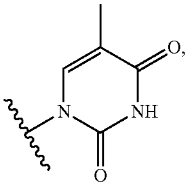
and

-continued (PA)

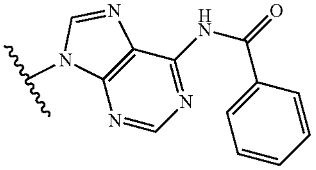

Each of the above-mentioned compounds of Formula (VIII), may be prepared, for example, from the corresponding beta-D-ribofuranosyl as depicted below:

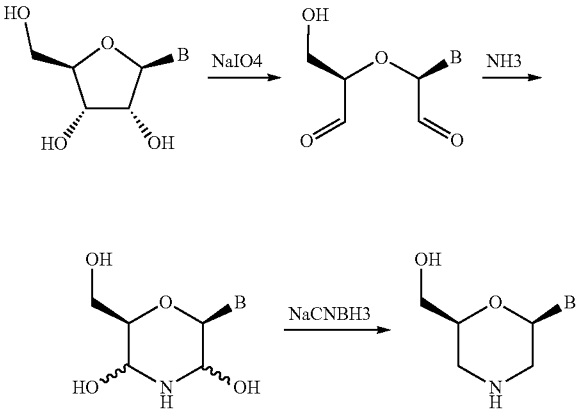

See Summerton et al., Antisense & Nucleic Acid Drug Dev. 7:187-195 (1997). Without being bound by any particular theory, the stereo chemistry of the two chiral carbons is retained under the synthetic conditions such that a number of possible stereo isomers of each morpholino subunit may be produced based on selection of, for example, an alpha-L-ribofuranosyl, alpha-D-ribofuranosyl, beta-L-ribofuranosyl, or beta-D-ribofuranosyl starting material.

For example, in some embodiments, a compound of Formula (VIII) of the disclosure may be of Formula (VIIIa):

(VIIIa)

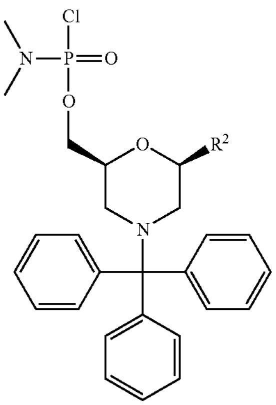

;

wherein $R^2$ is, independently for each compound of Formula (VIIIa), selected from the group consisting of:

(PC)

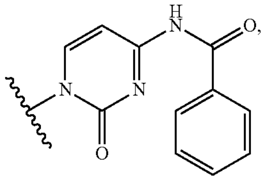

(DPG)

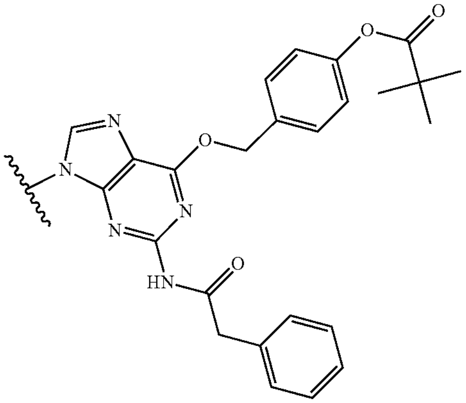

, (T)

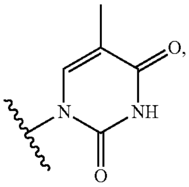

and (PA)

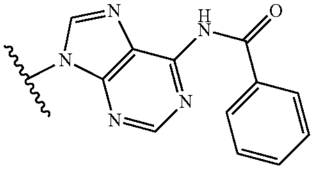

.

Without being bound by any particular theory, incorporation of 10 to 40 compounds of Formula (VIII), for example, into an oligomeric compound of the disclosure may result in numerous possible stereo isomers.

Without wishing to be bound by any particular theory, oligomeric compounds of the disclosure comprise one or more phosphorous-containing intersubunits, which create a chiral center at each phosphorus, each of which is designated as either an "Sp" or "Rp" configuration as understood in the art. Without wishing to be bound by any particular theory, this chirality creates stereoisomers, which have identical chemical composition but different three-dimensional arrangement of their atoms.

Without wishing to be bound by any particular theory, the configuration of each phosphorous intersubunit linkage occurs randomly during synthesis of, for example, oligomeric compounds of the disclosure. Without wishing to be bound by any particular theory, the synthesis process generates an exponentially large number of stereoisomers of an oligomeric compound of the disclosure because oligomeric compounds of the disclosure are comprised of numerous phosphorous intersubunit linkages—with each phosphorous intersubunit linkage having a random chiral configuration. Specifically, without wishing to be bound by any particular theory, each intersubunit linkage of an additional morpholino subunit doubles the number of stereoisomers of the product, so that a conventional preparation of an oligomeric compound of the disclosure is in fact a highly heterogeneous mixtures of $2^N$ stereoisomers, where N represents the number of phosphorous intersubunit linkages.

Thus, unless otherwise indicated, all such isomers, including diastereomeric and enantiomeric mixtures, and pure enantiomers and diastereomers are included such as, for example, when one or more bonds from one or more stereo center is indicated by "-" or "~~" or an equivalent as would be understood in the art.

Table 1 depicts various embodiments of morpholino subunits provided in the processes described herein.

TABLE 1

| Various embodiments of morpholino subunits. |
|---|
| A = 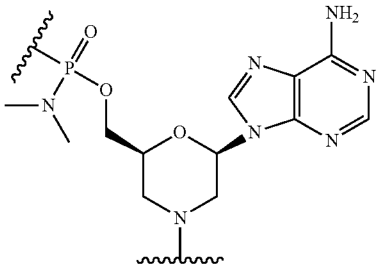 |
| G = 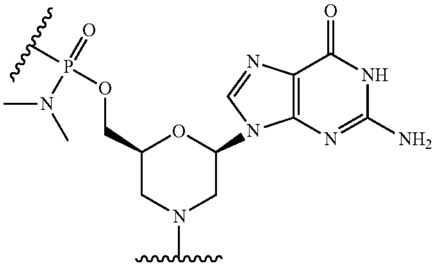 |
| C = 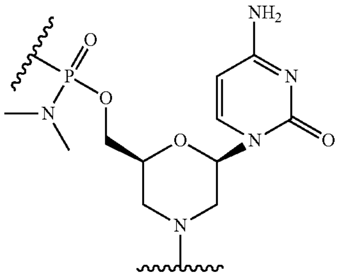 |
| T = 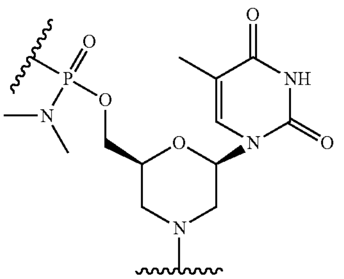 |

TABLE 1-continued

| Various embodiments of morpholino subunits. |
|---|
| 5-Me—C = 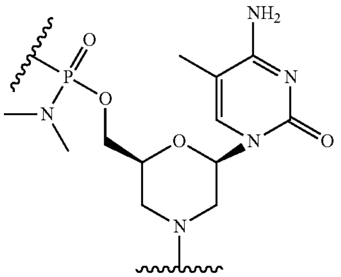 |
| I = 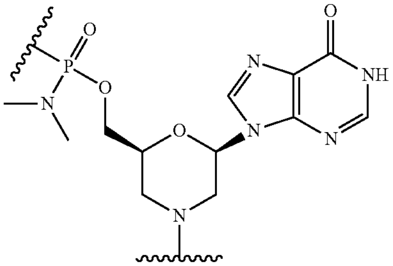 |
| U = 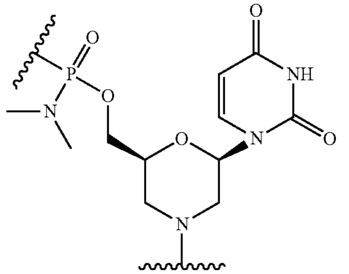 |

EXAMPLES

Examples have been set forth below for the purpose of illustration and to describe certain specific embodiments of the disclosure. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations or methods of the disclosure may be made without departing from the spirit of the disclosure and the scope of the appended claims. Definitions of the variables in the structures in the schemes herein are commensurate with those of corresponding positions in the formulae presented herein.

Example 1: NCP2 Anchor Synthesis

1. Preparation of Methyl 4-Fluoro-3-Nitrobenzoate (1)

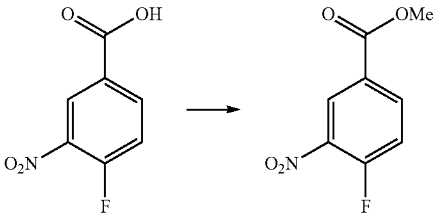

1

To a 100 L flask was charged 12.7 kg of 4-fluoro-3-nitrobenzoic acid was added 40 kg of methanol and 2.82 kg concentrated sulfuric acid. The mixture was stirred at reflux (65° C.) for 36 hours. The reaction mixture was cooled to 0° C. Crystals formed at 38° C. The mixture was held at 0° C. for 4 hrs then filtered under nitrogen. The 100 L flask was washed and filter cake was washed with 10 kg of methanol that had been cooled to 0° C. The solid filter cake was dried on the funnel for 1 hour, transferred to trays, and dried in a vacuum oven at room temperature to a constant weight of 13.695 kg methyl 4-fluoro-3-nitrobenzoate (100% yield; HPLC 99%).

2. Preparation of 3-Nitro-4-(2-oxopropyl)benzoic Acid

A. (Z)-Methyl 4-(3-Hydroxy-1-Methoxy-1-Oxobut-2-en-2-yl)-3-Nitrobenzoate (2)

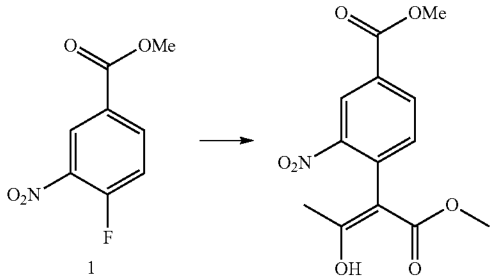

1 2

To a 100 L flask was charged 3.98 kg of methyl 4-fluoro-3-nitrobenzoate (1) from the previous step 9.8 kg DMF, 2.81 kg methyl acetoacetate. The mixture was stirred and cooled to 0° C. To this was added 3.66 kg DBU over about 4 hours while the temperature was maintained at or below 5° C. The mixture was stirred an additional 1 hour. To the reaction flask was added a solution of 8.15 kg of citric acid in 37.5 kg of purified water while the reaction temperature was maintained at or below 15° C. After the addition, the reaction mixture was stirred an addition 30 minutes then filtered under nitrogen. The wet filter cake was returned to the 100 L flask along with 14.8 kg of purified water. The slurry was stirred for 10 minutes then filtered. The wet cake was again returned to the 100 L flask, slurried with 14.8 kg of purified water for 10 minutes, and filtered to crude (Z)-methyl 4-(3-hydroxy-1-methoxy-1-oxobut-2-en-2-yl)-3-nitrobenzoate.

B. 3-Nitro-4-(2-oxopropyl)benzoic Acid

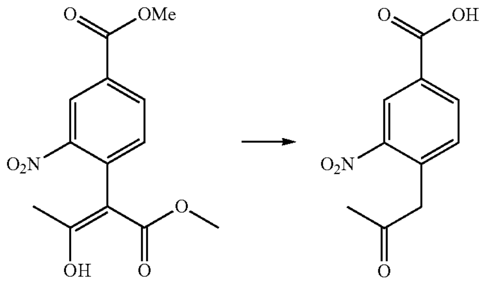

2 3

The crude (Z)-methyl 4-(3-hydroxy-1-methoxy-1-oxobut-2-en-2-yl)-3-nitrobenzoate was charged to a 100 L reaction flask under nitrogen. To this was added 14.2 kg 1,4-dioxane and the stirred. To the mixture was added a solution of 16.655 kg concentrated HCl and 13.33 kg purified water (6M HCl) over 2 hours while the temperature of the reaction mixture was maintained below 15° C. When the addition was complete, the reaction mixture was heated at reflux (80° C.) for 24 hours, cooled to room temperature, and filtered under nitrogen. The solid filter cake was triturated with 14.8 kg of purified water, filtered, triturated again with 14.8 kg of purified water, and filtered. The solid was returned to the 100 L flask with 39.9 kg of DCM and refluxed with stirring for 1 hour. 1.5 kg of purified water was added to dissolve the remaining solids. The bottom organic layer was split to a pre-warmed 72 L flask, then returned to a clean dry 100 L flask. The solution was cooled to 0° C., held for 1 hour, then filtered. The solid filter cake was washed twice each with a solution of 9.8 kg DCM and 5 kg heptane, then dried on the funnel. The solid was transferred to trays and dried to a constant weight of 1.855 kg 3-Nitro-4-(2-oxopropyl)benzoic Acid. Overall yield 42% from compound 1. HPLC 99.45%.

3. Preparation of N-Tritylpiperazine Succinate (NTP)

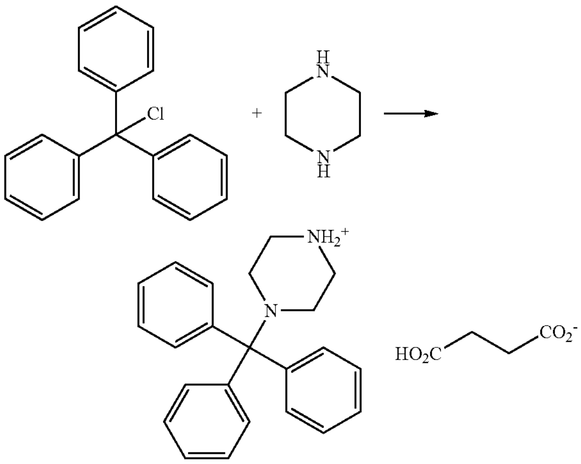

To a 72 L jacketed flask was charged under nitrogen 1.805 kg triphenylmethyl chloride and 8.3 kg of toluene (TPC solution). The mixture was stirred until the solids dissolved. To a 100 L jacketed reaction flask was added under nitrogen 5.61 kg piperazine, 19.9 kg toluene, and 3.72 kg methanol. The mixture was stirred and cooled to 0° C. To this was slowly added in portions the TPC solution over 4 hours while the reaction temperature was maintained at or below 10° C. The mixture was stirred for 1.5 hours at 10° C., then allowed to warm to 14° C. 32.6 kg of purified water was charged to the 72 L flask, then transferred to the 100 L flask while the internal batch temperature was maintained at 20+/−5° C. The layers were allowed to split and the bottom aqueous layer was separated and stored. The organic layer was extracted three times with 32 kg of purified water each, and the aqueous layers were separated and combined with the stored aqueous solution.

The remaining organic layer was cooled to 18° C. and a solution of 847 g of succinic acid in 10.87 kg of purified water was added slowly in portions to the organic layer. The mixture was stirred for 1.75 hours at 20+/−5° C. The mixture was filtered, and the solids were washed with 2 kg TBME and 2 kg of acetone then dried on the funnel. The filter cake was triturated twice with 5.7 kg each of acetone and filtered and washed with 1 kg of acetone between triturations. The solid was dried on the funnel, then transferred to trays and dried in a vacuum oven at room temperature to a constant weight of 2.32 kg of NTP. Yield 80%.

4. Preparation of (4-(2-Hydroxypropyl)-3-Nitrophenyl)(4-Tritylpiperazin-1-yl)Methanone

A. Preparation of 1-(2-Nitro-4(4-Tritylpiperazine-1-Carbonyl)Phenyl)Propan-2-one

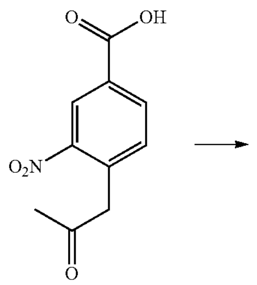

3

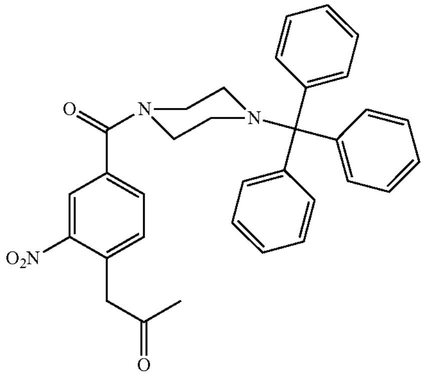

4

To a 100 L jacketed flask was charged under nitrogen 2 kg of 3-Nitro-4-(2-oxopropyl)benzoic Acid (3), 18.3 kg DCM, 1.845 kg N-(3-dimethylaminopropyl)-N'-ethylcarbodiimide hydrochloride (EDC·HCl). The solution was stirred until a homogenous mixture was formed. 3.048 kg of NTP was added over 30 minutes at room temperature and stirred for 8 hours. 5.44 kg of purified water was added to the reaction mixture and stirred for 30 minutes. The layers were allowed to separate and the bottom organic layer containing the product was drained and stored. The aqueous layer was extracted twice with 5.65 kg of DCM. The combined organic layers were washed with a solution of 1.08 kg sodium chloride in 4.08 kg purified water. The organic layers were dried over 1.068 kg of sodium sulfate and filtered. The sodium sulfate was washed with 1.3 kg of DCM. The combined organic layers were slurried with 252 g of silica gel and filtered through a filter funnel containing a bed of 252 g of silica gel. The silica gel bed was washed with 2 kg of DCM. The combined organic layers were evaporated on a rotovap. 4.8 kg of THF was added to the residue and then evaporated on the rotovap until 2.5 volumes of the crude 1-(2-nitro-4(4-tritylpiperazine-1-carbonyl)phenyl)propan-2-one in THE was reached.

B. Preparation of (4-(2-Hydroxypropyl)-3-Nitrophenyl)(4-Tritylpiperazin-1-yl)Methanone (5)

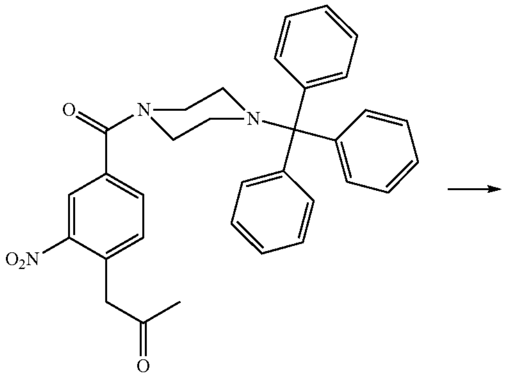

4

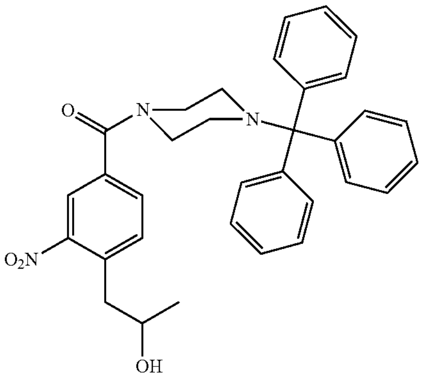

5

To a 100 L jacketed flask was charged under nitrogen 3600 g of 4 from the previous step and 9800 g THF. The stirred solution was cooled to <5° C. The solution was diluted with 11525 g ethanol and 194 g of sodium borohydride was added over about 2 hours at <5° C. The reaction mixture was stirred an additional 2 hours at <5° C. The reaction was quenched with a solution of about 1.1 kg ammonium chloride in about 3 kg of water by slow addition to maintain the temperature at <10° C. The reaction mixture was stirred an additional 30 minutes, filtered to remove inorganics, and recharged to a 100 L jacketed flask and extracted with 23 kg of DCM. The organic layer was separated and the aqueous was twice more extracted with 4.7 kg of DCM each. The combined organic layers were washed with a solution of about 800 g of sodium chloride in about 3 kg of water, then dried over 2.7 kg of sodium sulfate. The suspension was filtered and the filter cake was washed with 2 kg of DCM. The combined filtrates were concentrated to 2.0 volumes, diluted with about 360 g of ethyl acetate, and evaporated. The crude product was loaded onto a silica gel column of 4 kg of silica packed with DCM under nitrogen and eluted with 2.3 kg ethyl acetate in 7.2 kg of DCM. The combined fractions were evaporated and the residue was taken up in 11.7 kg of toluene. The toluene solution was filtered and the filter cake was washed twice with 2 kg of toluene each. The filter cake was dried to a constant weight of 2.275 kf of compound 5 (46% yield from compound 3) HPLC 96.99%.

5. Preparation of 2,5-Dioxopyrrolidin-1-yl(1-(2-Nitro-4-(4-triphenylmethylpiperazine-1 Carbonyl) Phenyl)Propan-2-yl) Carbonate (NCP2 Anchor)

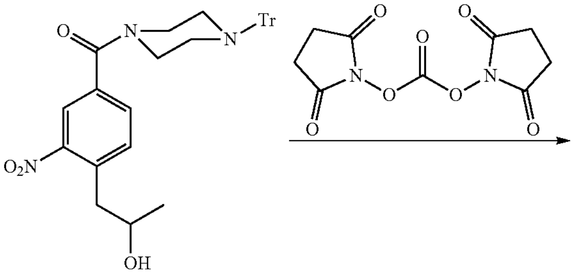

5

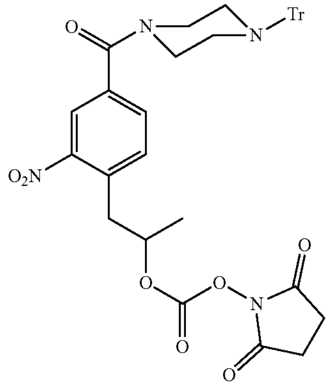

NCP2 Anchor

To a 100 L jacketed flask was charged under nitrogen 4.3 kg of compound 5 (weight adjusted based on residual toluene by $H^1$ NMR; all reagents here after were scaled accordingly) and 12.7 kg pyridine. To this was charged 3.160 kg of DSC (78.91 weight % by $H^1$ NMR) while the internal temperature was maintained at <35° C. The reaction mixture was aged for about 22 hours at ambience then filtered. The filter cake was washed with 200 g of pyridine.

In two batches each comprising 1%2 the filtrate volume, filtrate wash charged slowly to a 100 L jacketed flask containing a solution of about 11 kg of citric acid in about 50 kg of water and stirred for 30 minutes to allow for solid precipitation. The solid was collected with a filter funnel, washed twice with 4.3 kg of water per wash, and dried on the filter funnel under vacuum.

The combined solids were charged to a 100 L jacketed flask and dissolved in 28 kg of DCM and washed with a solution of 900 g of potassium carbonate in 4.3 kg of water. After 1 hour, the layers were allowed to separate and the aqueous layer was removed. The organic layer was washed with 10 kg of water, separated, and dried over 3.5 kg of sodium sulfate. The DCM was filtered, evaporated, and dried under vacuum to 6.16 kg of NCP2 Anchor (114% yield).

Example 2: Anchor Loaded Resin Synthesis

To a 75 L solid phase synthesis reactor with a Teflon stop cock was charged about 52 L of NMP and 2300 g of aminomethyl polystyrene resin. The resin was stirred in the NMP to swell for about 2 hours then drained. The resin was washed twice with about 4 L DCM per wash, then twice with 39 L Neutralization Solution per wash, then twice with 39 L of DCM per wash. The NCP2 Anchor Solution was slowly added to the stirring resin solution, stirred for 24 hours at room temperature, and drained. The resin was washed four times with 39 L of NMP per wash, and six times with 39 L of DCM per wash. The resin was treated and stirred with ½ the DEDC Capping Solution for 30 minutes, drained, and was treated and stirred with the 2nd ½ of the DEDC Capping Solution for 30 minutes and drained. The resin was washed six times with 39 L of DCM per wash then dried in an oven to constant weight of 3573.71 g of Anchor Loaded Resin.

Example 3: Preparation of Activated EG3 Tail

1. Preparation of Trityl Piperazine Phenyl Carbamate 35

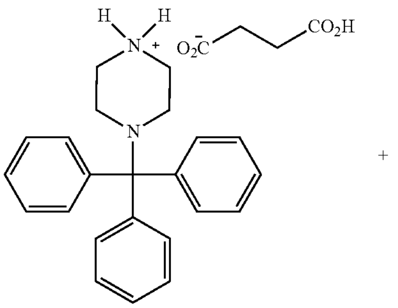

NTP

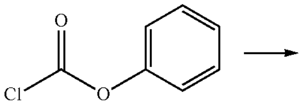

-continued

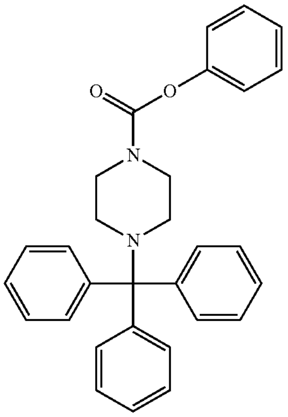

35

To a cooled suspension of NTP in dichloromethane (6 mL/g NTP) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 35 was isolated by crystallization from acetonitrile. Yield=80%

2. Preparation of Carbamate Alcohol 36

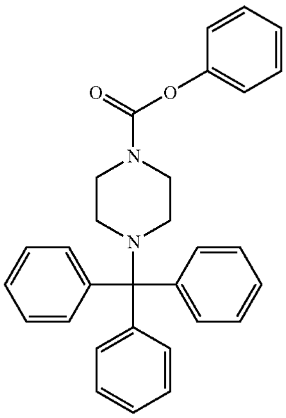

+

35

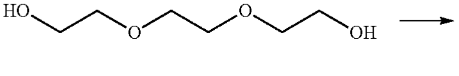

-continued

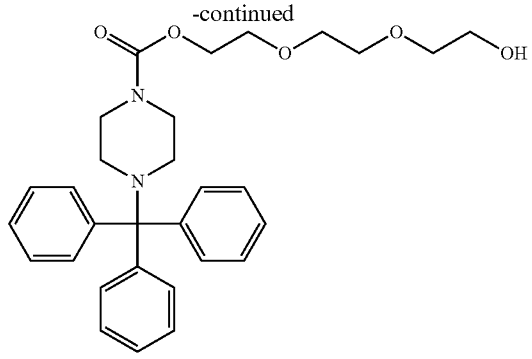

36

Sodium hydride (1.2 eq) was suspended in 1-methyl-2-pyrrolidinone (32 mL/g sodium hydride). To this suspension were added triethylene glycol (10.0 eq) and compound 35 (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 36 was isolated by crystallization from dichloromethane/methyl tert-butyl ether/heptane. Yield=90%.

3. Preparation of EG3 Tail Acid 37

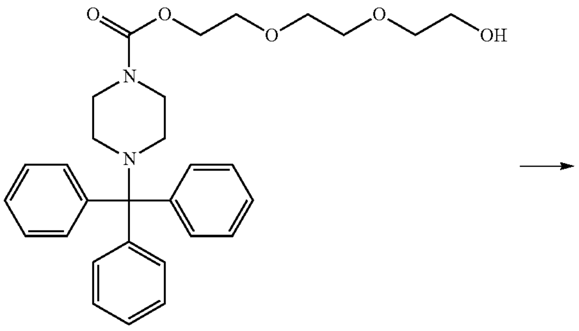

36

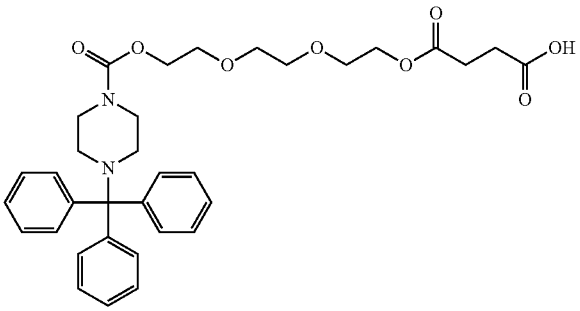

37

To a solution of compound 36 in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous NaHCO3. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 37 was used without isolation in the preparation of compound 38.

4. Preparation of Activated EG3 Tail 38

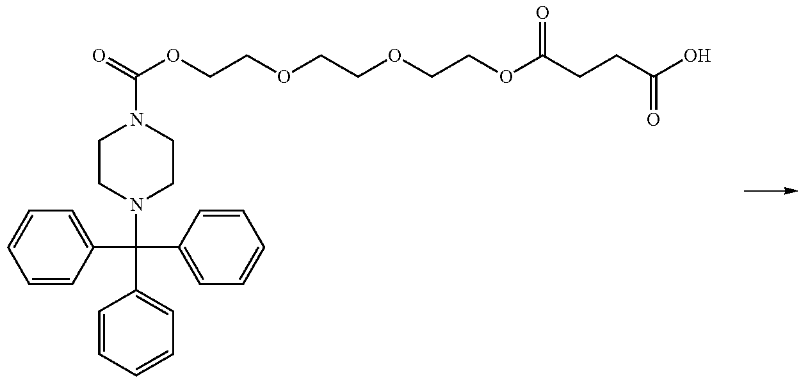

37

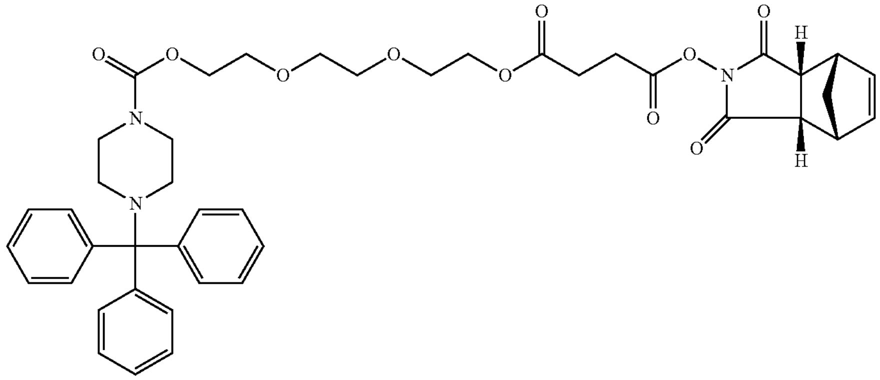

38

To the solution of compound 37 was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts. Yield=70% of Activated EG3 Tail 38 from compound 36.

Example 4: Disulfide Anchor Synthesis

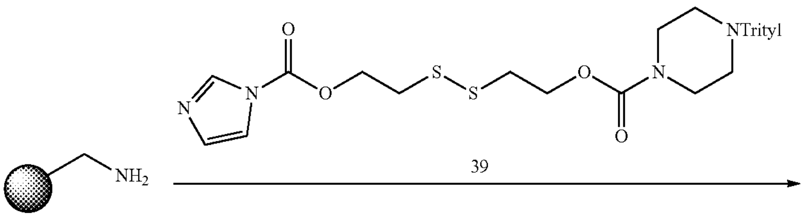

39

-continued

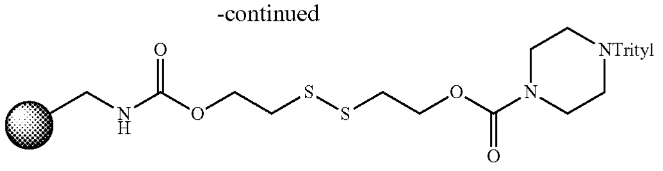

40

To aminomethylpolystyrene resin (100-200 mesh; −1.0 mmol/g N2 substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was fluidized with a solution of disulfide anchor 34 in 1-methyl-2-pyrrolidinone (0.17 M; 15 mL/g resin, −2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 mi) and then washed with dichloromethane (6×1-2 mi). The resin 40 was dried under a N2 stream for 1-3 hr and then under vacuum to constant weight (±20%). Yield: 11010 of the original resin weight.

Example 5: 250 mg Solid-phase Synthesis of Eteplirsen Crude Drug Substance

1. Materials

TABLE 2

| Starting Materials | | | | |
|---|---|---|---|---|
| Material Name | Chemical Name | CAS Number | Chemical Formula | Molecular Weight |
| Activated A Subunit | Phosphoramidochloridic acid, N,N-dimethyl-,[6-[6-(benzoylamino)-9H-purin-9-yl]-4-(triphenylmethyl)-2-morpholinyl]methyl ester | 1155373-30-0 | $C_{38}H_{37}ClN_7O_4P$ | 722.2 |
| Activated C Subunit | Phosphoramidochloridic acid, N,N-dimethyl-,[6-[4-(benzoylamino)-2-oxo-1(2H)-pyrimidinyl]-4-(triphenylmethyl)-2-morpholinyl]methyl ester | 1155373-31-1 | $C_{37}H_{37}ClN_5O_5P$ | 698.2 |
| Activated DPG Subunit | Propanoic Acid, 2,2-dimethyl-,4-[[9-[6-[[[chloro(dimethylamino)phosphinyl]oxy]methyl]-4-(triphenylmethyl)-2-morpholinyl]-2-[(2-phenylacetyl)amino]-9H-purin-6-yl]oxy]methyl]phenyl ester | 1155309-89-9 | $C_{51}H_{53}ClN_7O_7P$ | 942.2 |
| Activated T Subunit | Phosphoramidochloridic acid, N,N-dimethyl-,[6-(3,4-dihydro-5-methyl-2,4-dioxo-1(2H)-pyrimidinyl)]-4-(triphenylmethyl)-2-morpholinyl]methyl ester | 1155373-34-4 | $C_{31}H_{34}ClN_4O_5P$ | 609.1 |
| Activated EG3 Tail | Butanedioic acid, 1-[3aR,4S,7R,7aS)-1,3,3a,4,7,7a-hexahydro-1,3-dioxo-4,7-methano-2H-isoindol-2-yl] 4-[2-[2-[2-[[[4-(triphenylmethyl)-1-piperazinyl]carbonyl]oxy]ethoxy]ethoxy]ethyl] ester | 1380600-06-5 | $C_{43}H_{47}N_3O_{10}$ | 765.9 |

Chemical Structures of Starting Materials:
A. Activated EG3 Tail
Compound (B)
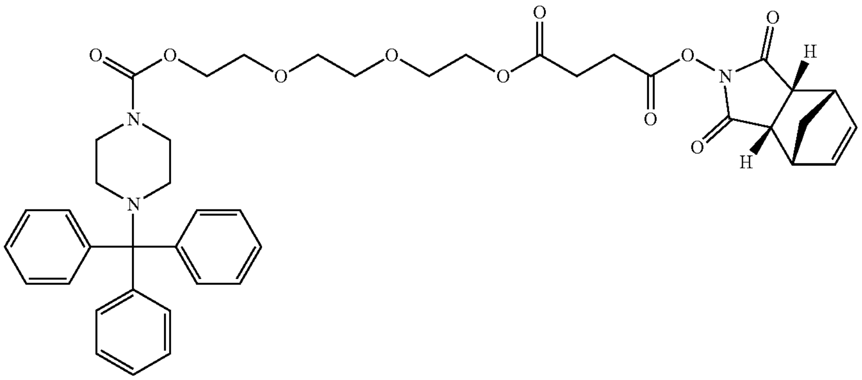
B. Activated C Subunit (for Preparation, See U.S. Pat. No. 8,067,571)
Compound (C1)
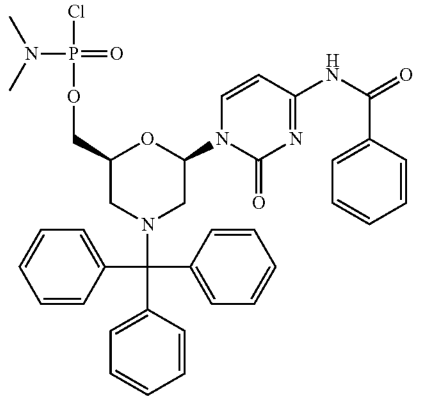
C. Activated a Subunit (for Preparation, See U.S. Pat. No. 8,067,571)
Compound (D1)
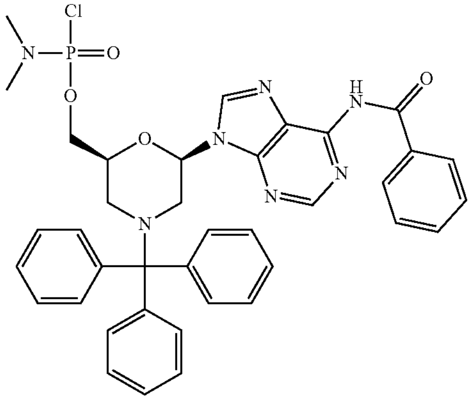
D. Activated DPG Subunit (for Preparation, See WO 2009/064471)
Compound (E1)
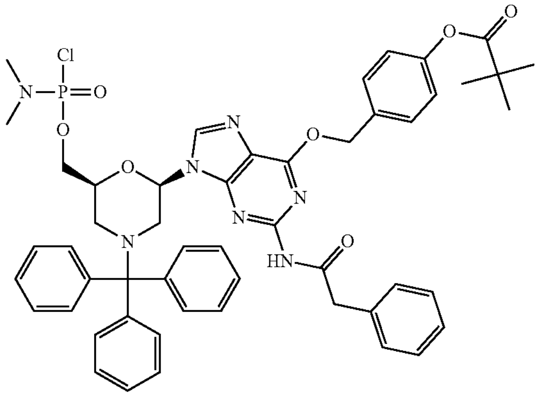
E. Activated T Subunit (for Preparation, See WO 2013/082551)
Compound (F1)
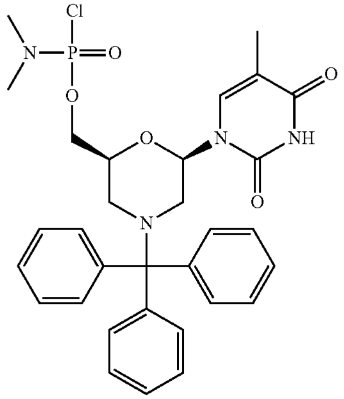

F. Anchor Loaded Resin: NCP2

Formula (G1)

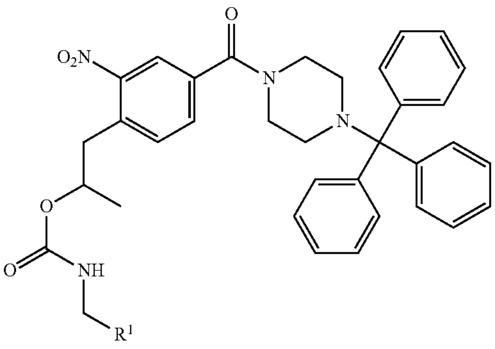

wherein $R^1$ is a support-medium.

G. Anchor Loaded Resin: Disulfide

Formula (H1)

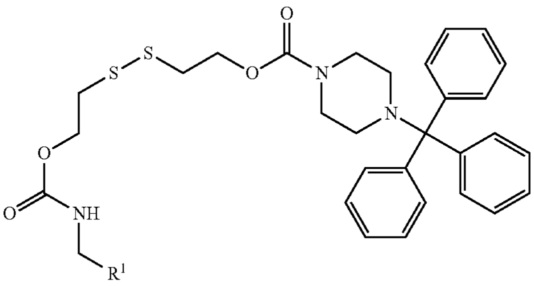

wherein $R^1$ is a support-medium.

TABLE 3

| Description of Solutions for Solid Phase Oligomer Synthesis of Eteplirsen Crude Drug Substance | |
|---|---|
| Solution Name | Solution Composition |
| NCP2 Anchor Solution | 12.5 mL NMP and 430 mg NCP2 Anchor |
| DEDC Capping Solution | 1.4 mL Diethyl Dicarbonate (DEDC), 1.2 mL NEM, and 11.2 mL DCM |
| CYTFA Solution | 667 mg 4-cyanopyridine, 52.6 mL DCM, 1.2 mL TFA, 13 mL TFE, and 0.7 mL purified water |
| Neutralization Solution | 11.7 mL IPA, 2.4 mL DIPEA, and 35.4 mL DCM |
| Cleavage Solution | 509 mg DTT, 2.3 mL NMP, and 1.0 mL DBU |

2. Synthesis of Residues 1-10 of Eteplirsen Crude Drug Substance

A. Resin Swelling 250 mg of Anchor Loaded Resin and NMP were charged to a silanized reactor and stirred for 3 hours. The NMP was drained and the Anchor Loaded Resin was washed twice with DCM and five times with 30% TFE/DCM.

B. Cycle 0: EG3 Tail Coupling

The Anchor Loaded Resin was washed three times with 30% TFE/DCM and drained, washed with CYTFA solution for 15 minutes and drained, and again washed with CYTFA Solution for 15 minutes without draining to which a 1:1 NEM/DCM was charged and the suspension stirred for 2 minutes and drained. The resin was washed twice with Neutralization Solution for 5 minutes and drained, then twice with each of DCM and drained. A solution of activated EG3 Tail and NEM in DMI was charged to the resin and stirred for 3 hours at RT and drained. The resin was washed twice with Neutralization Solution for 5 minutes per each wash, and once with DCM and drained. A solution of benzoic anhydride and NEM in NMP was charged and stirred for 15 minutes and drained. The resin was stirred with Neutralization Solution for 5 minutes, then washed once with DCM and twice with 30% TFE/DCM. The resin was suspended in 30% TFE/DCM and held for 14 hours.

C. Subunit Coupling Cycles 1-10 i. Pre-Coupling Treatments

Prior to each coupling cycle as described in Table 4, the resin was: 1) washed with 30% TFE/DCM; 2) a) treated with CYTFA Solution 15 minutes and drained, and b) treated with CYTFA solution for 15 minutes to which was added 1:1 NEM/DCM, stirred, and drained; 3) stirred three times with Neutralization Solution; and 4) washed twice with DCM. See Table 4.

ii. Post Coupling Treatments

After each subunit solution was drained as described in Table 4, the resin was: 1) washed with DCM; and 2) washed two times with 30% TFE/DCM. If the resin was held for a time period prior to the next coupling cycle, the second TFE/DCM wash was not drained and the resin was retained in said TFE/DCM wash solution. See Table 4.

iii. Activated Subunit Coupling Cycles

The coupling cycles were performed as described in Table 4.

iv. Final IPA Washing

After the final coupling step was performed as described in Table 4, the resin was washed 8 times with IPA, and dried under vacuum at room temperature for about 63.5 hours to a dried weight of 1.86 g.

D. Cleavage

The above resin bound Eteplisen Crude Drug Substance was divided into two lots, each lot was treated as follows. A 929 mg lot of resin was: 1) stirred with NMP for 2 hrs, then the NMP was drained; 2) washed tree times with of 30% TFE/DCM; 3) treated with CYTFA Solution for 15 minutes; and 4) CYTFA Solution for 15 minutes to which a 1:1 solution of NEM/DCM was then added and stirred for 2 minutes and drained. The resin was treated three times with Neutralization Solution, washed six times with DCM, and eight times with NMP. The resin was treated with a Cleaving Solution of 510 mg DTT and 992 mg DBU in 2.3 mL NMP for 2 hours to detach the Eteplisen Crude Drug Substance from the resin. The Cleaving solution was drained and retained in a separate vessel. The reactor and resin were washed with 1.6 mL of NMP which was combined with the Cleaving Solution.

TABLE 4

| Cycle No.: Subunit (SU) | Pre-coupling Treatment: 1 30% TFE/DCM Wash | Pre-coupling Treatment: 2 CYTFA Sln.[1] | Pre-coupling Treatment: 3 Neutralization Solution | Pre-coupling Treatment: 4 DCM Wash | Coupling Cycle: Quantity SU NEM DMI LiBr | Coupling Cycle: RT Coupling Time (Hrs.) | Post-Coupling Treatment: 1 DCM Wash | Post-Coupling Treatment: 2 30% TFE/DCM Wash |
|---|---|---|---|---|---|---|---|---|
| 1:C | 1.8 mL | a) 1.8 mL b) 1.8 mL, 0.041 ml | 3 × 1.8 mL | 1.8 mL | 179 mg; 0.065 ml NEM; 1.0 mL DMI; 111 mg LiBr | 5 | 1.8 mL | 2 × 1.8 mL |
| 2:T | 2.3 mL | a) 2.3 mL b) 2.3 mL, 0.053 ml | 3 × 2.3 mL | 2 × 2.3 mL | 156 mg and 0.065 ml NEM 1.0 mL DMI; 111 mg LiBr | 4.25 | 2.3 mL | 2 × 2.3 mL |
| 3:C | 2.7 mL | a) 2.7 mL b) 2.7 mL, 0.061 ml | 3 × 2.7 mL | 2 × 2.7 mL | 179 mg; 0.065 ml NEM; 1.0 mL DMI; 111 mg LiBr | 4.25 | 2.7 mL | 2 × 2.7 mL |
| 4:C | 3.0 mL | a) 3.0 mL b) 3.0 mL, 0.069 ml | 3 × 3.0 mL | 2 × 3.0 mL | 179 mg; 0.065 ml NEM; 1.0 mL DMI; 111 mg LiBr | 4.25 | 3.0 mL | 2 × 3.0 mL |
| 5:A | 3.2 mL | a) 3.2 mL b) 3.2 mL, 0.073 ml | 3 × 3.2 mL | 2 × 9.5 mL | 185 mg; 0.064 ml NEM; 1.1 mL DMI; 111 mg LiBr | 4.25 | 3.2 mL | 2 × 3.2 mL |
| 6:A | 3.3 mL | a) 3.3 mL b) 3.3 mL, 0.078 ml | 3 × 3.3 mL | 2 × 3.3 mL | 185 mg; 0.064 ml NEM; 1.1 mL DMI; 111 mg LiBr | 4.25 | 3.3 mL | 2 × 3.3 mL |

| Cycle No.: Subunit (SU) | Pre-coupling Treatment: 1 30% TFE/DCM Wash | Pre-coupling Treatment: 2 CYTFA Sln. | Pre-coupling Treatment: 3 Neutralization Solution | Pre-coupling Treatment: 4 DCM Wash | Coupling Cycle: Quantity SU (g) NEM (L) DMI (L) | Coupling Cycle: RT Coupling Time (Hrs.) | Post-Coupling Treatment: 1 DCM Wash | Post-Coupling Treatment: 2 30% TFE/DCM Wash |
|---|---|---|---|---|---|---|---|---|
| 7:C | 3.6 mL | a) 3.6 mL b) 3.6 mL, 0.085 ml | 3 × 3.6 mL | 2 × 3.6 mL | 179 mg; 0.065 ml NEM; 1.0 mL DMI; 111 mg LiBr | 4.25 | 3.6 mL | 2 × 3.6 mL |
| 8:A | 3.6 mL | a) 3.6 mL b) 3.6 mL, 0.085 ml | 3 × 3.6 mL | 2 × 3.6 mL | 185 mg; 0.064 ml NEM; 1.1 mL DMI; 111 mg LiBr | 4.25 | 3.6 mL | 2 × 3.6 mL |
| 9:T | 3.8 mL | a) 3.8 mL b) 3.8 mL 0.089 ml | 3 × 3.8 mL | 2 × 3.8 mL | 156 mg and 0.065 ml NEM 1.0 mL DMI; 111 mg LiBr | 4.25 | 3.8 mL | 2 × 3.8 mL |
| 10:C | 4.0 mL | a) 4.0 mL b) 4.0 mL, 280 ml | 3 × 4.0 mL | 2 × 4.0 mL | 179 mg; 0.065 ml NEM; 1.0 mL DMI; 111 mg LiBr | 4.25 | 4.0 mL | 2 × 4.0 mL |

[1]ml indicates the amount of 1:1 NEM/DCM

E. Deprotection

The combined Cleaving Solution and NMIP wash were transferred to a pressure vessel to which was added 13.3 mL of $NH_4OH$ ($NH_3 \cdot H_2O$) that had been chilled to a temperature of −10° to −25° C. in a freezer. The pressure vessel was sealed and heated to 45° C. for 16 hrs then allowed to cool to 25° C. This deprotection solution containing the Eteplirsen crude drug substance was diluted 3:1 with purified water and pH adjusted to 3.0 with 2M phosphoric acid, then to pH 8.03 with $NH_4OH$.

3. Synthesis of Eteplirsen Crude Drug Substance

Eteplirsen can be synthetized using steps A-E as described in Example 5, part 2, and using the information given in Table 5 below.

TABLE 5

| | Pre-coupling Treatment | | | | Coupling Cycle Quantity | | Post-Coupling Treatment | |
|---|---|---|---|---|---|---|---|---|
| Cycle No.: Subunit (SU) | 1 30% TFE/DCM Wash | 2 CYTFA Sln.[2] | 3 Neutralization Solution | 4 DCM Wash | SU NEM DMI LiBr | RT Coupling Time (Hrs.) | 1 DCM Wash | 2 30% TFE/DCM Wash |
| 1:C | 1.8 mL | a)<br>1.8 mL<br>b)<br>1.8 mL,<br>0.041 ml | 3 × 1.8 mL | 1.8 mL | 179 mg;<br>0.065 ml NEM;<br>1.0 mL DMI;<br>111 mg LiBr | 5 | 1.8 mL | 2 × 1.8 mL |
| 2:T | 2.3 mL | a)<br>2.3 mL<br>b)<br>2.3 mL,<br>0.053 ml | 3 × 2.3 mL | 2 × 2.3 mL | 156 mg and<br>0.065 ml NEM<br>1.0 mL DMI;<br>111 mg LiBr | 4.25 | 2.3 mL | 2 × 2.3 mL |
| 3:C | 2.7 mL | a)<br>2.7 mL<br>b)<br>2.7 mL,<br>0.061 ml | 3 × 2.7 mL | 2 × 2.7 mL | 179 mg;<br>0.065 ml NEM;<br>1.0 mL DMI;<br>111 mg LiBr | 4.25 | 2.7 mL | 2 × 2.7 mL |
| 4:C | 3.0 mL | a)<br>3.0 mL<br>b)<br>3.0 mL,<br>0.069 ml | 3 × 3.0 mL | 2 × 3.0 mL | 179 mg;<br>0.065 ml NEM;<br>1.0 mL DMI;<br>111 mg LiBr | 4.25 | 3.0 mL | 2 × 3.0 mL |
| 5:A | 3.2 mL | a)<br>3.2 mL<br>b)<br>3.2 mL,<br>0.073 ml | 3 × 3.2 mL | 2 × 9.5 mL | 185 mg;<br>0.064 ml NEM;<br>1.1 mL DMI;<br>111 mg LiBr | 4.25 | 3.2 mL | 2 × 3.2 mL |
| 6:A | 3.3 mL | a)<br>3.3 mL<br>b)<br>3.3 mL,<br>0.078 ml | 3 × 3.3 mL | 2 × 3.3 mL | 185 mg;<br>0.064 ml NEM;<br>1.1 mL DMI;<br>111 mg LiBr | 4.25 | 3.3 mL | 2 × 3.3 mL |

| | Pre-coupling Treatment | | | | Coupling Cycle Quantity SU (g) | | Post-Coupling Treatment | |
|---|---|---|---|---|---|---|---|---|
| Cycle No.: Subunit (SU) | 1 30% TFE/DCM Wash | 2 CYTFA Solution | 3 Neutralization Solution | 4 DCM Wash | NEM (L) DMI (L) | RT Coupling Time (Hrs.) | 1 DCM Wash | 2 30% TFE/DCM Wash |
| 7:C | 3.6 mL | a)<br>3.6 mL<br>b)<br>3.6 mL,<br>0.085 ml | 3 × 3.6 mL | 2 × 3.6 mL | 179 mg;<br>0.065 ml NEM;<br>1.0 mL DMI;<br>111 mg LiBr | 4.25 | 3.6 mL | 2 × 3.6 mL |
| 8:A | 3.6 mL | a)<br>3.6 mL<br>b)<br>3.6 mL,<br>0.085 ml | 3 × 3.6 mL | 2 × 3.6 mL | 185 mg;<br>0.064 ml NEM;<br>1.1 mL DMI;<br>111 mg LiBr | 4.25 | 3.6 mL | 2 × 3.6mL |
| 9:T | 3.8 mL | a)<br>3.8 mL<br>b)<br>3.8 mL<br>0.089 ml | 3 × 3.8 mL | 2 × 3.8 mL | 156 mg and<br>0.065 ml NEM<br>1.0 mL DMI;<br>111 mg LiBr | 4.25 | 3.8 mL | 2 × 3.8mL |
| 10:C | 4.0 mL | a)<br>4.0 mL<br>b)<br>4.0 mL,<br>280 ml | 3 × 4.0 mL | 2 × 4.0 mL | 179 mg;<br>0.065 ml NEM;<br>1.0 mL DMI;<br>111 mg LiBr | 4.25 | 4.0 mL | 2 × 4.0 mL |
| 11:A | 4.5 mL | a)<br>4.5 mL<br>b)<br>4.5 mL,<br>0.068 ml | 3 × 4.5 mL | 2 × 4.5 mL | 185 mg;<br>0.064 ml NEM;<br>1.1 mL DMI;<br>111 mg LiBr | 4.25 | 4.5 mL | 2 × 4.5 mL |

TABLE 5-continued

| | | | | | | | | |
|---|---|---|---|---|---|---|---|---|
| 12:A | 4.5 mL | a) 4.5 mL b) 4.5 mL, 0.068 ml | 3 × 4.5 mL | 2 × 4.5 mL | 185 mg; 0.064 ml NEM; 1.1 mL DMI; 111 mg LiBr | 4.25 | 4.5 mL | 2 × 4.5 mL |
| 13:DPG | 4.6 mL | a) 4.6 mL b) 4.6 mL, 0.072 ml | 3 × 4.6 mL | 2 × 4.6 mL | 313 mg; 0.084 ml NEM; 1.3 mL DMI; 111 mg LiBr | 4.25 | 4.6 mL | 2 × 4.6 mL |
| 14:DPG | 4.8 mL | a) 4.8 mL b) 4.8 mL, 0.76 ml | 3 × 4.8 mL | 2 × 4.8 mL | 313 mg; 0.084 ml NEM; 1.3 mL DMI; 111 mg LiBr | 4.25 | 4.8 mL | 2 × 4.8 mL |
| 15:A | 5.2 mL | a) 5.2 mL b) 5.2 mL, 0.085 ml | 3 × 5.2 mL | 2 × 5.2 mL | 185 mg; 0.064 ml NEM; 1.1 mL DMI; 111 mg LiBr | 4.25 | 5.2 mL | 2 × 5.2 mL |
| 16:A | 5.2 mL | a) 5.2 mL b) 5.2 mL, 0.085 ml | 3 × 5.2 mL | 2 × 5.2 mL | 185 mg; 0.064 ml NEM; 1.1 mL DMI; 111 mg LiBr | 4.25 | 5.2 mL | 2 × 5.2 mL |
| 17:DPG | 5.3 mL | a) 5.3 mL b) 5.3 mL, 0.121 ml | 3 × 5.3 mL | 2 × 5.3 mL | 313 mg; 0.084 ml NEM; 1.3 mL DMI; 111 mg LiBr | 4.75 | 5.3 mL | 2 × 5.3 mL |
| 18:A | 5.5 mL | a) 5.5 mL b) 5.5 mL, 0.126 ml | 3 × 5.5 mL | 2 × 5.5 mL | 185 mg; 0.064 ml NEM; 1.1 mL DMI; 111 mg LiBr | 4.25 | 5.5 mL | 2 × 5.5 mL |
| 19:T | 5.5 mL | a) 5.5 mL b) 5.5 mL, 0.126 ml | 5.5 mL | 2 × 5.5 mL | 156 mg and 0.065 ml NEM 1.0 mL DMI; 111 mg LiBr | 4.25 | 5.5 mL | 2 × 5.5 mL |
| 20:DPG | 5.7 mL | a) 5.7 mL b) 5.7 mL, 0.130 ml | 3 × 5.7 mL | 2 × 5.7 mL | 313 mg; 0.084 ml NEM; 1.3 mL DMI; 111 mg LiBr | 4.75 | 5.7 mL | 2 × 5.7 mL |
| 21:DPG | 5.7 mL | a) 5.7 mL b) 5.7 mL, 0.130 ml | 3 × 5.7 mL | 2 × 5.7 mL | 313 mg; 0.084 ml NEM; 1.3 mL DMI; 111 mg LiBr | 4.25 | 5.7 mL | 2 × 5.7 mL |
| 22:C | 5.8 mL | a) 5.8 mL b) 5.8 mL, 0.134 ml | 3 × 5.8 mL | 2 × 5.8mL | 179 mg; 0.065 ml NEM; 1.0 mL DMI; 111 mg LiBr | 4.75 | 5.8 mL | 2 × 5.8 mL |
| 23:A | 5.8 mL | a) 5.8 mL b) 5.8 mL, 0.134 ml | 3 × 5.8 mL | 2 × 5.8 mL | 185 mg; 0.064 ml NEM; 1.1 mL DMI; 111 mg LiBr | 4.25 | 5.8 mL | 2 × 5.8 mL |
| 24:T | 6.0 mL | a) 6.0 mL b) 6.0 mL, 0.138 ml | 3 × 6.0 mL | 2 × 6.0 mL | 156 mg and 0.065 ml NEM 1.0 mL DMI; 111 mg LiBr | 4.25 | 6.0 mL | 2 × 6.0 mL |
| 25:T | 6.0 mL | a) 6.0 mL b) 6.0 mL, 0.138 ml | 3 × 6.0 mL | 2 × 6.0 mL | 156 mg and 0.065 ml NEM 1.0 mL DMI; 111 mg LiBr | 4.25 | 6.0 mL | 2 × 6.0 mL |
| 26:T | 6.2 mL | a) 6.2 mL b) 6.2 mL, 0.141 ml | 3 × 6.2 mL | 2 × 6.2 mL | 156 mg and 0.065 ml NEM 1.0 mL DMI; 111 mg LiBr | 4.25 | 6.2 mL | 2 × 6.2 mL |
| 27:C | 6.2 mL | a) 6.2 mL b) 6.2 mL, 0.141 ml | 6.2 mL | 2 × 6.2 mL | 179 mg; 0.065 ml NEM; 1.0 mL DMI; 111 mg LiBr | 4.25 | 6.2 mL | 2 × 6.2 mL |

TABLE 5-continued

| | | | | | | | | |
|---|---|---|---|---|---|---|---|---|
| 28:T | 6.3 mL | a) 6.3 mL b) 6.3 mL, 0.146 ml | 3 × 6.3 mL | 2 × 6.3 mL | 156 mg and 0.065 ml NEM 1.0 mL DMI; 111 mg LiBr | 4.25 | 6.3 mL | 2 × 6.3 mL |
| 29:A | 6.3 mL | a) 6.3 mL b) 6.3 mL, 0.146 ml | 3 × 6.3 mL | 2 × 6.3 mL | 185 mg; 0.064 ml NEM; 1.1 mL DMI; 111 mg LiBr | 4.25 | 6.3 mL | 2 × 6.3 mL |
| 30:DPG | 6.5 mL | a) 6.5 mL b) 6.5 mL, 0.15 ml | 3 × 6.5 mL | 2 × 6.5 mL | 313 mg; 0.084 ml NEM; 1.3 mL DMI; 111 mg LiBr | 4.75 | 6.5 mL | 2 × 6.5 mL |

[2]ml indicates the amount of 1:1 NEM/DCM

Example 6: Design of Flow Synthesizer

Figure 4:
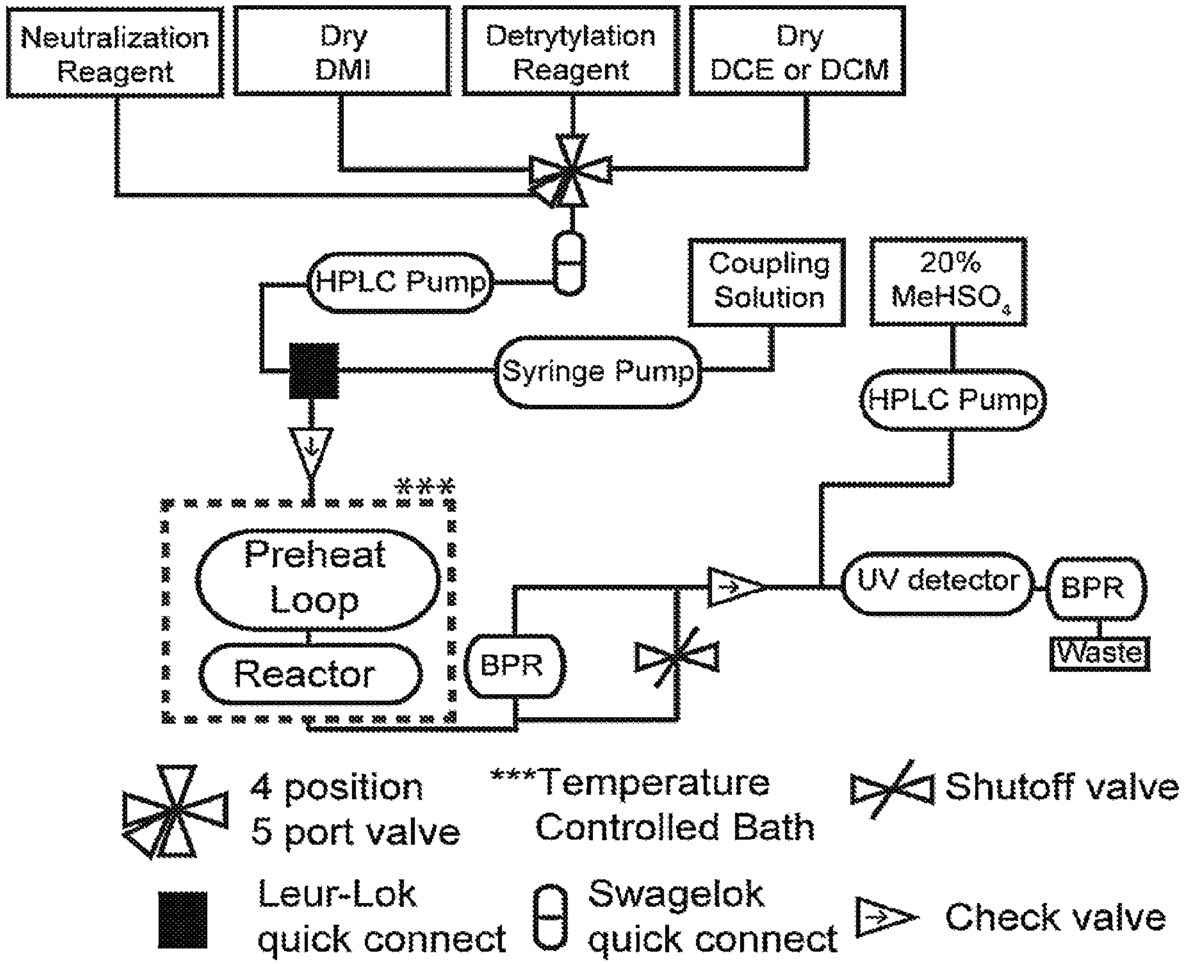
Figure 5A:
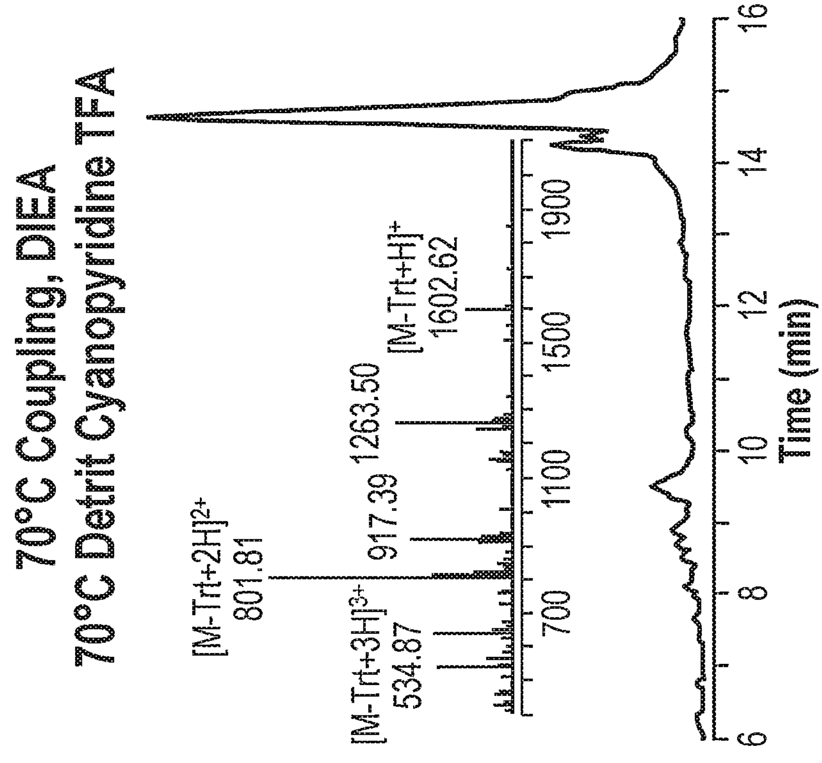
FIG. 5A, FIG. 5B, FIG. 5C, FIG. 5D, and FIG. 5E show the total ion chromatogram for the synthesis of model tetramer 5'-Tail-ACGT-3'-Trt.
Figure 5B:
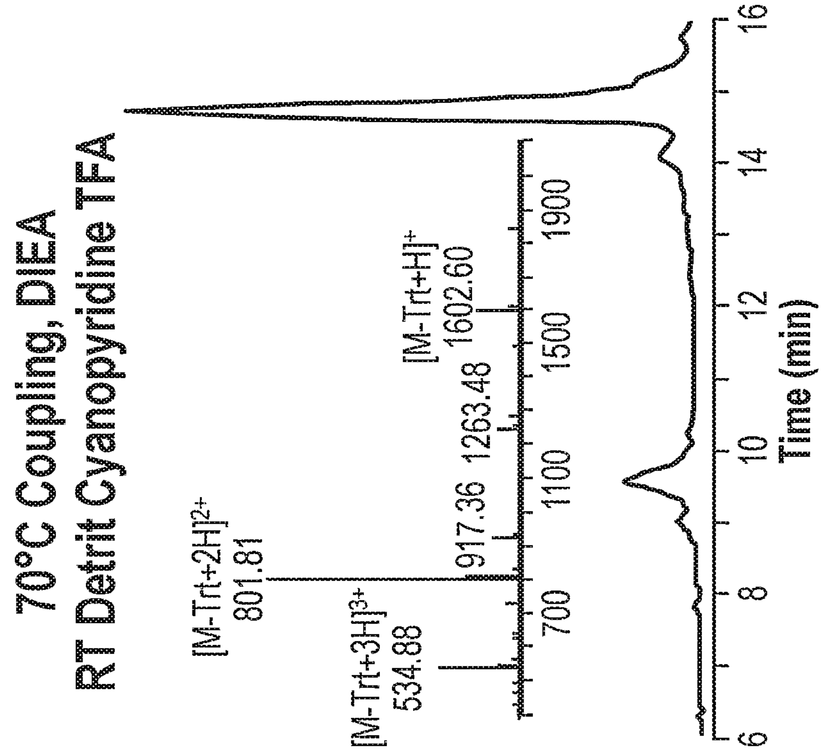
Figure 5D:
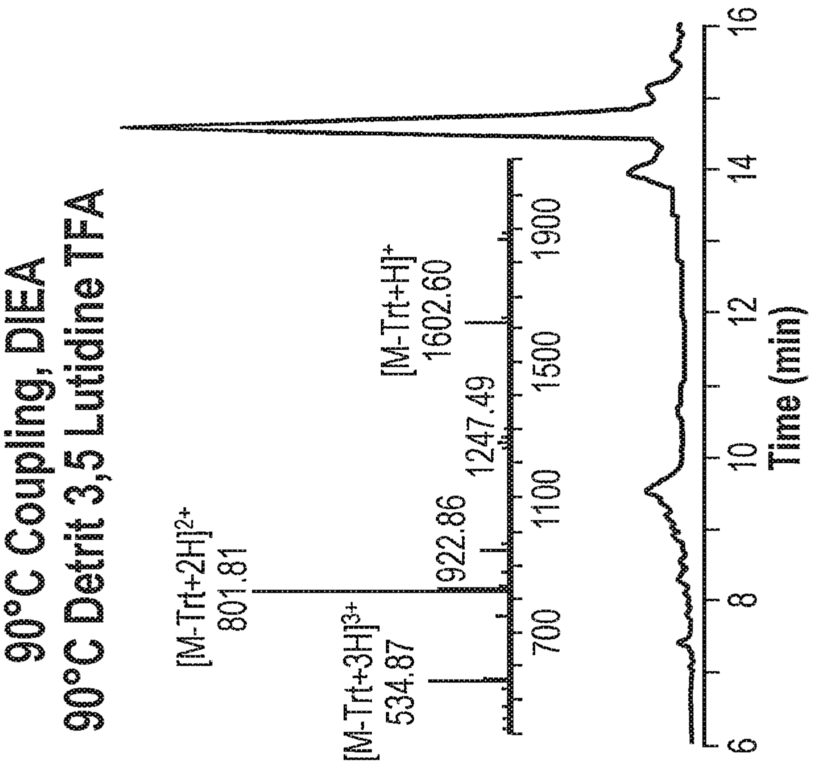
Figure 5C:
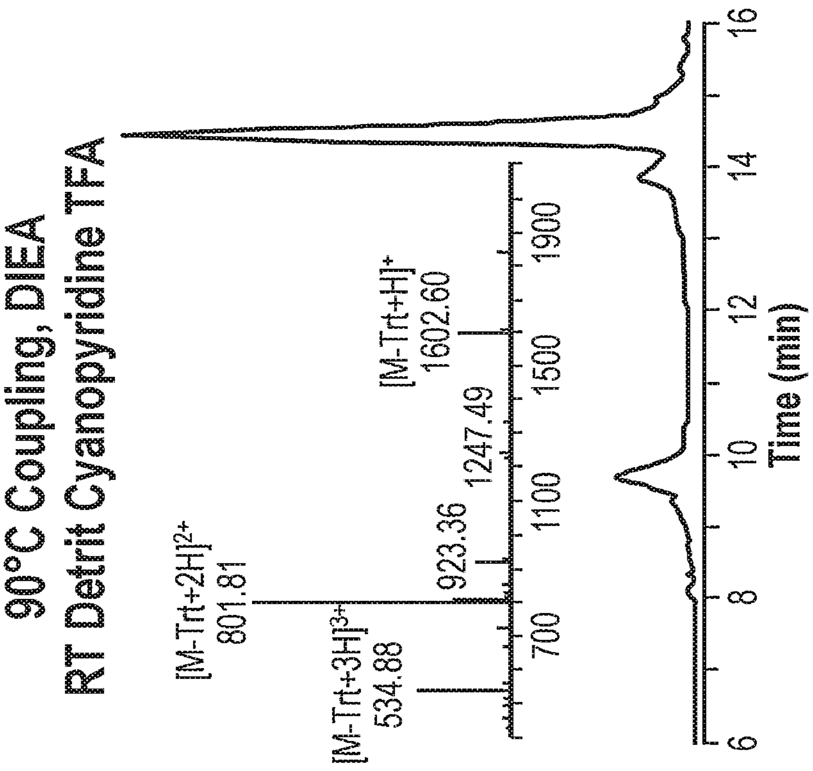
Figure 5E:
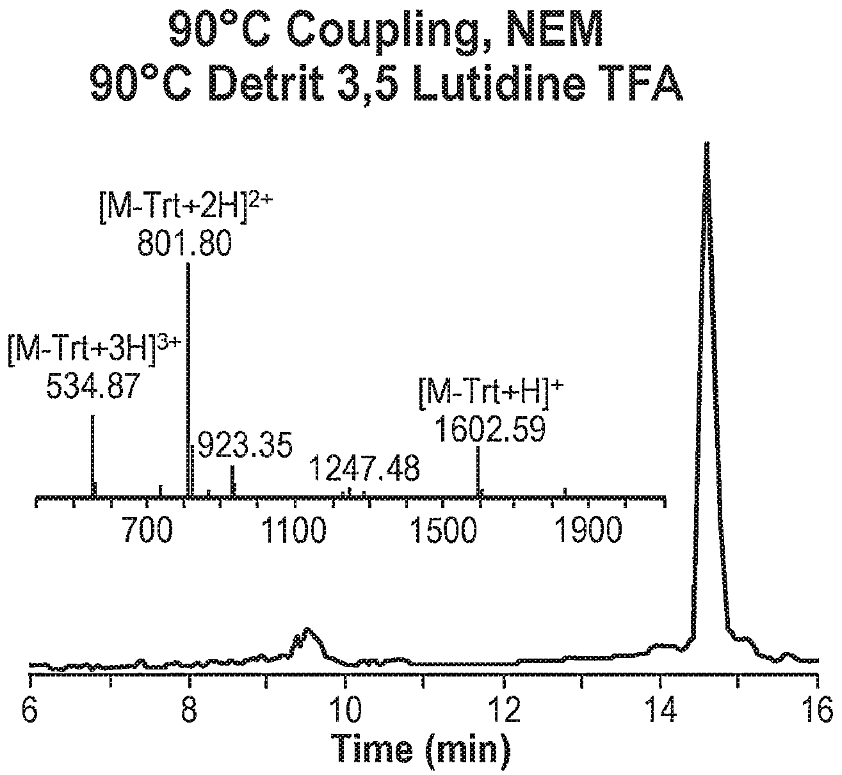
Figure 6A:
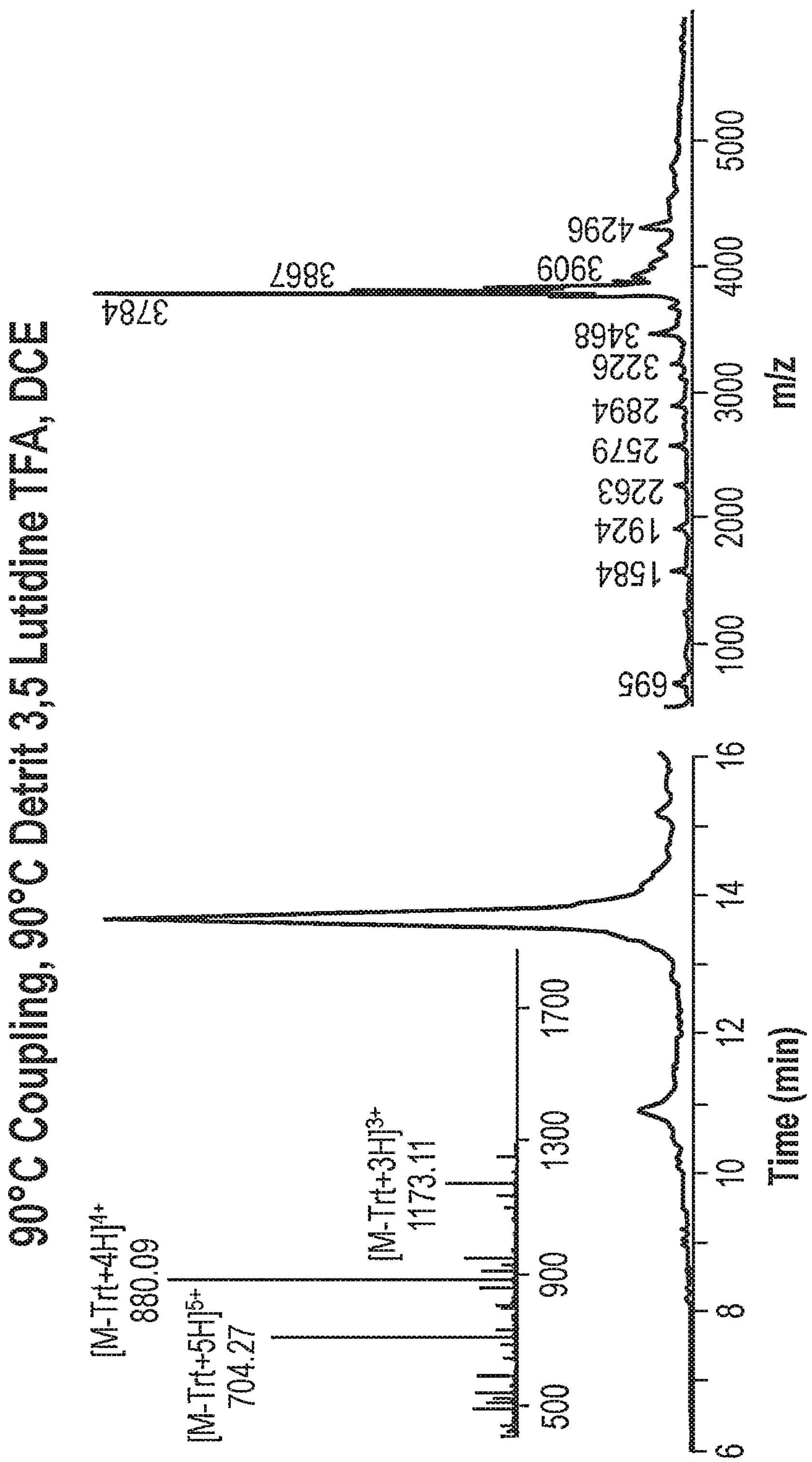
FIG. 6A, FIG. 6B, FIG. 6C, FIG. 6D, and FIG. 6E show the total ion chromatogram for the synthesis of eteplirsen (1-10). MALDI-TOF mass spectra are also shown.
Figure 6B:
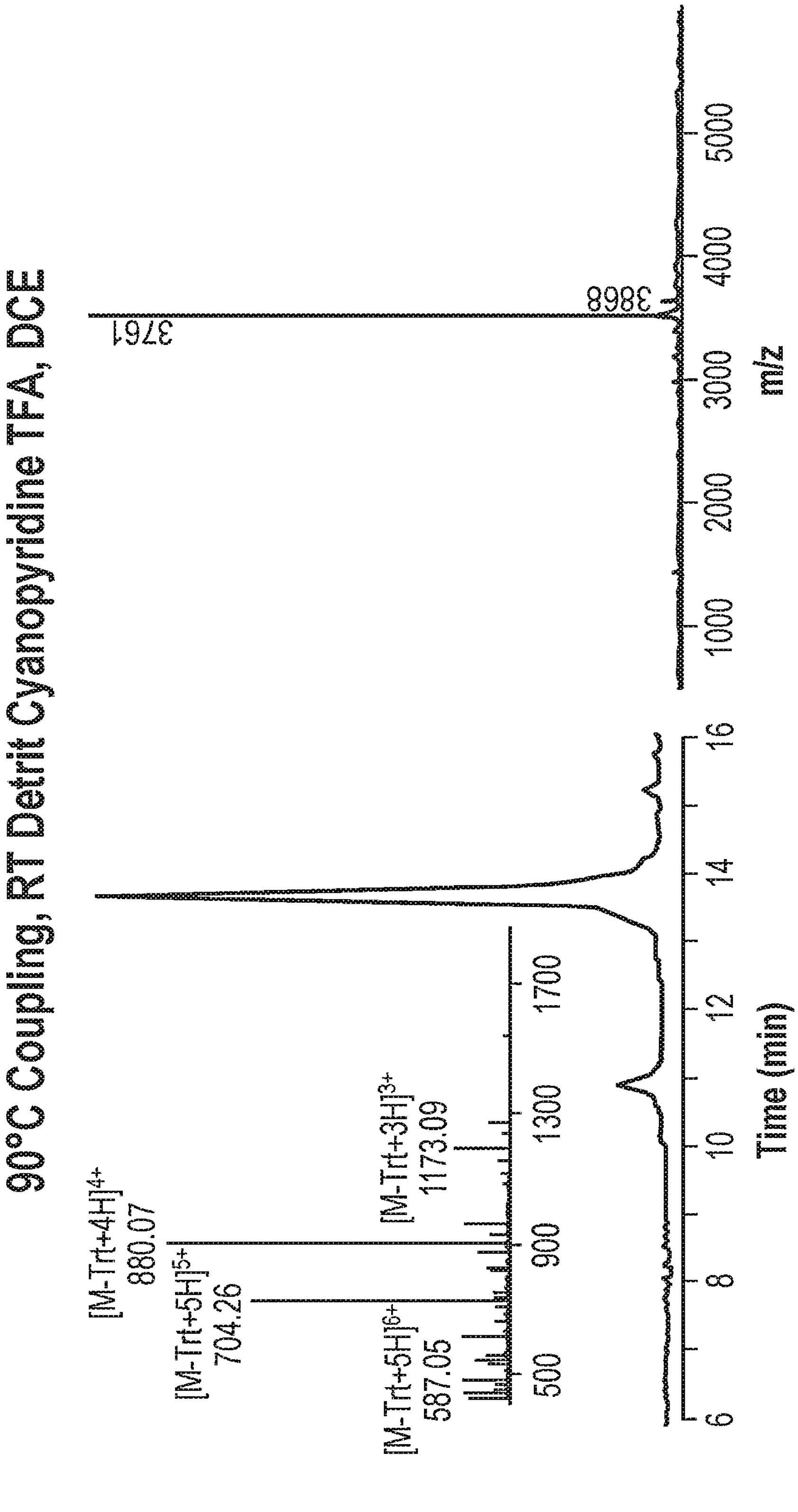
Figure 6C:
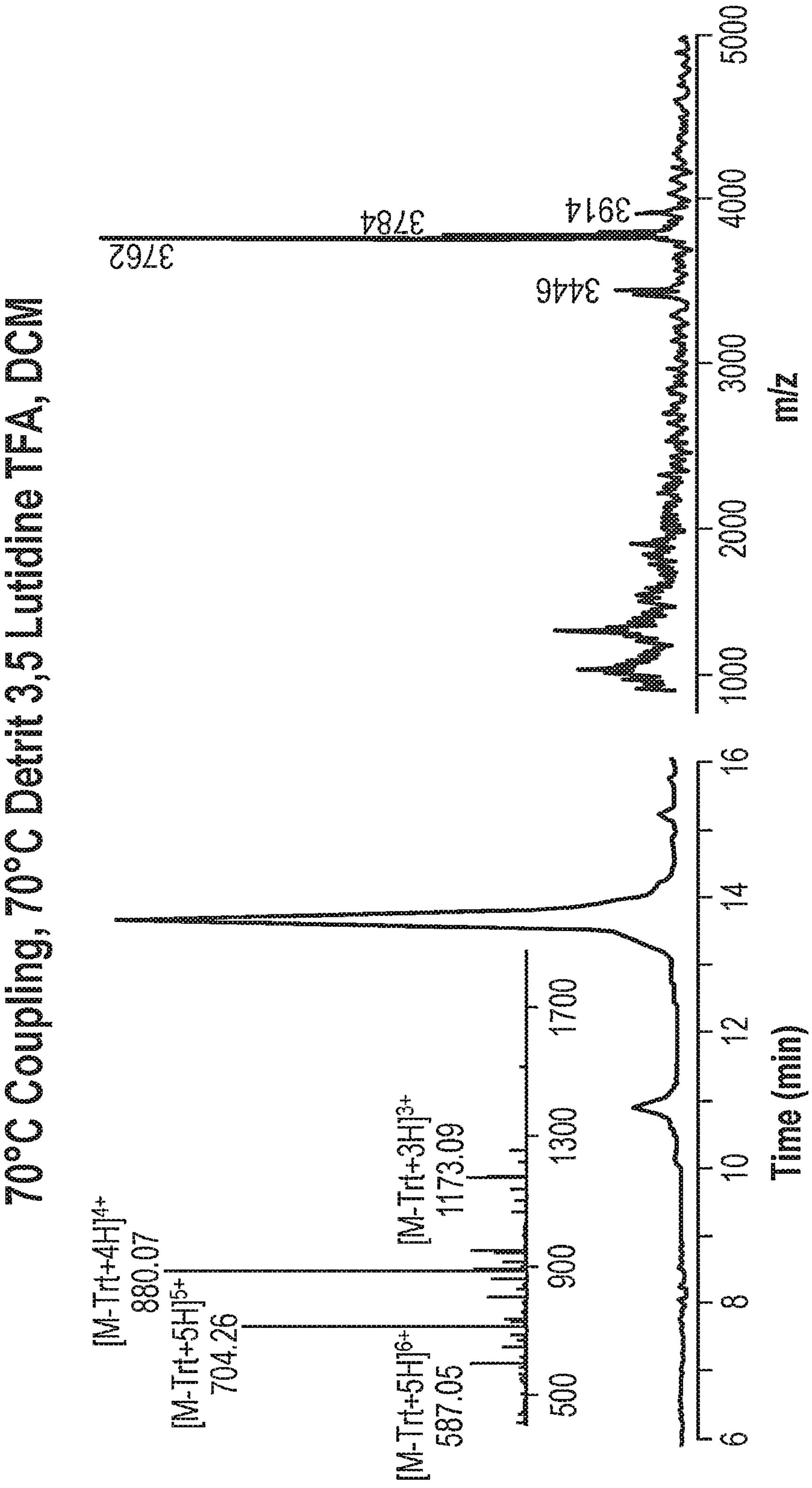
Figure 6D:
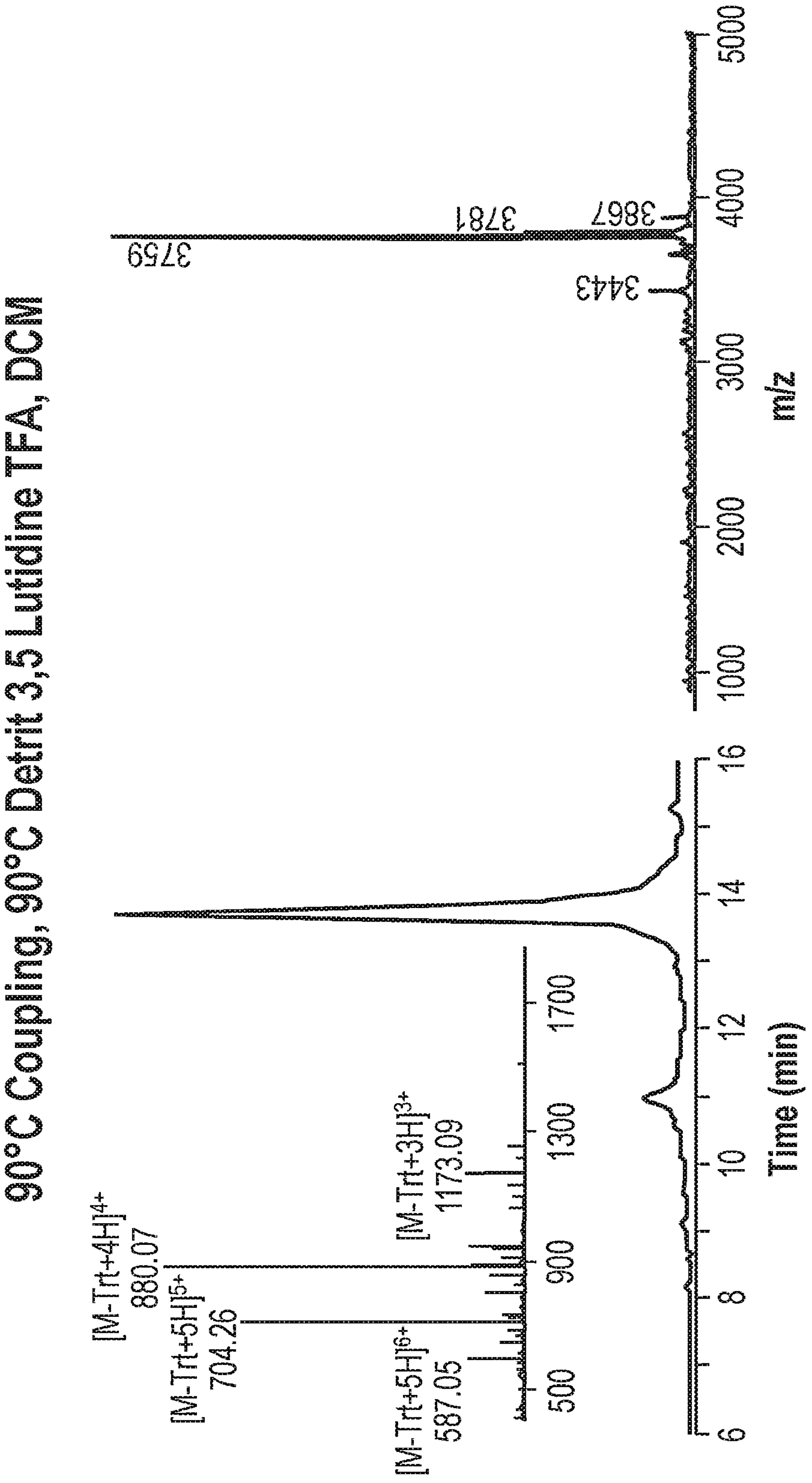
Figure 6E:
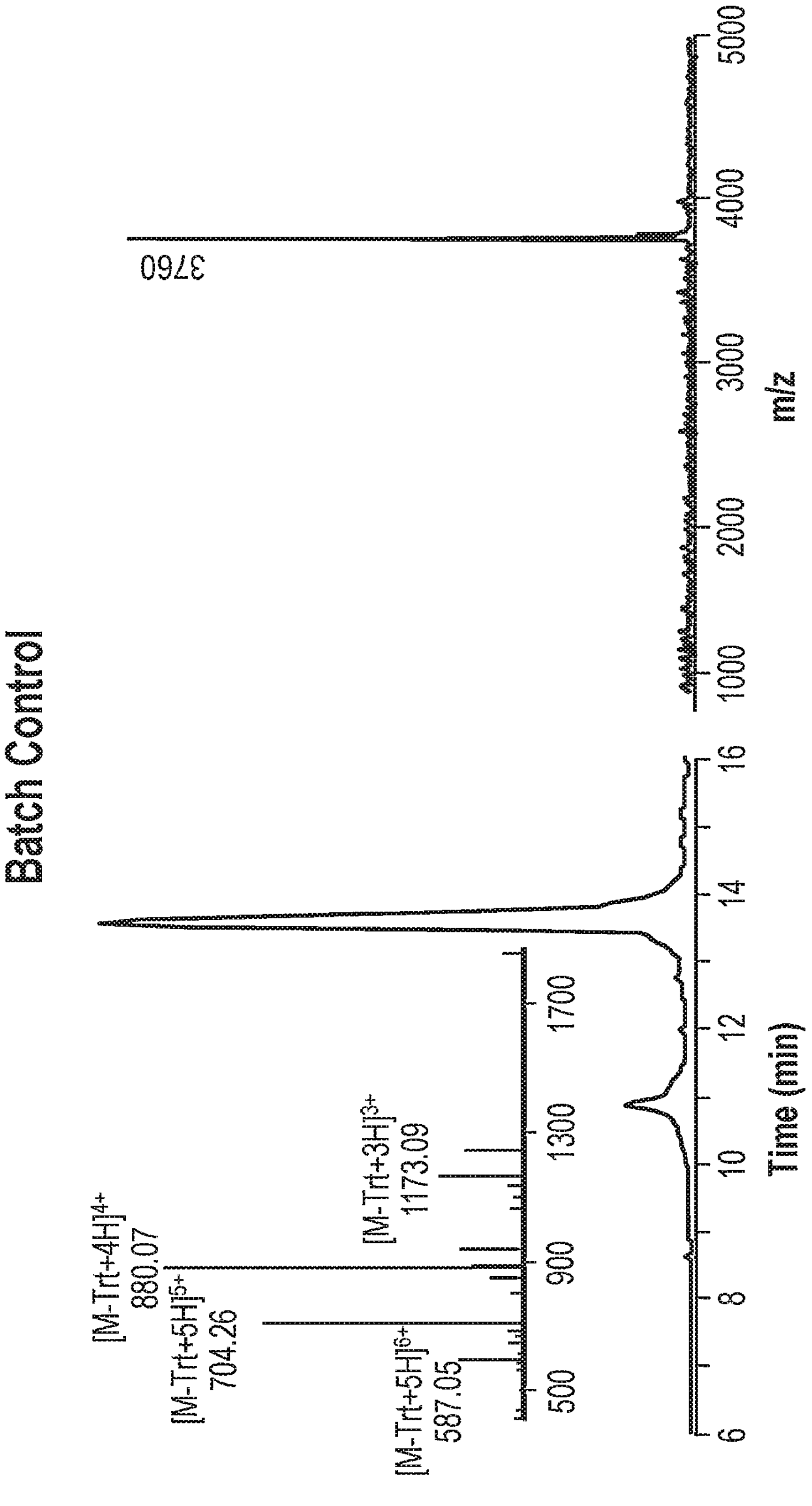

The flow PMO synthesizer is shown in (FIG. 4). Reagent reservoirs were GL45 threaded media bottles equipped with a top to maintain a positive pressure of dry nitrogen and allow anhydrous transfer of solvents. Each reagent reservoir was connected to one of four selectable ports on a four positon Swagelok SS-43ZFS2 manual selector valve. The common port was connected to the HPLC pump via a Swagelok (SS-QM2-B-200KR and SS-QM2-S-200) shutoff quick connect which could be disconnected when not in use to prevent siphoning of the pressurized solvents. The HPLC pump was a Varian 210 with a 25 ml/min stainless steel pump head. Low pressure (inlet side) tubing was ⅛" OD, 1/16" ID PFA. The HPLC pump outlet was connected to a 40 psi back pressure regulator (P-785) and male leur lock quick connect (Idex P-655) using 1/16" OD, 0.030" ID PFA tubing. When the HPLC pump was in use, this quick connect was mated to the female leur lock quick connect on the reactor inlet line. When the HPLC pump was not in use, the reactor inlet line was attached to a syringe of coupling reagent on the syringe pump (Harvard Apparatus PhD 3000).

The reactor inlet line consisted of a female luer lock quick connect (Idex P-658) and check valve (Idex CV-3316) joined with about 18 inches of 1/16" OD PFA tubing to a 5 foot stainless steel preheat loop (1/16" OD, 0.030" ID, Idex U-107) via a Swagelok union (SS-100-6). This preheat loop was connect to a reactor identical to the one described previously for peptide synthesis. The reactor outlet was connected to a 250 psi back pressure regulator (Idex P-788), which could be bypassed by opening a bypass valve (Idex P-733). The bypass fluid path rejoined the outlet of the back pressure regulator in a T (P-632), passed through a check valve (Idex P-788), and six inches of tubing before arriving at the methane sulfonic acid T (Swagelok SS-100-3). At this point, 20% MeHSO4 in DCM was optionally infused with a Knauer smartline HPLC pump with a 50 mL/min titanium head to regenerate the Trityl cation for UV monitoring of deprotection. The mixed fluid was then passed through a UV detector (Agilent G1315D), a 20 psi back pressure regulator (Idex P-791), and to waste.

Where not described, tubing downstream of the HPLC pump and syringe was 1/16" OD, 0.030" ID PFA. All ¼-28 flat bottom fittings were Idex super flangeless (XP-131 and XP-141).

Reagent Reservoirs

Figure 7:
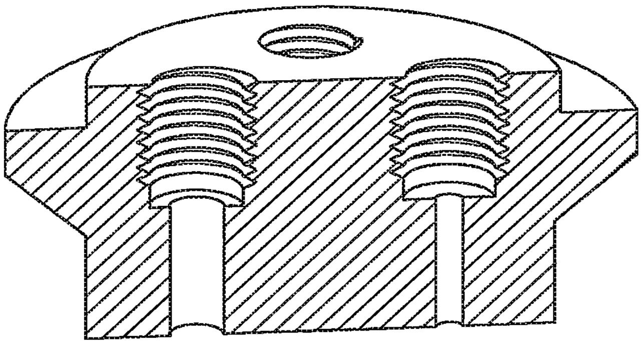
FIG. 7 shows the rendering of sectioned reagent reservoir top having three ports.

Reagent reservoirs were provisioned with machined adaptors for use with GL-45 caps with holes (Chemglass). These adaptors had three ¼-28 threaded ports (FIG. 7). Two ports had ⅛" thru holes; the third had a 1/16" thru hole. The first hole was used for a reagent withdraw line. The second was used as a fill port, and the third was used for the nitrogen gas supply (4 psi). The reagent withdraw line was a ⅛" line inserted into the bottom of the reagent reservoir and sealed in place with a super flangeless fitting (Idex XP-131). Nitrogen gas was supplied by a ⅛" line seated against the 1/16" thru hole and sealed in with a super flangeless fitting. The fill port consisted of a thin wall ⅛" OD, 0.1" ID, stainless steel tube inserted to just below the bottom of the machined adaptor and sealed in place with a super flangeless fitting. The free side was fitted with a shut off quick connect (Swagelok SS-QM2-B-200KR) that was sealed when not in use but could be used to fill the reservoir from a second reservoir of anhydrous solvent under slightly higher pressure. The second reservoirs were of a similar design and 10 psi argon was used to transfer dry solvent. During filling, the nitrogen system was allowed to vent through a 5 psi back pressure regulator and oil bubbler.

Example 7: General Procedure for Flow Synthesis

The following procedure was used for flow synthesis. Resin was loaded into the reactor, the reactor was connected to the HPLC pump, and halogenated wash solvent was delivered at 10 mL/min to remove air. The flow was stopped and the resin was allowed to swell for 10 minutes. The flow protocol was initiated with an initial halogenated solvent wash at 10 mL/min for 60 seconds. Detritylation was performed with 100 mM of a pyridine trifluoroacetate for 120 seconds at the same flow rate. The detritylation step can also be performed using Collidone, Lutidine, or 4-Cyanopyridine (FIG. 3A, FIG. 3B, FIG. 3C, and FIG. 3D). After a 30 second halogenated solvent wash, neutralization was performed with 5% DIEA or NEM for 60 seconds. The resin was then washed with the halogenated solvent and DMI for 60 seconds each at 10 mL/min. The HPLC pump was then halted for the coupling step. Coupling solution (0.2 M subunit, 0.4 M DIEA or NEM, and 0.21 M LiBr in dry DMI) was placed in a 10 mL syringe and delivered via syringe pump at 3 mL/min over 1 minute (0.5 mmol monomer) or 2 minutes (1 mmol monomer). It was determined that the monomers were stable at temperatures between 90° C. and 110° C. in the presence of Lithium Bromide (FIG. 1). When all of the solution was delivered, the HPLC pump delivered DMI at 3 mL/min for three minutes. This protocol was repeated for each residue until synthesis was complete. The finished resin was removed from the reactor, washed 5 times with DCM in a fritted syringe (Torviq), and dried under vacuum. Cleavage was performed as above.

For steps at elevated temperature, the reactor and preheat loop were placed in a thermostated water bath.

Figure 2:
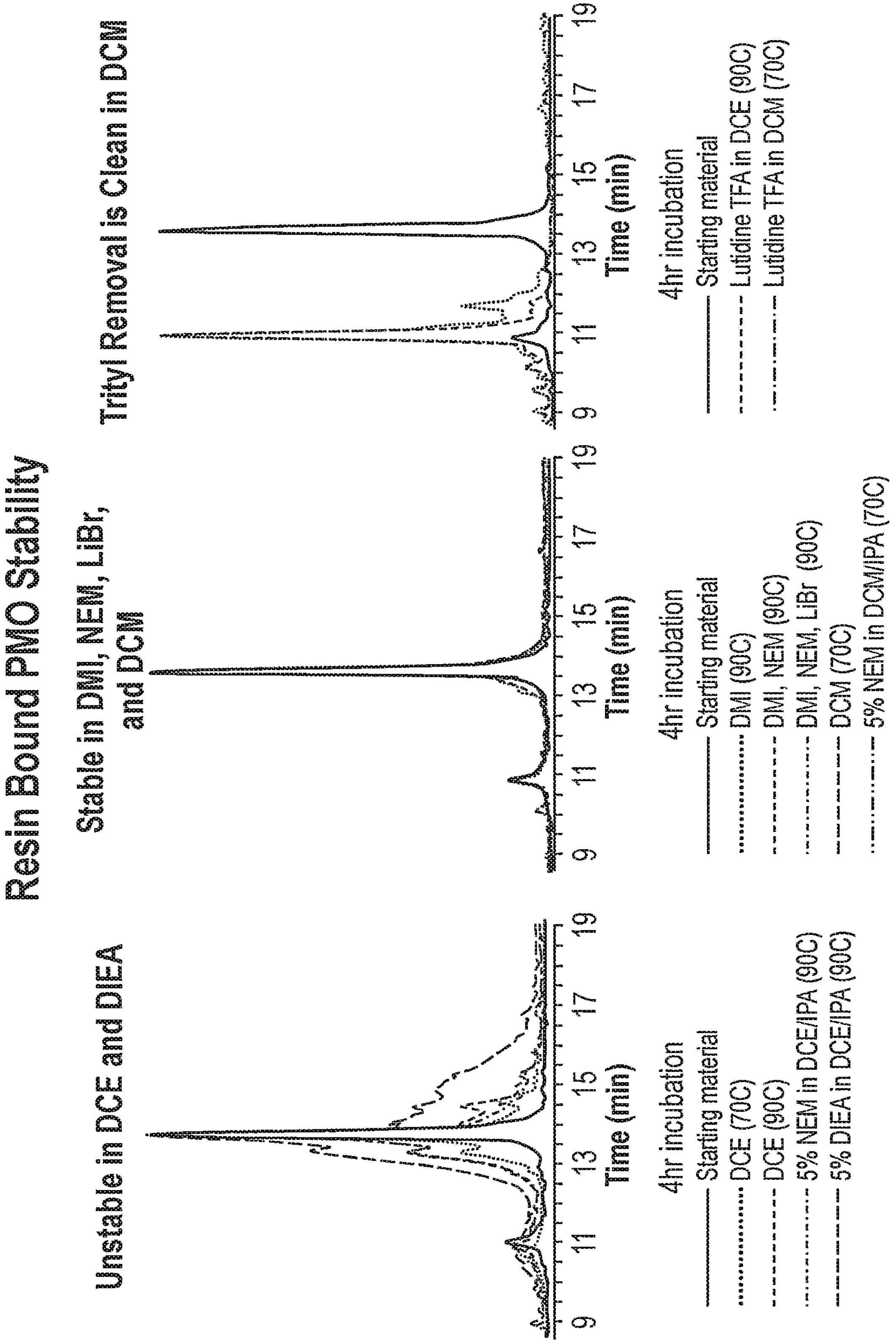
FIG. 2 shows the stability of the resin-bound PMO.
Figures 3A, 3B, 3C, 3D:
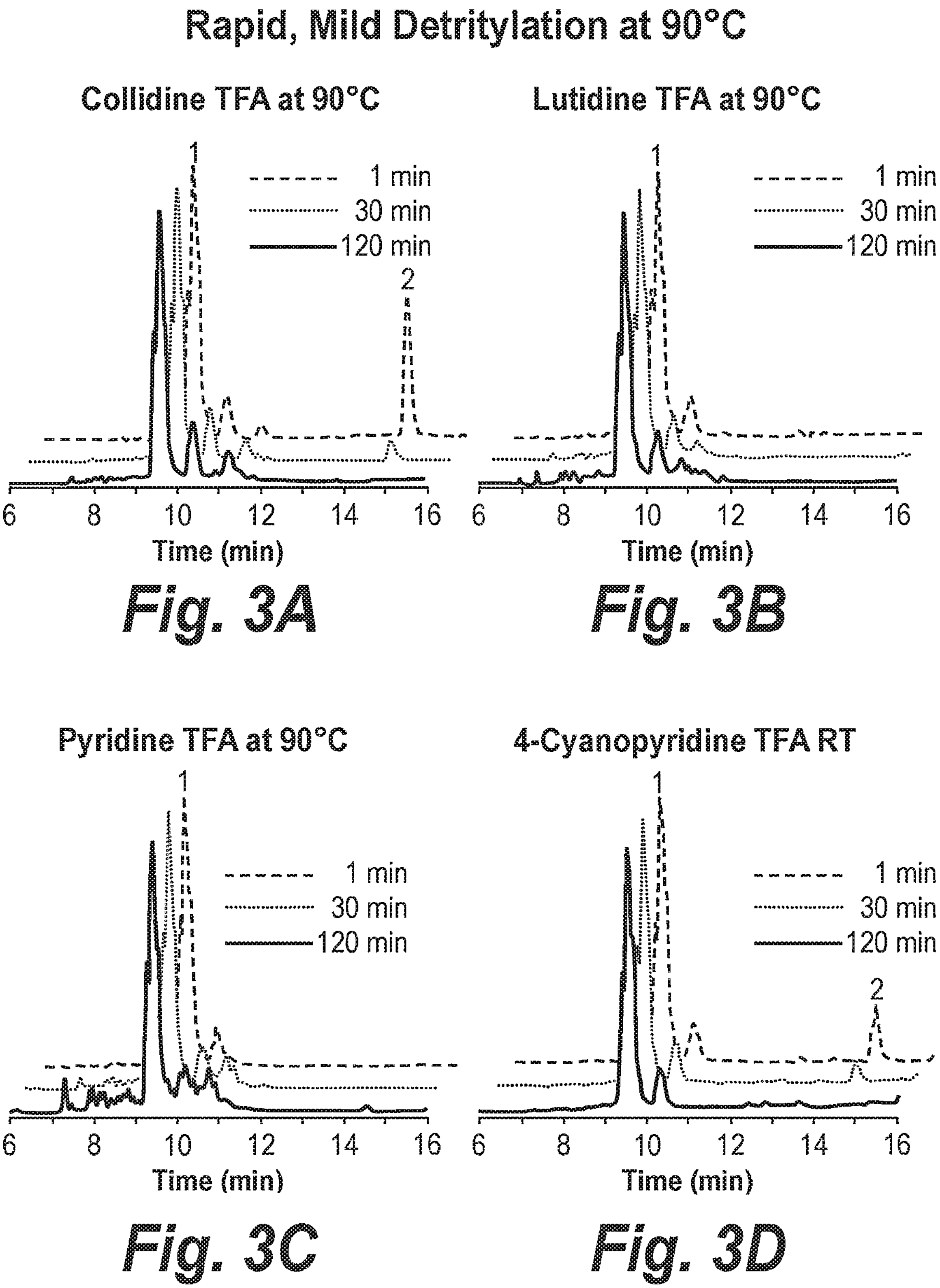
FIG. 3A Collidine TFA at 90° C.
FIG. 3B Lutidine TFA at 90° C.
FIG. 3C Pyridine TFA at 90° C.
FIG. 3D 4-Cyanopyridine TFA at RT.

For HPLC purification, resin was cleaved under mild conditions (4:1 ethanol/ammonium hydroxide) and then isolated by solid-phase extraction (SPE). Prior to the cleavage using said mild conditions, the resin-bound PMO was stable to a variety of reaction conditions (FIG. 2). Initially, the cleaved resin was filtered and washed 4 times with methanol. The cleavage solution and washes were collected and concentrated to dryness using a rotary evaporator. The residue was dissolved in 10 mL of Milli-Q water prior to SPE. Separately, SPE columns were prepared and conditioned using the following procedure. 20 mL Econo-Pac columns from Bio-Rad were charged with 3-4 mL of Amberchrome CG-300M resin and sealed with a frit. Then 8 mL of the following solutions were added to the column, in order, and drained before adding the next solution: 80% ACN in 1% $NH_4OH$, 0.5 M NaOH in 20% EtOH, Milli-Q water, 50 mM $H_3PO_4$ in 80% ACN, Milli-Q water, 0.5 M NaOH in 2000 EtOH, Milli-Q water, 1% $NH_4OH$. When conditioning was complete, the column was stored in 8 mL of 10% $NH_4OH$ at room temperature until used. The column was rinsed two times with 12 mL of Milli-Q water before loading the PMO onto the column. Then, the column was rinsed once with 3 mL of 1 M NaCl, followed by three rinses with 12 mL of Milli-Q water, and once with 3 mL of 10% acetonitrile in water. The PMO was then eluted with two 3 mL rinses of 50% acetonitrile in water. The eluent from the 50% acetonitrile wash was collected into a pre-weighed 50 mL conical centrifuge tube and lyophilized to afford the crude PMO as a white powder suitable for LC/MS analysis and/or preparative HPLC purification.

Several PMOs were purified on a mass-directed purification system consisting of an Agilent 1260 Infinity Quaternary HPLC coupled to an Agilent 6130 single quadrupole mass spectrometer (FIG. 5A, FIG. 5B, FIG. 5C, FIG. 5D, FIG. 5E, FIG. 6A, FIG. 6B, FIG. 6C, FIG. 6D, and FIG. 6E). The solvent mixtures used for purification were as follows: A=5 mM $NH_4OAc$ (pH=8), B=90% acetonitrile+10% 5 mM $NH_4OAc$ (pH=8). Purification was performed using the following conditions: Column: Zorbax 300-SB C3 (5 μm, 21.2×100 mm); Flow Rate: 20 mL/min; Gradient: 0-2 min 2% B, 2-60 min 2-60% B, 60-70 min 75% B.

TABLE 6

Acronyms

| Acronym | Name |
|---|---|
| DBU | 1,8-Diazabicycloundec-7-ene |
| DCM | Dichloromethane |
| DIPEA | N,N-Diisopropylethylamine |
| DMI | 1,3-Dimethyl-2-imidazolidinone |
| DTT | Dithiothreitol |
| IPA | Isopropyl alcohol |
| MW | Molecular weight |
| NEM | N-Ethylmorpholine |
| NMP | N-Methyl-2-pyrrolidone |
| RT | Room temperature |
| TFA | 2,2,2-Trifluoroacetic acid |
| TFE | 2,2,2-Trifluoroethanol |

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the disclosure described herein. Such equivalents are intended to be encompassed by the following claims.

The invention claimed is:

1. A process for preparing an oligomeric compound of Formula (I):

(I)

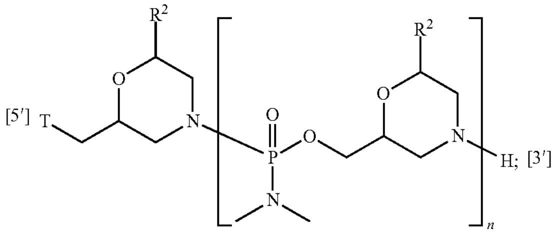

wherein n is an integer from 9 to 39;

T is OH or

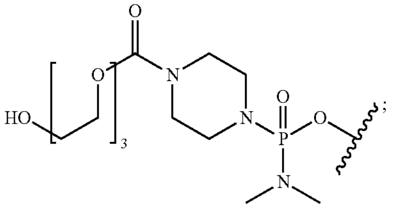

and each $R^2$ is, independently for each occurrence, selected from the group consisting of:

(C)

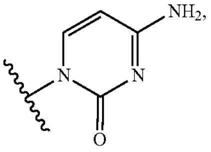

(G0

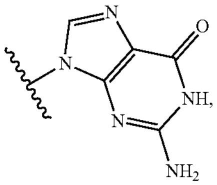

-continued
(T)
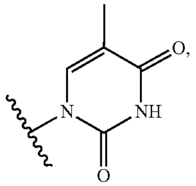
(A)
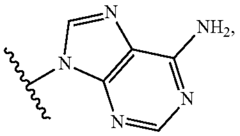
(5mC)
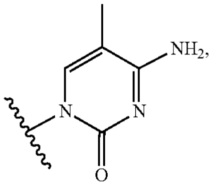
(U)
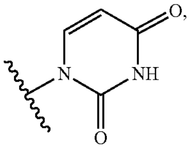
and
(I)
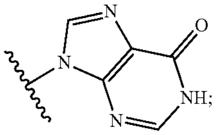
wherein the process comprises the sequential steps of:
(a) contacting a compound of Formula (A1):
(A1)
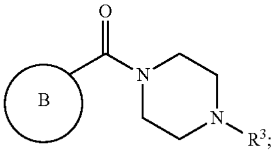
wherein
B is
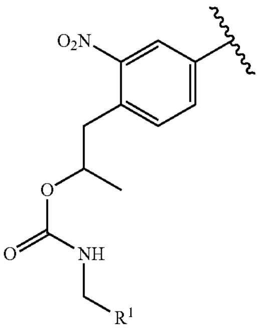
or
-continued
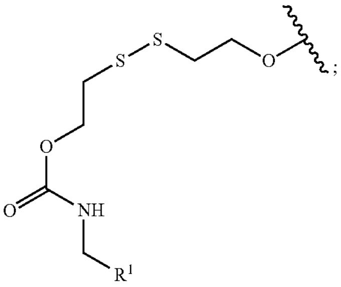
$R^1$ is a support-medium; and
$R^3$ is selected from the group consisting of trityl, monomethoxytrityl, dimethoxytrityl and trimethoxytrityl;
with a deblocking agent to form the compound of Formula (II):
(II)
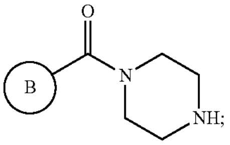
wherein B is
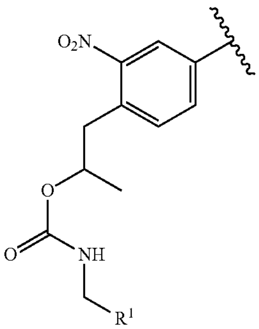
or
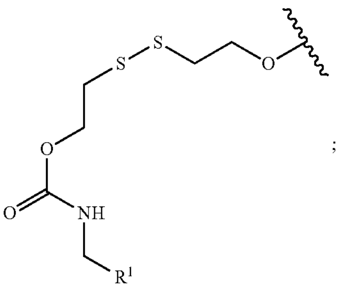
;

and
$R^1$ is a support-medium;
(b) contacting the compound of Formula (II) with a compound of Formula (A2):
(A2)
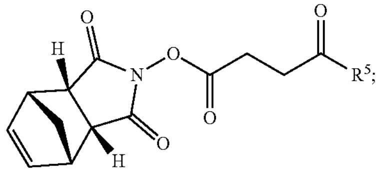
wherein $R^5$ is
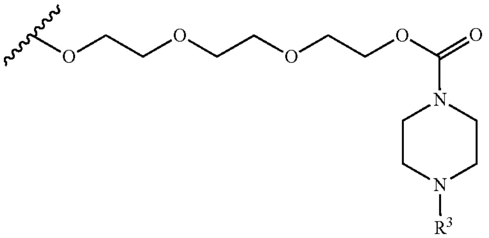
or
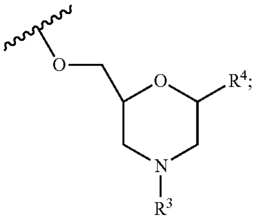
$R^3$ is selected from the group consisting of trityl, monomethoxytrityl, dimethoxytrityl and trimethoxytrityl; and
$R^4$ is selected from the group consisting of:
(PC)
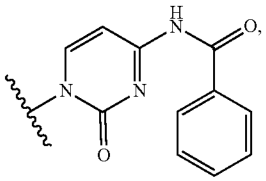
(DPg)
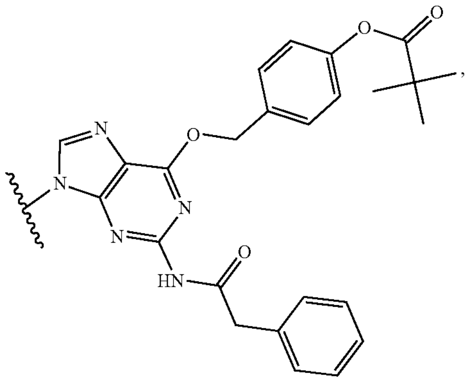
-continued
(T)
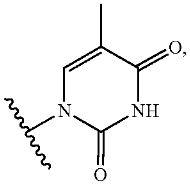
(PA)
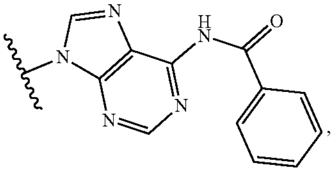
(P5mC)
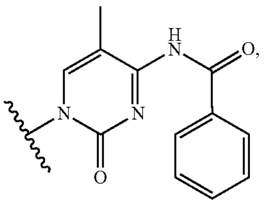
(U)
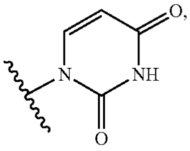
(I)
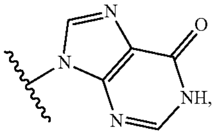
and
(PG)
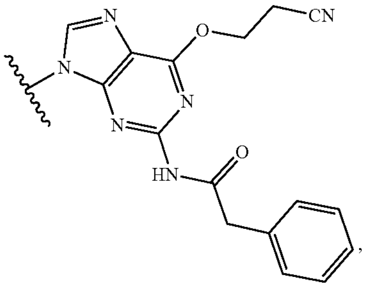
to form a compound of Formula (A3):
(A3)
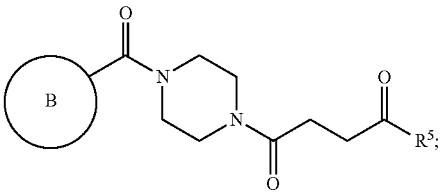

wherein
B is
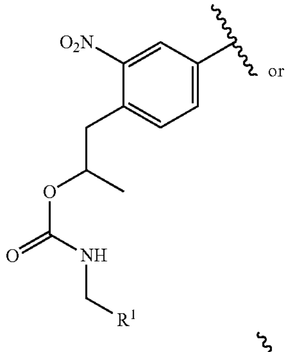
or
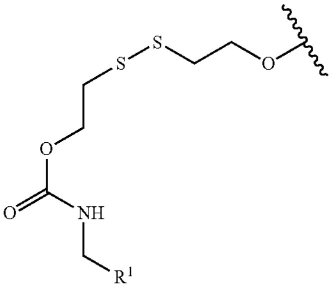
;
$R^1$ is a support-medium;
$R^5$ is
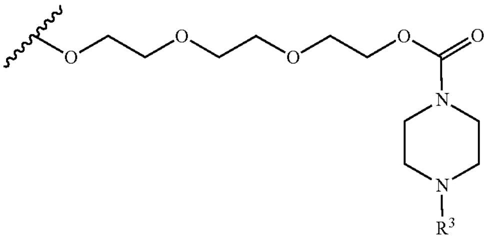
or
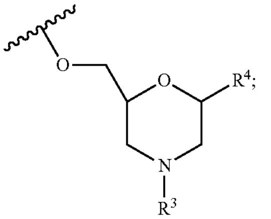
$R^3$ is selected from the group consisting of trityl, monomethoxytrityl, dimethoxytrityl and trimethoxytrityl; and
$R^4$ is selected from the group consisting of:
(PC)
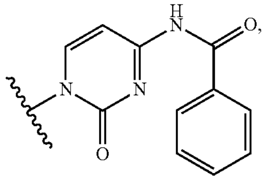
-continued
(DPG)
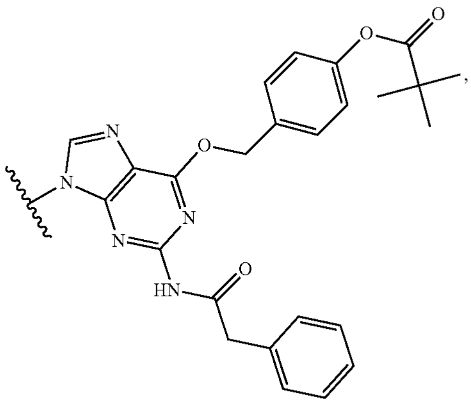
,
(T)
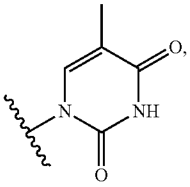
(PA)
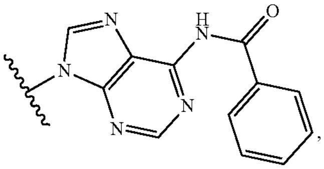
,
(P5mC)
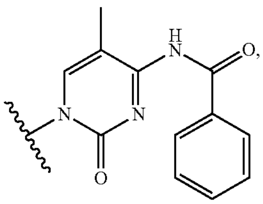
(U)
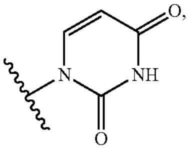
(I)
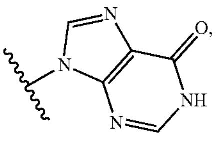
and
(PG)
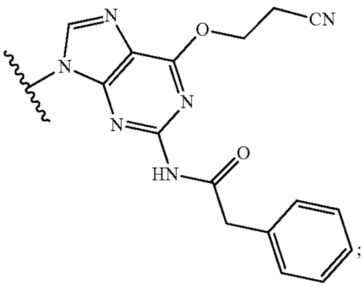
;

(c) contacting the compound of Formula (A3) with a deblocking agent to form a compound of Formula (IV):
(IV)
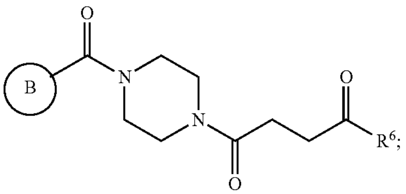
wherein B is
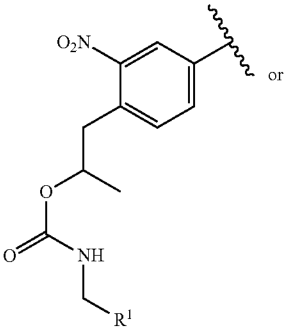
or
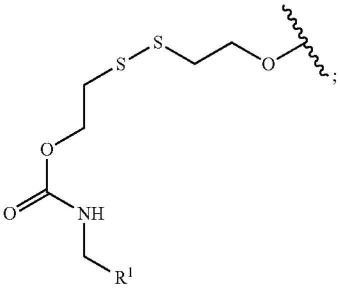
$R^1$ is a support-medium;
$R^6$ is
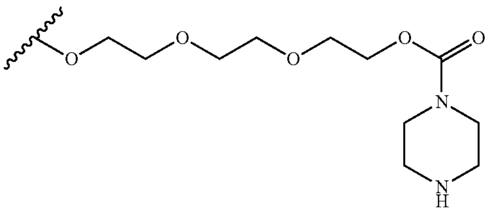
or
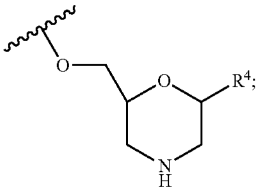
and
$R^4$ is selected from the group consisting of:
(PC)
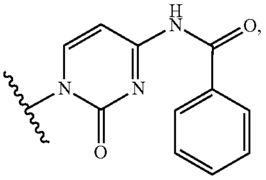
(DPG)
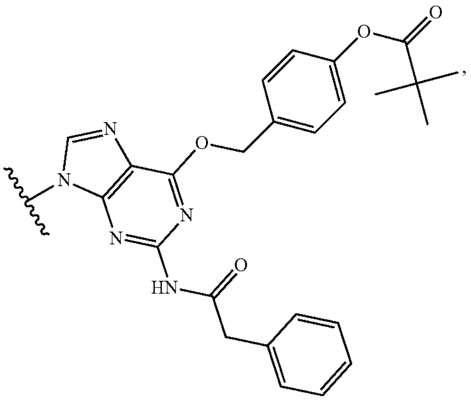
(T)
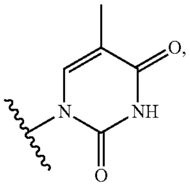
(PA)
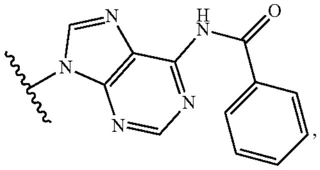
(P5mC)
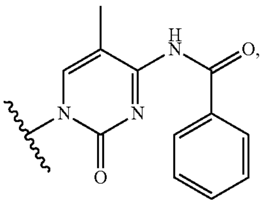
(U)
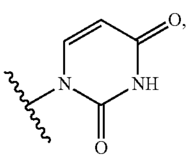
(I)
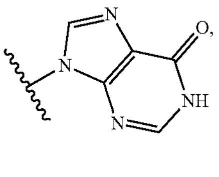
and -continued
(PG)
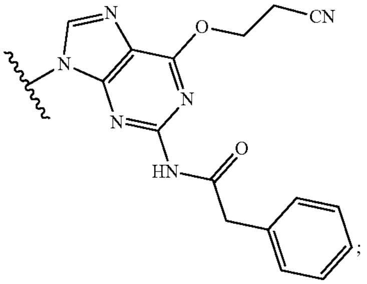
(d) contacting the compound of Formula (IV) with a compound of Formula (A4):
(A4)
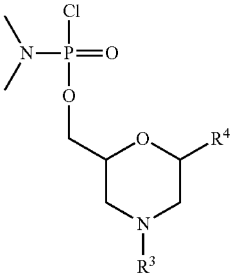
in the presence of a Lewis acid catalyst;
wherein
$R^3$ is selected from the group consisting of trityl, monomethoxytrityl, dimethoxytrityl and trimethoxytrityl; and
$R^4$ is selected from the group consisting of:
(PC)
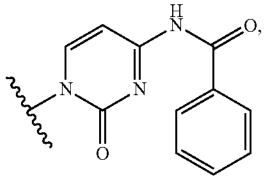
(DPG)
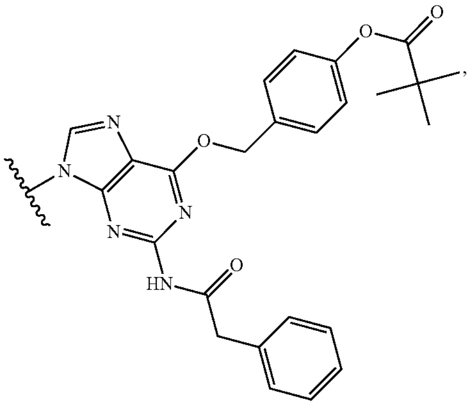
-continued
(T)
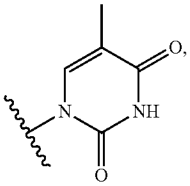
(PA)
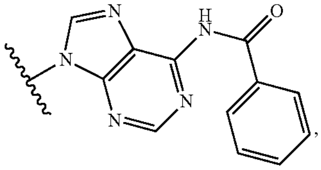
(P5mC)
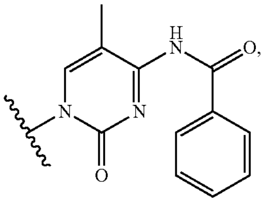
(U)
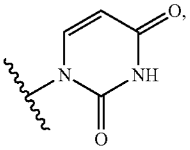
(I)
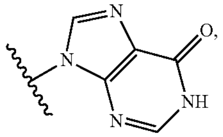
and
(PG)
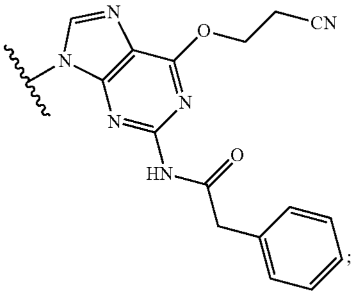
to form a compound of Formula (A5):
(A5)
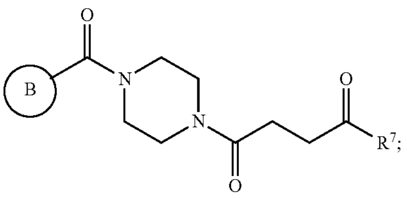

wherein $R^7$ is of Formula (A5a) or Formula (A5b):
(A5a)
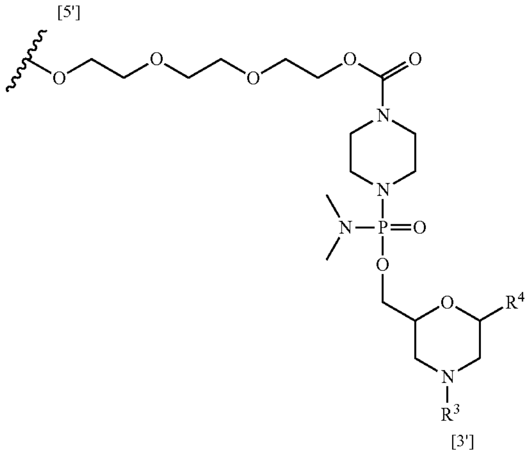
or
(A5b)
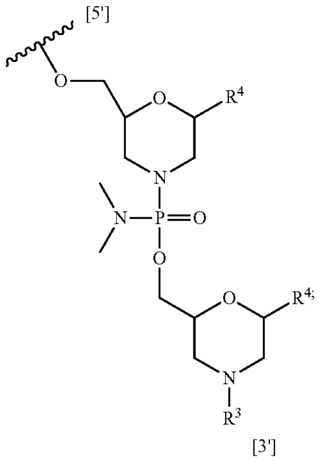
B is
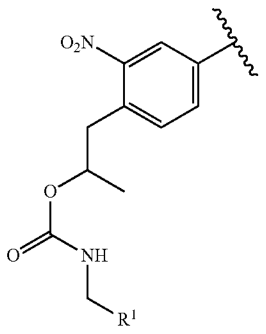
or
-continued
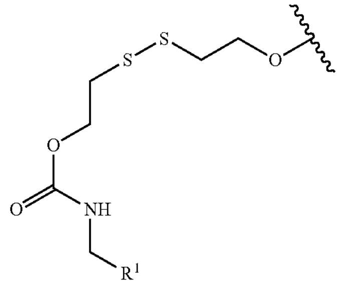
;
$R^1$ is a support-medium;
$R^3$ is selected from the group consisting of trityl, monomethoxytrityl, dimethoxytrityl and trimethoxytrityl; and
$R^4$ is selected from:
(PC)
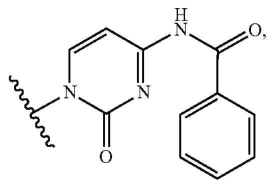
(DPG)
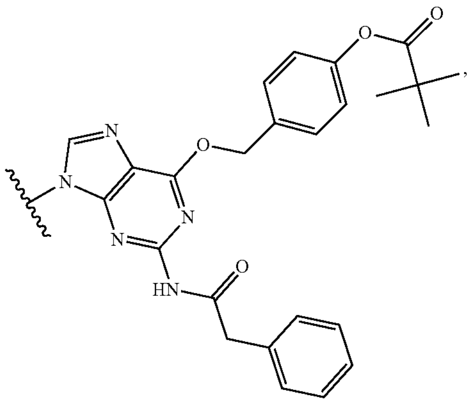
(T)
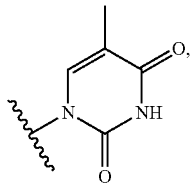
(PA)
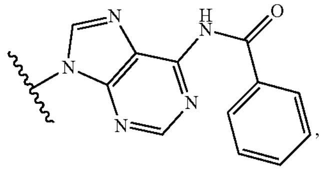

-continued (P5mC)

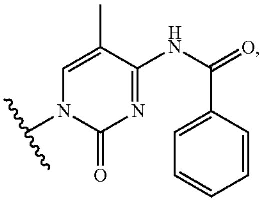

(U)

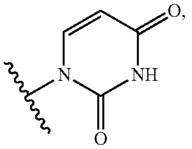

(I)

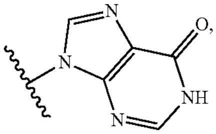

and (PG)

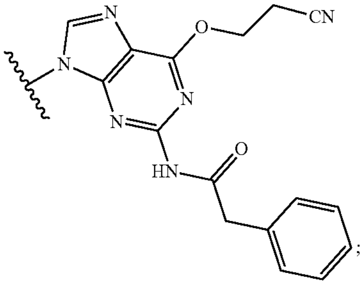

(e) performing Y iterations of the sequential steps of:

(e1) contacting the product formed by the immediately prior step with a deblocking agent; and (e2) contacting the compound formed by the immediately prior step with a compound of Formula (A8):

(A8)

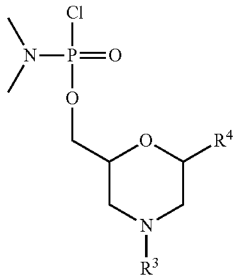

in the presence of a Lewis acid catalyst;

wherein

Y is n−1 if $R^7$ is of the Formula (A5a) or Y is n−2 if $R^7$ is of the Formula (A5b);

$R^3$ is selected from the group consisting of trityl, monomethoxytrityl, dimethoxytrityl and trimethoxytrityl; and $R^4$ is, independently for each compound of Formula (A8), selected from the group consisting of:

(PC)

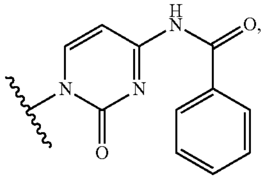

(DPG)

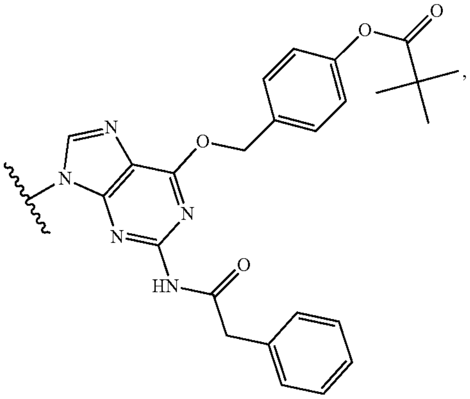

(T)

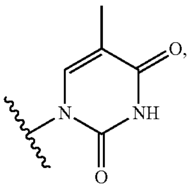

(PA)

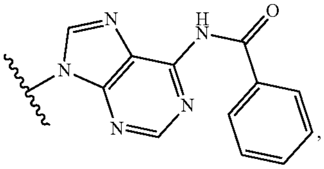

(P5mC)

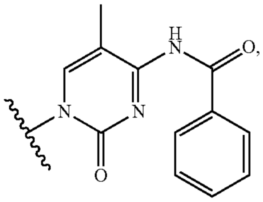

(U)

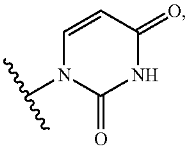

(I)

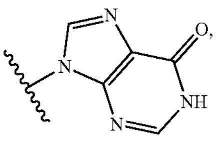

and

-continued
(PG)
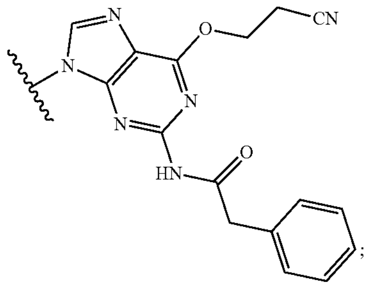
;
to form a compound of Formula (A9):
(A9)
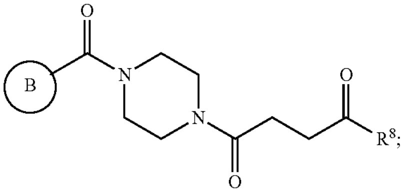
wherein $R^8$ is
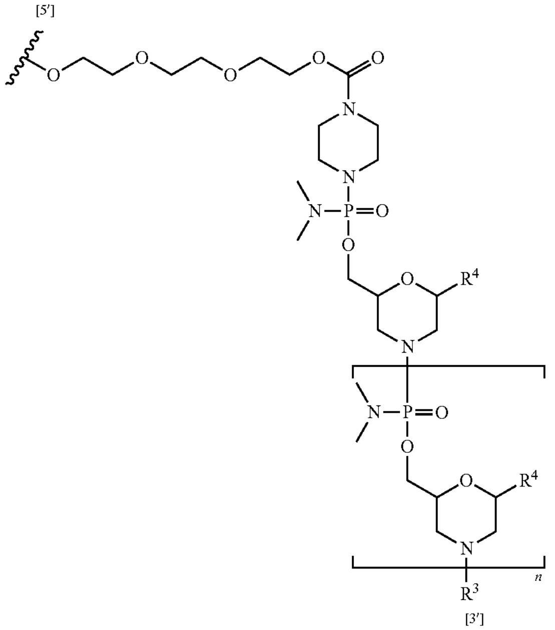
or
-continued
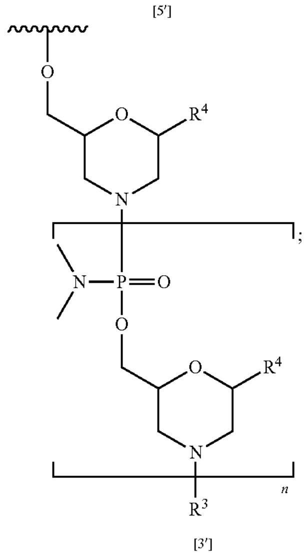
;
B is
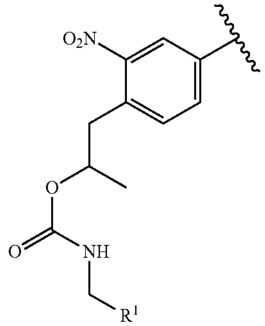
or
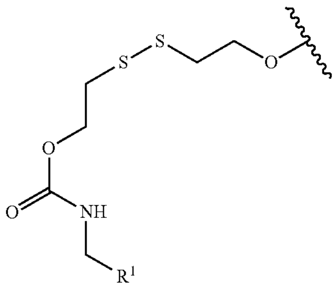
;
n is an integer from 9 to 39;
$R^1$ is a support-medium;
$R^3$ is selected from the group consisting of trityl, monomethoxytrityl, dimethoxytrityl and trimethoxytrityl; and
$R^4$ is, independently for each occurrence, selected from the group consisting of:

(PC)
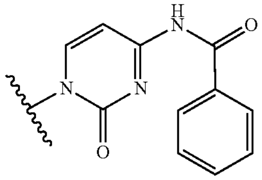
,
(DPG)
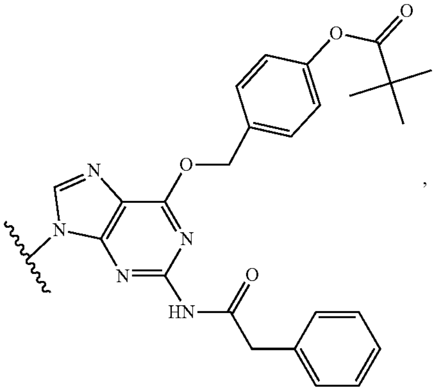
,
(T)
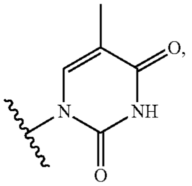
(PA)
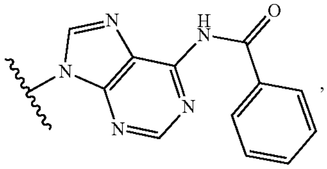
,
(P5mC)
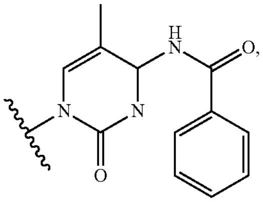
(U)
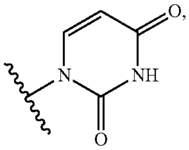
(I)
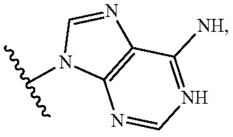
and
-continued
(PG)
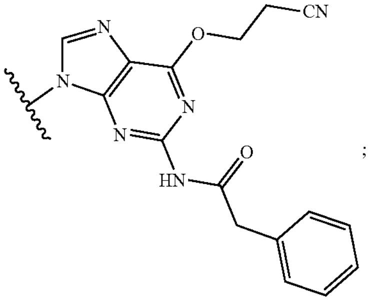
;
(f) contacting the compound of Formula (A9) with a deblocking agent to form a compound of Formula (A10):
(A10)
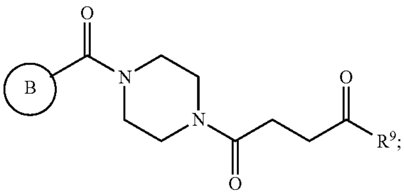
wherein $R^9$ is
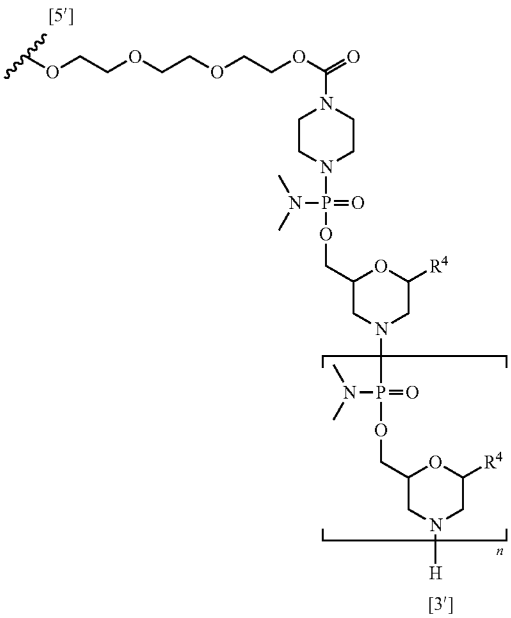
or -continued
[5']
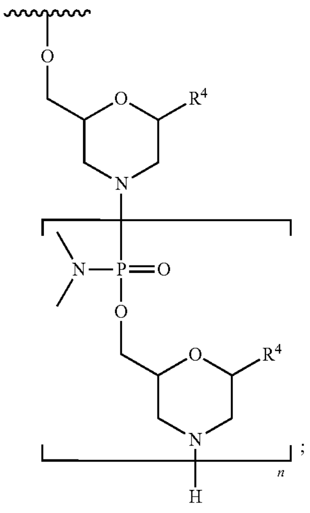
[3']
B is
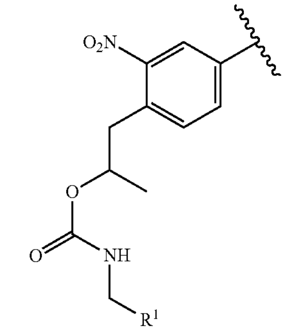
or
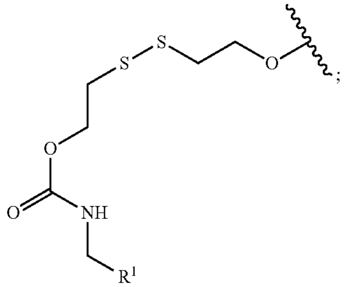
n is an integer from 9 to 39;
$R^1$ is a support-medium; and
$R^4$ is, independently for each occurrence, selected from the group consisting of:
(PC)
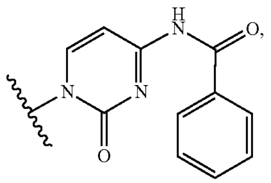
-continued
(DPG)
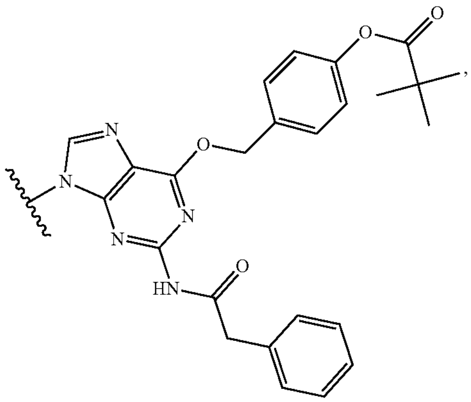
(T)
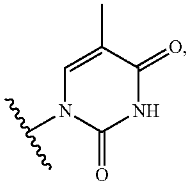
(PA)
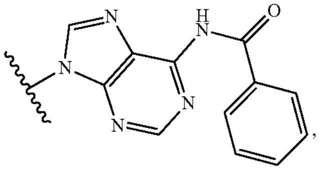
(P5mC)
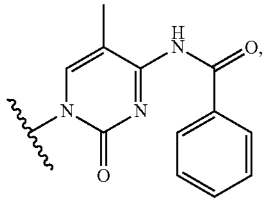
(U)
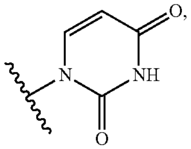
(I)
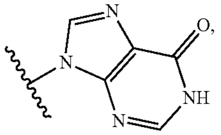
and
(PG)
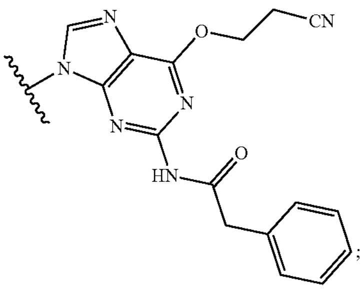

(g) contacting the compound of Formula (A10) with a cleaving agent to form a compound of Formula (A11):
(A11)
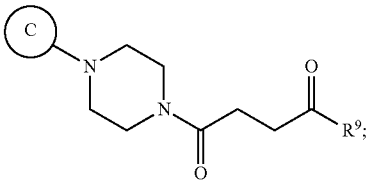
wherein
$R^9$ is
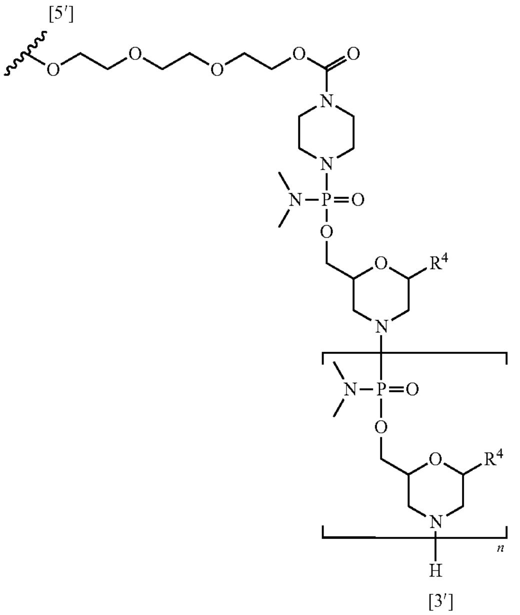
or
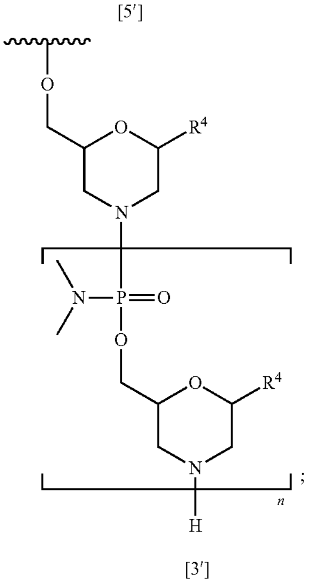
C is
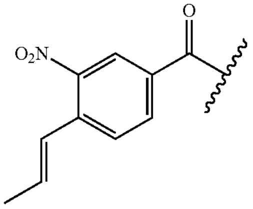 [SMILES: *C(=O)c1ccc(/C=C/C)c([N+](=O)[O-])c1]
or H;
n is an integer from 9 to 39; and
$R^4$ is, independently for each occurrence, selected from the group consisting of:
(PC)
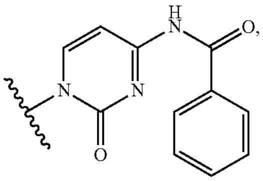
(DPG)
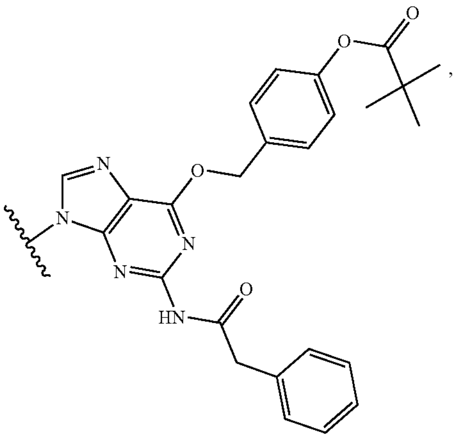
(T)
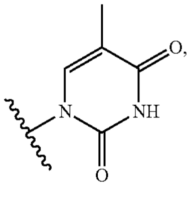
(PA)
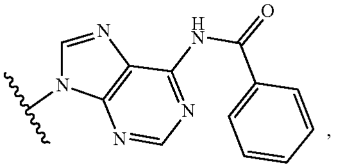
(P5mC)
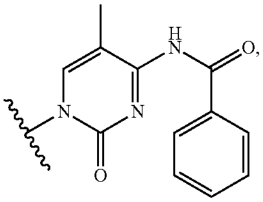

-continued (U)

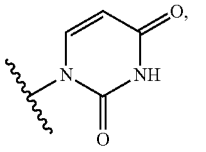

(I)

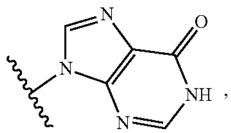

, and (PG)

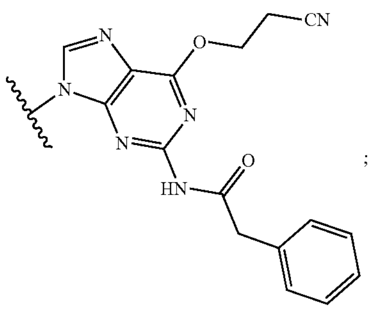

;

and (h) contacting the compound of Formula (A11) with a deprotecting agent to form the oligomeric compound of Formula (I), wherein any of steps (a), (b), (c), (d), (e1), (e2), (f), (g), or (h) are carried out in a continuous synthesis.

2. The process of claim 1, wherein one of steps (d) or (e2) further comprises contacting the compound formed by the immediately prior step with a capping agent.

3. The process of claim 1, wherein steps (a), (c), (e1), and (f) further comprise contacting the deblocked compound of each step with a neutralization agent.

4. The process of claim 1, wherein the compounds of Formula (A4) and Formula (A8) are each, independently, in a solution comprising N-ethylmorpholine and dimethylimidazolidinone.

5. The process of claim 1, wherein the cleavage agent comprises dithiothreitol and 1,8-diazabicyclo[5.4.0]undec-7-ene.

6. The process of claim 1, wherein for steps (a)-(g), B is

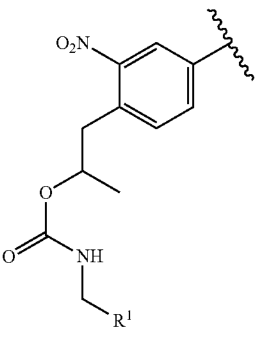

and for step (h), C is

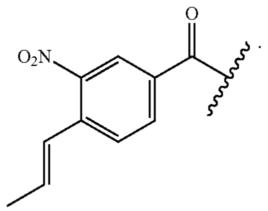 [SMILES: *C(=O)c1ccc(/C=C/C)c([N+](=O)[O-])c1]

7. The process according to claim 1, wherein any of steps (a), (b), (g), and (h) are carried out in a batchwise synthesis and steps (c), (d), (e1), (e2), and (f) are carried out in a continuous synthesis.

8. The process of claim 1, wherein the deblocking agent is selected from the group consisting of chloroacetic acid, dichloroacetic acid, trichloroacetic acid, fluoroacetic acid, difluoroacetic acid, and trifluoroacetic acid.

9. The process of claim 1, wherein the deblocking agent used in each step is a solution comprising a halogenated acid.

10. The process of claim 1, wherein the Lewis acid is selected from a group consisting of LiCl, LiBr, LiI, and LiOTf.

11. The process of claim 1, wherein the neutralization agent is in a solution comprising a halogenated solvent and isopropyl alcohol.

12. The process of claim 1, wherein the neutralization agent is a monoalkyl, dialkyl, or trialkyl amine.

13. The process of claim 1, wherein the process is performed in a flow-through reactor, the flow-through reactor comprising at least:

(a) a feeding zone, wherein the feeding zone comprises one or more feed lines each equipped with a pump, and wherein the inlet zones of the feed lines are independently connected to vessels comprising a neutralizing agent, coupling solvent, a deblocking agent, washing solvent, and a compound of Formula (A8):

(A8)

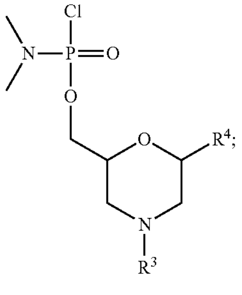

wherein $R^3$ is selected from the group consisting of trityl, monomethoxytrityl, dimethoxytrityl and trimethoxytrityl; and $R^4$ is, independently for each compound of Formula (A8), selected from the group consisting of:

(PC)

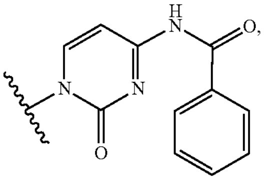

(DPG)

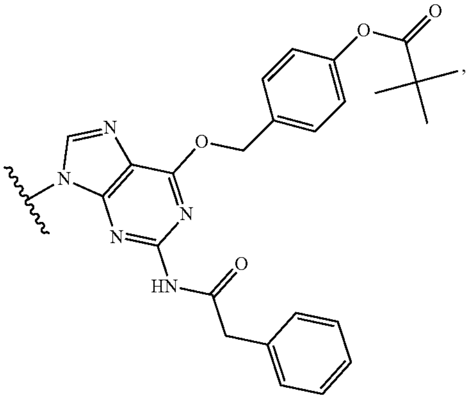

(T)

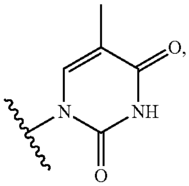

(PA)

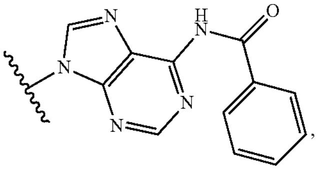

-continued (P5mC)

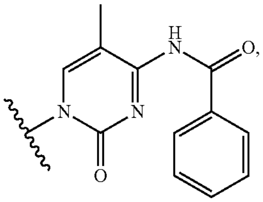

(U)

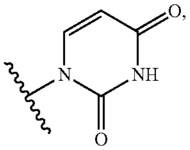

(I)

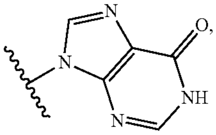

and (PG)

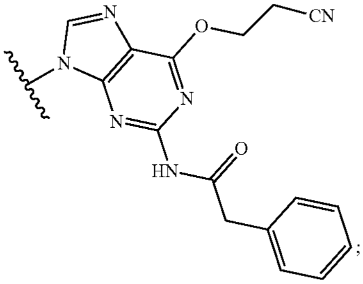

wherein the compound of Formula (A8) is dissolved in a coupling solvent;

(b) a reaction zone that is connected to the outlet zone of the one or more feed lines and which contains a PMO synthesis resin;

(c) an outlet zone, whereby waste stream or product can be independently collected;

(d) a pressure control device; and (e) a means of independently controlling the temperature of the feeding zone and the reaction zone.

* * * * *